US007381206B2

(12) United States Patent
Cucin

(10) Patent No.: US 7,381,206 B2
(45) Date of Patent: Jun. 3, 2008

(54) POWER-ASSISTED TISSUE-ASPIRATION INSTRUMENT SYSTEM EMPLOYING AN ELECTRONICALLY-CONTROLLED AIR-FLOW VALVE ASSEMBLY WITHIN AN EXTERNAL INSTRUMENT CONTROLLER

(76) Inventor: Robert L. Cucin, 120 Central Park South, New York, NY (US) 10019

( * ) Notice: Subject to any disclaimer, the term of this patent is extended or adjusted under 35 U.S.C. 154(b) by 0 days.

(21) Appl. No.: 11/145,578

(22) Filed: Jun. 3, 2005

(65) Prior Publication Data

US 2005/0267446 A1 Dec. 1, 2005

Related U.S. Application Data

(63) Continuation of application No. 10/442,645, filed on May 21, 2003, which is a continuation-in-part of application No. 09/507,266, filed on Feb. 18, 2000, now Pat. No. 6,394,973, which is a continuation-in-part of application No. 08/882,927, filed on Jun. 26, 1997, now Pat. No. 5,795,323, which is a continuation of application No. 08/307,000, filed on Sep. 16, 1994, now Pat. No. 5,643,198, which is a continuation of application No. 07/627,240, filed on Dec. 14, 1990, now Pat. No. 5,348,535.

(51) Int. Cl.
*A61M 1/00* (2006.01)
*A61M 27/00* (2006.01)

(52) U.S. Cl. ...................... 604/542; 604/540; 604/541; 604/543

(58) Field of Classification Search ........ 604/540–543, 604/317
See application file for complete search history.

(56) References Cited

U.S. PATENT DOCUMENTS

| | | | | |
|---|---|---|---|---|
| 3,082,805 A | | 3/1963 | Royce | |
| 3,699,968 A | | 10/1972 | Bolduc | |
| 3,732,858 A | | 5/1973 | Banko | |
| 3,734,099 A | | 5/1973 | Bender et al. | |
| 3,945,375 A | | 3/1976 | Banko | |
| 3,955,579 A | | 5/1976 | Bridgman | |
| 3,994,297 A | | 11/1976 | Kopf | |
| 4,167,944 A | | 9/1979 | Banko | |
| 4,203,444 A | | 5/1980 | Bonnell et al. | |
| 4,311,140 A | | 1/1982 | Bridgman | |
| 4,314,560 A | | 2/1982 | Helfgott et al. | |
| 4,463,759 A | | 8/1984 | Garito et al. | |
| 4,479,107 A | * | 10/1984 | Bleeke | 338/176 |
| 4,487,600 A | | 12/1984 | Brownville et al. | |
| 4,530,356 A | | 7/1985 | Helfgott et al. | |
| 4,536,180 A | | 8/1985 | Johnson | |
| 4,577,629 A | | 3/1986 | Martinez | |
| 4,589,414 A | | 5/1986 | YYoshida et al. | |
| 4,657,016 A | | 4/1987 | Garito et al. | |
| 4,674,502 A | | 6/1987 | Imonti | |
| 4,735,605 A | | 4/1988 | Swartz | |
| 4,754,754 A | | 7/1988 | Garito et al. | |
| 4,767,404 A | * | 8/1988 | Renton | 604/48 |
| 4,775,365 A | | 10/1988 | Swartz | |
| 4,792,327 A | | 12/1988 | Swartz | |
| 4,815,462 A | | 3/1989 | Clark | |
| 4,850,354 A | | 7/1989 | McGurk-Burleson et al. | |
| 4,886,491 A | | 12/1989 | Parisi et al. | |
| 4,909,249 A | | 3/1990 | Akkas et al. | |
| 4,919,129 A | | 4/1990 | Weber, Jr. et al. | |
| 4,932,935 A | | 6/1990 | Swartz | |
| 4,938,743 A | | 7/1990 | Lee | |
| 4,940,468 A | | 7/1990 | Petillo | |
| 4,986,827 A | | 1/1991 | Akkas et al. | |
| 5,024,652 A | | 6/1991 | Dumenek et al. | |
| 5,106,364 A | | 4/1992 | Hayafuji et al. | |
| 5,112,302 A | | 5/1992 | Cucin | |
| 5,186,714 A | | 2/1993 | Boudreault et al. | |
| 5,236,414 A | | 8/1993 | Takasu | |
| 5,249,121 A | * | 9/1993 | Baum et al. | 606/1 |
| 5,277,696 A | | 1/1994 | Hagen | |
| 5,290,282 A | | 3/1994 | Casscells | |
| 5,295,955 A | | 3/1994 | Rosen et al. | |
| 5,352,194 A | | 10/1994 | Greco et al. | |
| 5,364,395 A | | 11/1994 | West, Jr. | |
| 5,368,595 A | * | 11/1994 | Lewis | 606/72 |
| 5,514,086 A | | 5/1996 | Parisi et al. | |
| 5,520,685 A | | 5/1996 | Wojciechowicz | |
| 5,562,503 A | | 10/1996 | Ellman et al. | |
| 5,643,198 A | | 7/1997 | Cucin | |
| 5,795,323 A | | 8/1998 | Cucin | |

| | | | |
|---|---|---|---|
| 5,797,907 | A | 8/1998 | Clement |
| 5,810,809 | A | 9/1998 | Rydell |
| 5,911,700 | A | 6/1999 | Mozsary et al. |
| 5,954,686 | A | 9/1999 | Garito et al. |
| 6,102,885 | A | 8/2000 | Bass |
| 6,210,409 | B1 | 4/2001 | Ellman et al. |
| 6,231,571 | B1 | 5/2001 | Ellman et al. |
| 6,238,388 | B1 | 5/2001 | Ellman et al. |
| 6,238,394 | B1 | 5/2001 | Garito et al. |
| 6,293,944 | B1 | 9/2001 | Ellman et al. |
| 6,346,078 | B1 | 2/2002 | Ellman et al. |
| 6,346,107 | B1 | 2/2002 | Cucin |
| 6,352,533 | B1 | 3/2002 | Ellman |
| 6,387,093 | B1 | 5/2002 | Ellman et al. |
| 6,394,973 | B1 | 5/2002 | Cucin |
| 6,395,002 | B1 | 5/2002 | Ellman et al. |
| 6,432,105 | B1 | 8/2002 | Ellman et al. |
| 6,447,510 | B1 | 9/2002 | Ellman et al. |
| 6,652,522 | B2 | 11/2003 | Cucin |

FOREIGN PATENT DOCUMENTS

| | | |
|---|---|---|
| EP | 0 125 070 A2 | 11/1984 |
| FR | 2 648 050 | 12/1990 |

OTHER PUBLICATIONS

Body Contouring with Suction Lipectomy by Kesselring, Clinics in Plastic Surgery, vol. 11, No. 3, 1984.
Illouz's Technique of Body Contouring by Lipolysis by Illouz, Clinics in Plastic Surgery, vol. 11, No. 3, 1984.
European Search Report, 1995.

* cited by examiner

*Primary Examiner*—Michele Kidwell
(74) *Attorney, Agent, or Firm*—Thomas J. Perkowski, Esq., P.C.

(57) ABSTRACT

A method and apparatus is disclosed for mechanically-assisted liposuction treatment. The apparatus includes a hand-holdable housing, an electro-cauterizing dual cannula assembly, and a reciprocation mechanism. The hand-holdable housing has a cavity adaptable for receipt of the electro-cauterizing cannula assembly. The electro-cauterizing cannula assembly has a distal end and a proximal end and at least one aspiration aperture about the distal end. The reciprocation mechanism is disposed within the housing and is operably associated with the inner cannula so that the inner cannula can be selectively caused to reciprocate relative to the stationary outer cannula mounted to the hand-supportable housing. As the inner cannula is caused to reciprocate relative to the housing, the aspiration aperture formed through the distal end of the cannula assembly is caused to undergo periodic displacement. During aspiration of tissue, high-voltage RF power signal supplied to electro-cauterizing electrode structures formed about each reciprocating aspiration aperture to effect hemostasis thereabout. Such hemostasis is achieved by causing protein molecules within aspirated tissue to coagulate in response to the high-voltage RF signal being supplied across the electro-cauterizing electrode. In the preferred embodiments, the amount and rate of such aspiration aperture displacement is controllably adjustable. The cannula assembly is releasably detachable from the hand-holdable housing to facilitate cleaning and sterilization of the cannula assembly and the housing.

14 Claims, 74 Drawing Sheets

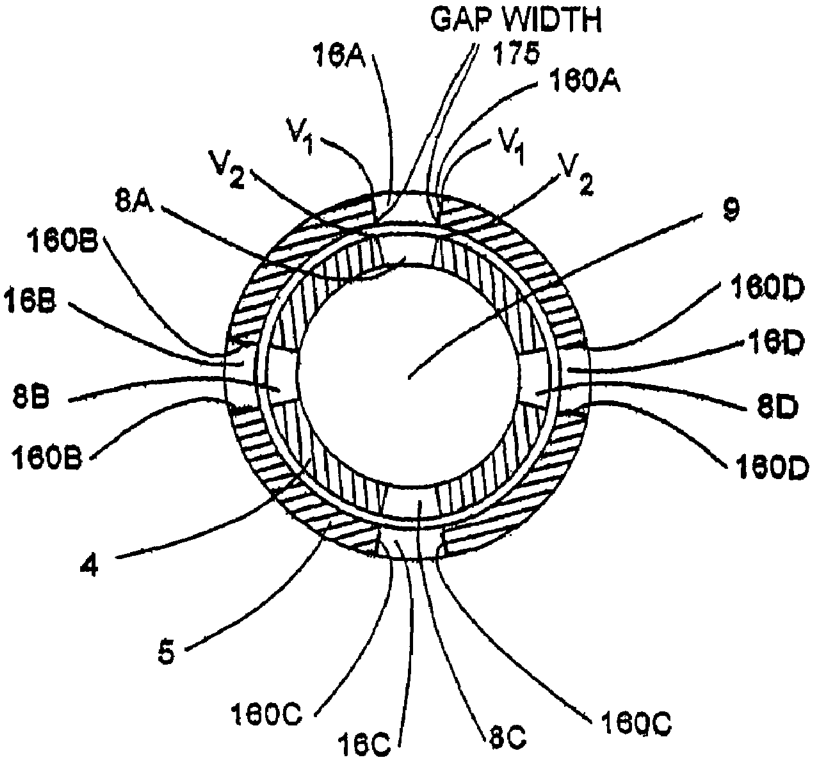
FIG. 2E
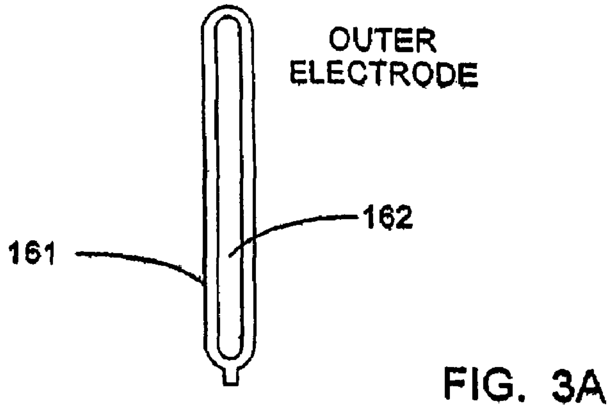
FIG. 3A
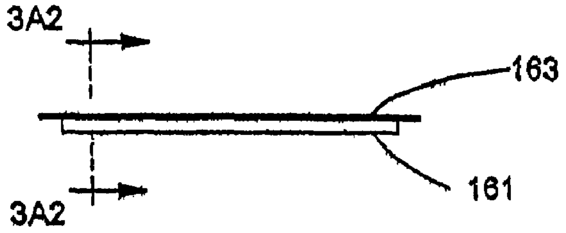
FIG. 3A1
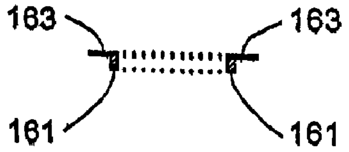
FIG. 3A2

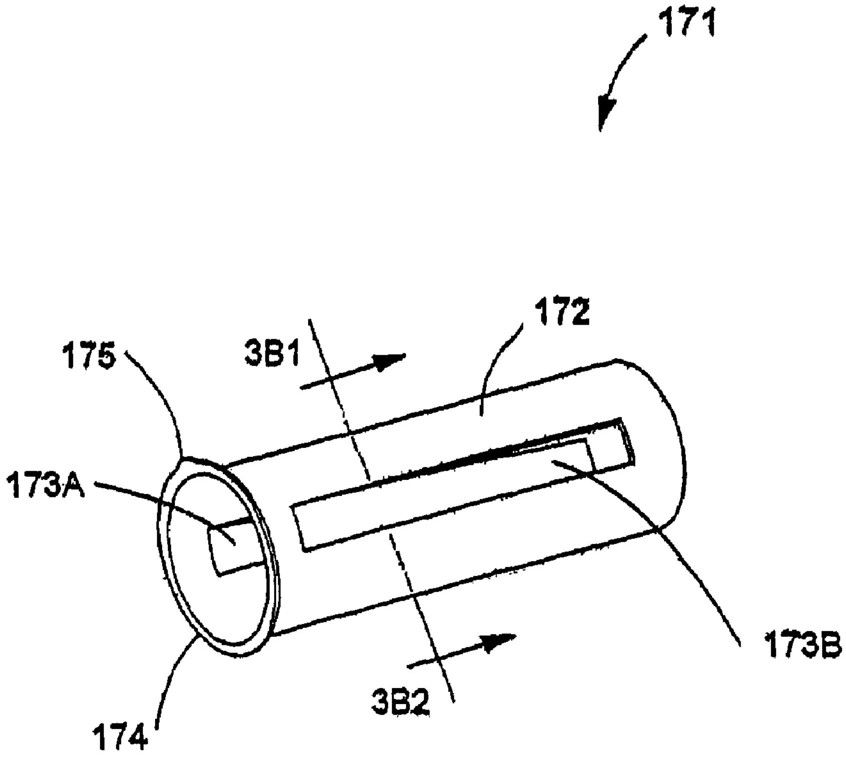
FIG. 3B
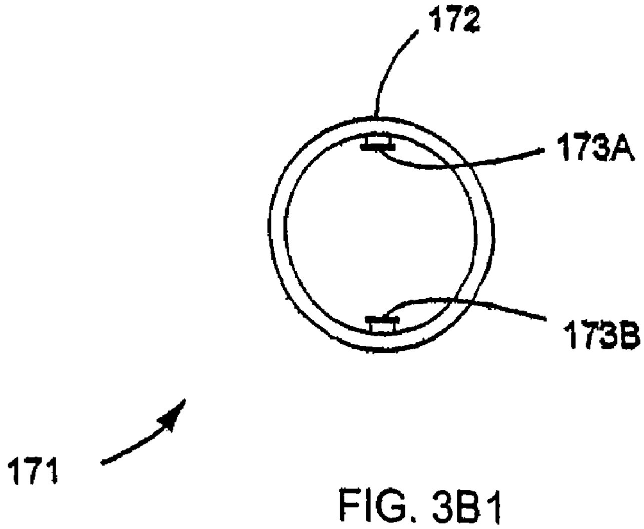
FIG. 3B1

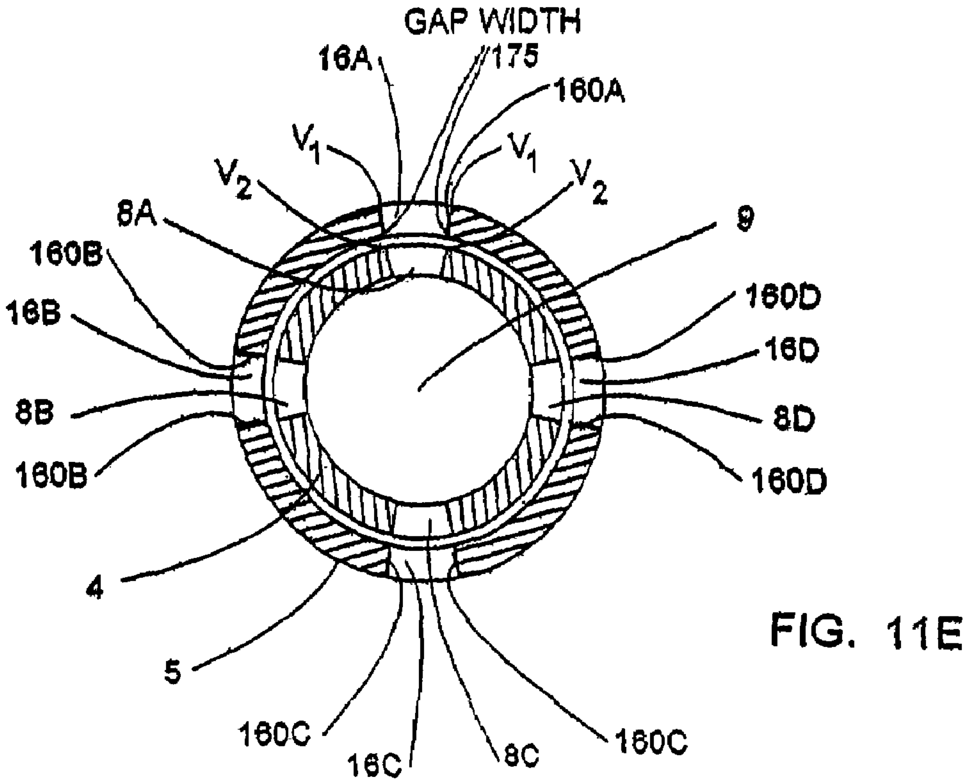
FIG. 11E
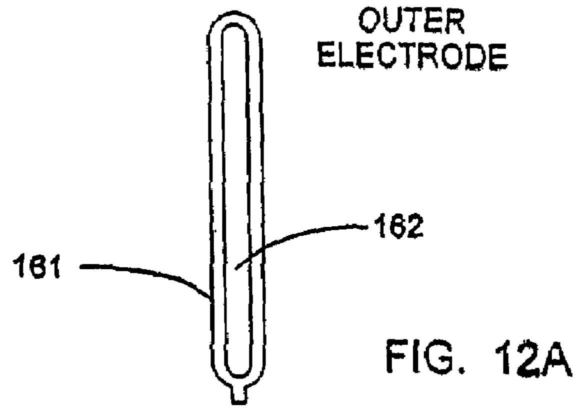
FIG. 12A
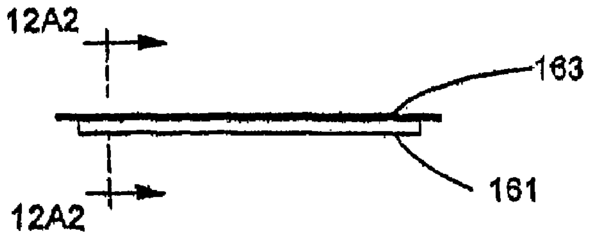
FIG. 12A1
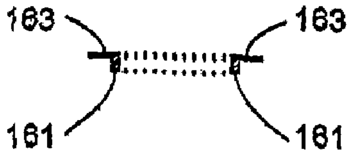
FIG. 12A2

LH

RH 452
420
450
451

25C
452
420
450
451
25C 25D
25D
420
450
451

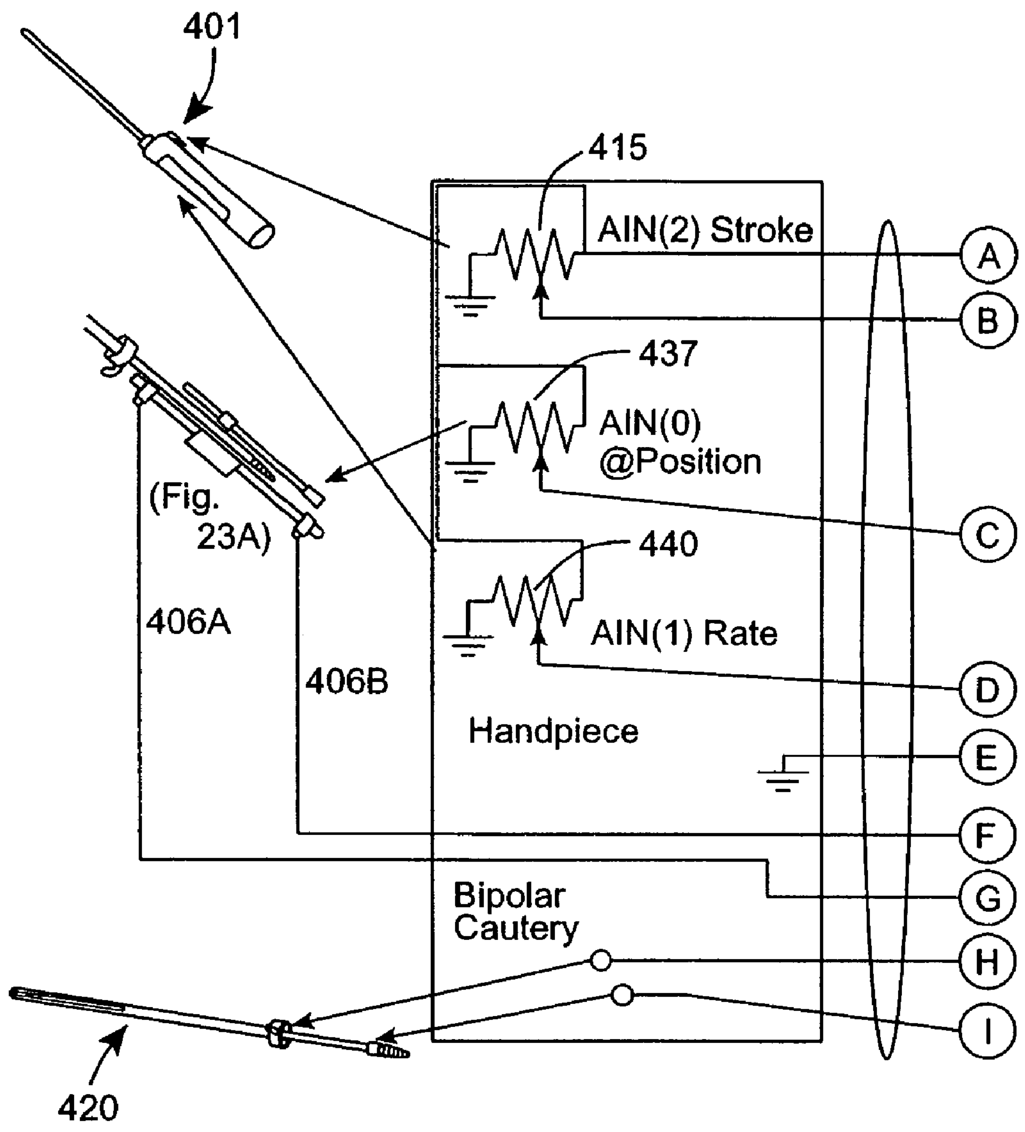
FIG. 28A1

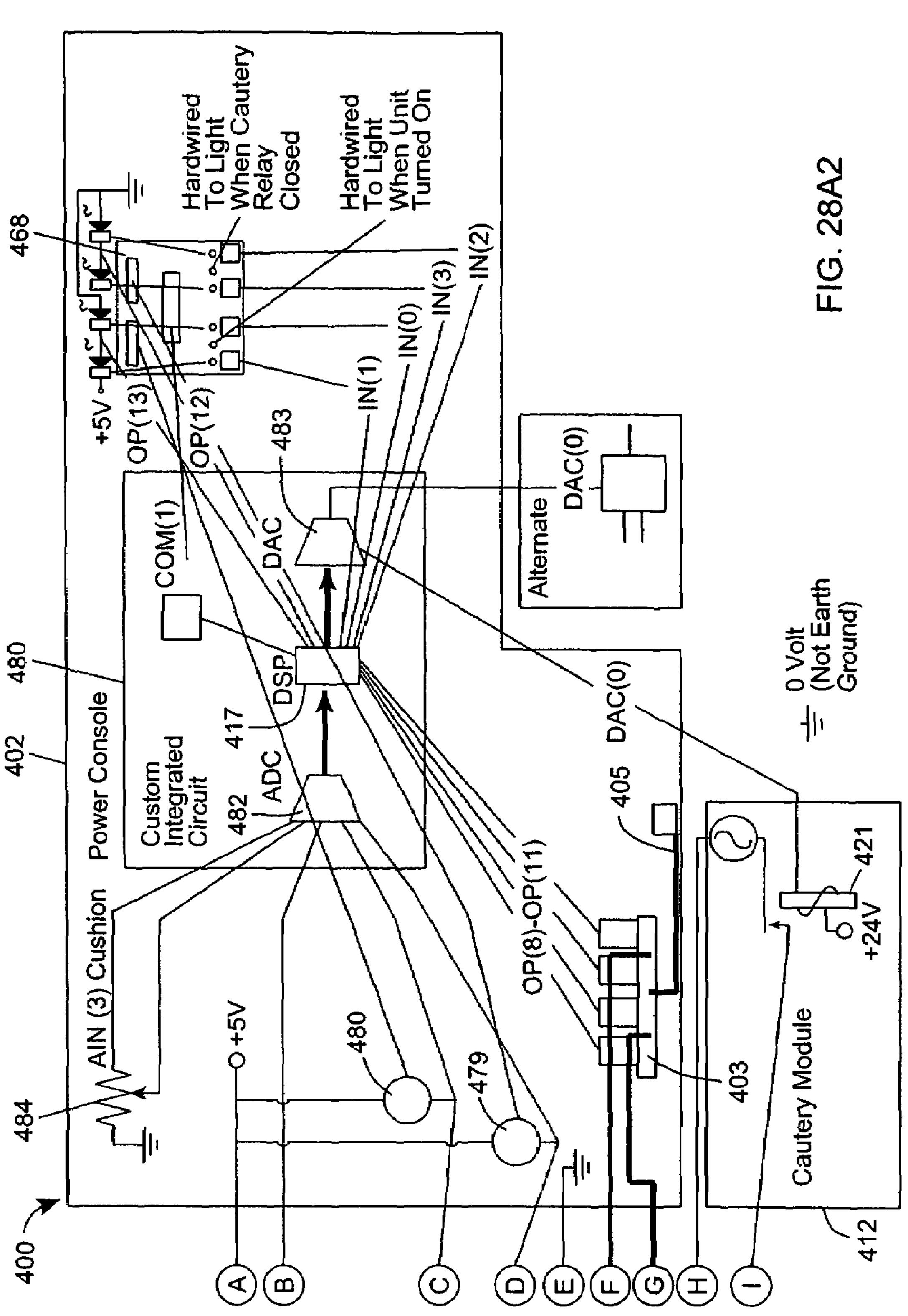
FIG. 28A2

```
'Program: Airbrush Version 4.1.0
'modules: (3) reciprocate.bas, analog.bas, scale
'ranged flex pot, sp-2 board, cautery
'current module: reciprocate.bas
'Receives unscaled inputs, VR(0) -VR(4), from analog.bas
'Receives calculated inputs, VR(5) -VR(8), from scale. bas
'Receives dummy variables, VR(9) -VR(12), from analog.bas
'GLOBAL VARIABLES --NEW
'VR(0) @position, 0-979
'VR(l) unscaled desired rate, 0-1077
'VR(2) unscaled desired stroke_length, 0-1077
'VR(3) unscaled desired cushion, 0-1077
'VR(4) on/off integer, logic check in analog
'VR(5) rate_delay, calculated by scale
'VR(6) stroke_length.
'VR(7) stroke_time, calculated by scale
'VR(8) open, calculated by scale
'VR(9) logic check for moving
'VR(10) on/off integer for wishes cautery
'VR(11) on/off integer for enable cautery
'VR(12) on/off integer for enable centimeters
'VR(13) ranged, unscaled rate (250/750)
'OUTPUT used: 8,9,10,11,12,13 and temp 14,15,16
' 8 -vents LEFT side exhaust valve
' 9 -pressurizes LEFT side valve
' 10 -Pressurize RIGHT side valve
' 11 -vents RIGHT side exhaust valve
' 12 -switch on centimeter LED
' 13 -switch on cautery enabled LED
```

```
'INITIALIZE
OP(0)

attention:

'launch programs to read pot and scale vars
IF PROC_STATUS PROC(2)=0 THEN
     RUN "analog",2
ENDIF
IF PROC_STATUS PROC(1)=0 THEN
     RUN "scale",1
ENDIF


'position cylinder at home
OP(9,0) 'depressurize LEFT valve
OP(10,0) 'depressurize RIGHT valve
OP(8,1) 'bleed LEFT cylinder
OP(11,I) 'bleed RIGHT cylinder
OP(11,0) 'close RIGHT exhaust
OP(10,1) 'pressurize RIGHT valve
WAIT UNTIL VR(0)<=90
OP(10,0) 'lock it in home position
OP(8,0)

'show_state on LED's
   IF VR(12) = 0 THEN 'wants inches
     OP(12,0) 'default LED of totem pair
   ELSE
     OP(12,1) 'switch on other totem LED with custom board
   ENDIF

IF VR(10) = 0 THEN 'does not wish cautery
    OP(13,0) 'default totem LED (sink)
  ELSE
OP(13,1) 'switch on other totem LED
  ENDIF

'wait for nonzero stroke and rate
WAIT UNTIL VR(4)=1
```

```
reciprocation_loop:

'test_on 'assure not turned off
IF VR(4)=0 THEN 'assure turned on
   GOTO attention
ELSE
   GOTO rate_delay
ENDIF

'update state on LED's
   IF VR(12) = 0 THEN 'wants inches
      OP(12,0) 'default led of totem pair (sink)
   ELSE
      OP(12,1) 'switch on other totem LED
   ENDIF

IF VR(10) = 0 THEN 'does not wish cautery
     OP(13,0) 'default LED of totem pair (sink)
   ELSE
     OP(13,1) 'switch on other totem LED
   ENDIF

rate_delay: 'to stroke at desired speed
  WA(VR(5))

'enable cautery if appropriate
   IF VR(11)=1 THEN
     WDOG=ON 'voltage normally closing DAC enabling relay
ELSE
      WDOG=OFF 'open cautery relay
ENDIF
```

B1

```
'backstroke
OP(10,0) 'depressurize RIGHT
OP(I1,I) 'open RIGHT exhaust
OP(8,0) 'close LEFT exhaust
OP(9,1) 'pressurize LEFT
```

FIG. 31C

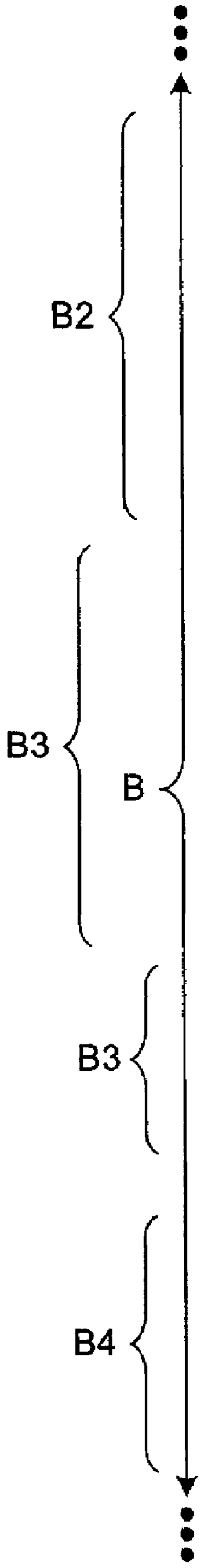

```
'cushion_back
  IF VR(3) <= 0 THEN
     GOTO test_stroke
  ELSE
      IF VR(6) <= 960 THEN 'skip short strokes
           GOTO test_stroke
      ELSE
          WA(VR(8))
          OP(11,0)
      ENDIF
   ENDIF

test_stroke: 'obtain desired stroke length
  TICKS = 300
compare:
   IF VR(0) >= VR(6) - 25 THEN
      GOTO return_stroke
   ENDIF
   IF TICKS <=0 THEN
      GOTO return_stroke 'give up
   ELSE
      GOTO compare
   ENDIF

return_stroke: 'bring home
  OP(9,0) 'depressurize LEFT
  OP(8,1) 'vent LEFT exhaust
  OP(11,0) 'close RIGHT exhaust
  OP(10,1) 'pressure RIGHT

'cushion_front
 IF VR(3) <= 0 THEN
     GOTO test_home
 ELSE
      WA(VR(8))
      OP(8,0)
 ENDIF
```

FIG. 31D

```
        •
        •
        •
      test_home:
          TICKS=400
      compare2: 'counter tendency of carriage to migrate right
        IF VR(0) <= 10 THEN
              GOTO check_running
B5      ENDIF
        IF TICKS >= 0 THEN
              GOTO compare2
        ELSE
              GOTO check_running
        ENDIF

      'Check analog is running
      check_running:
      IF PROC_STATUS PROC(2)=0 THEN
          RUN "analog", 2
B6    ENDIF

      IF PROC_STATUS PROC(1)=0 THEN
          RUN "scale", 1
      ENDIF

      GOTO reciprocation_loop 'repeat

      'loop_exit:
      'vent cylinders
C1    OP(9,0)
      OP(10,0)
      OP(8,0)
      OP(11,0)

      'kill threads
      IF PROC_STATUS PROC(2)=1 THEN
          STOP "analog"
      ENDIF
C2
      IF PROC_STATUS PROC(1)=1 THEN
          STOP "scale"
      ENDIF

      HALT
```

FIG. 31E

```
'Program: Airbrush Version 4.1.0
'modules: (3) reciprocate.bas, analog.bas, scale.bas
'ranged flex pot, sp-2 board, cautery
'current module: analog.bas

'Reads the analog inputs, eliminates noise
'and passes them to scale.bas as VR(0) -VR(4)

'GLOBAL VARIABLES
'VR(0) @position, 0-979
'VR(l) unscaled desired rate, 0-1077
'VR(2) unscaled desired stroke_length, 0-1077
'VR(3) unscaled desired cushion, 0-1077
'VR(4) on/off integer, logic check in analog
'VR(5) rate_delay, calculated by scale
'VR(6) stroke_length
'VR(7) stroke_time, calculated by scale
'VR(8) open, calculated by scale
'VR(9) on/off integer for moving
'VR(10) on/off integer for wishes cautery
'VR(11) on/off integer for enable cautery
'VR(12) on/off integer for enable centimeters
'VR(13) ranged, unscaled desired rate (250/750)
```

A1

```
'initialize used GLOBAL VARIABLES
 VR(0)= 0 'start clean
 VR(l)= 0 'rate = 0
 VR(2)= 0 'stroke = 0
 VR(3)= 0 'cushion = 0
 VR(4)= 0 'logic check for on/off
 VR(9)= 0 'logic check for moving
 VR(10)= 0 'wishes no cautery by default
 VR(11)= 0 'cautery disable by default
 VR(12) = 0 'inches by default
 VR(13) = 0 'range rate = 0
```

A2

```
'initialize LOCAL VARIABLES
 last_position=0
   moving=0
```

B

```
update: 'eliminate noise while getting instrument feedback
 VR(0) = ABS(AIN(0)) '@position
 VR(1) = ABS(AIN(1)) 'desired rate
 VR(2) = ABS(AIN(2)) 'unscaled desired stroke_length
 VR(3) = ABS(AIN(3)) 'unscaled desired cushion left
```

FIG. 32A (Analog)

C

```
'range flex pot
  IF VR(1) < 250 THEN 'set off
    VR(13) = 0
  ELSE
     IF VR(1) > 250 AND VR(1) < 750 THEN
        VR(13) = VR(1)
     ENDIF
     IF VR(1) >750 THEN 'set high
        VR(13) = 1077
     ENDIF
ENDIF
```

D

```
'logic check to make still turned on
    IF VR(13) > 0 AND VR(2) >= 25 THEN
         VR(4)=1 'neither rate nor stroke = 0
    ELSE
         VR(4)=0
    ENDIF
```

E

```
'logic check to make sure not stationary
    IF VR(0)=last_position THEN
         moving=0
    ELSE
         moving=1 'not stationary since last clock cycle
    ENDIF
```

F

```
'remember present position for next loop comparison
    last_position=VR(0)
```

G

```
'logic check for cautery
    IF VR(4)=1 AND moving=I THEN
         VR(9)=1
    ELSE
         VR(9)=0
    ENDIF
```

H

```
'check to see if cautery wish changing, read pads
    IF IN(2)=ON THEN
          VR(10)=0
    ELSE
       IF IN(3)=ON THEN
         VR(10)=1
      ENDIF
    ENDIF
```

FIG. 32B

```
I
'test if OK to enable cautery
   IF VR(9) = 1 AND VR(10) = 1 THEN
      VR(11) = 1 'enable
   ELSE
      VR(11) = 0
   ENDIF

J
'check to see if unit preference changing, read pads
   IF IN(0)=ON THEN
      VR(12)=0
   ELSE
      IF IN(I)=ON THEN
         VR(12)=1
      ENDIF
   ENDIF

K
'die if main halted
IF PROC_STATUS PROC(3)=0 THEN
      STOP "analog"
ENDIF

GOTO update
HALT
```

FIG. 32C

```
'Program: Airbrush Version 4.1.0
'modules: (3) reciprocate.bas, analog.bas, scale.bas
'ranged flex pot, sp-2 board, cautery
'current module: scale.bas

'Receives values of VR(0)- VR(4), VR(10) -VR(12) from analog.bas
'Calculates values of VR(5) -VR(11) and passes them to reciprocate. bas

'GLOBAL VARIABLES
'VR(0) @position, 0-979
'VR(1) unscaled desired rate, 0-1077
'VR(2) unscaled desired stroke_length, 0-1077
'VR(3) unscaled desired cushion, 0-1077
'VR(4) on/off integer, logic check in analog
'VR(5) rate_delay, calculated by scale
'VR(6) stroke_length
'VR(7) stroke_time, calculated by scale
'VR(8) open, calculated by scale
'VR(9) on/off integer for moving
'VR(10) on/off integer for wishes cautery
'VR(11) on/off integer for enable cautery
'VR(12) on/off integer for enable centimeters
'VR(13) ranged, unscaled rate (250/750)

'LOCAL VARIABLES
'rate_delay
'stroke_length
'stroke_time
'open

      'Initialize used GLOBAL VARIABLES
      VR(5) = 0
A1    VR(6) = 0
      VR(7) = 0
      VR(8) = 0

      'Initialize LOCAL VARIABLES
      rate_delay = 0
      stroke_length= 0
A2    stroke_time=0
      open = 0
      rate = 0
      cushion = 0
```

FIG. 33A (Scale)

```
last_vr_13=0
last_vr_2=0

     scale:
       IF last_vr_13=INT(VR(13)) AND last_vr_2=INT(VR(2)) THEN
             GOTO skipped
       ELSE
         'com1 panel DISPLAY
            SETCOM(9600,8,1,2,1)  'setup PORT1 'for custom trio board
            PRINT#1, "RATE (cpm) = ", INT(VR(13))*120/1077)-1 [0] 'custom board
B1        'com0 terminal
            PRINT#0, "RATE (cpm) =     ", INT(VR(13))*120/1077)-1 [0] 'terminal 0
          IF VR(12)=1 THEN
          'com1(DISPLAY)
            PRINT#1, "STROKE (cm.) = ", INT(VR(2))*10/1077)-[1] 'custom board
          'com0 (terminal)
            'PRINT#0, "STROKE (cm.) =   ", INT(VR(2)*10/1077) [1] 'terminal 0
          ELSE
               'PRINT#0, "STROKE (in.) =  ", INT(VR(2)*10/(1077*2.54)) [1]
     'terminal
               PRINT#1, "STROKE (in.) =  ",  INT(VR(2)*10/(1077*2.54)) [1] 'display
B2        ENDIF
          last_vr_13=INT(VR(13))
          last_vr_2=INT(VR(2))
     ENDIF

     skipped:
       stroke_length = VR(2) * C1
       rate = VR(13)/C2 + C3
       cushion = VR(3)/C4 * C5
       cycle_time = C6/rate
       stroke_time = stroke_length * C7 + C8 *rate 'linear travel speed =
      f(P)
B3     rate_delay = cycle_time * C9 - stroke_time
               IF rate_delay > 2000 THEN 'maximum 2 secs
                   Rate_delay = 2000
               ENDIF
       open = stroke_time - cushion
               IF open < 0.50 * stroke_time THEN
                    Open = 0.50 * stroke_time
       ENDIF

     'assign
C     VR(5) = rate_delay
      VR(6) = stroke_length
      VR(7) = stroke_time
```

FIG. 33B

```
  •
  •
  •
     VR(8) = open

D   'die if main halted
    IF PROC_STATUS PROC(3)=0 THEN
        STOP "scale"
    ENDIF

E   'ensure readings are fresh
    IF PROC_STATUS PROC(2)=0 THEN
        RUN "analog",2
    ENDIF

F   'recalculate
    GOTO scale

    HALT
```

FIG. 33C

Cautery Control Process

| Pin Number | Connection | Comment | |
|---|---|---|---|
| 1 | Earth Ground ⏚ | Shielding | (Green/Yellow Stripe) |
| 2 | 0v | Black | |
| 3 | @Position Wiper | AIN(0) | Blue |
| 4 | Rate Flex Pot Wiper | AIN(1) | Yellow |
| 5 | Stroke Pot Wiper | AIN(2) | Orange |
| 6 | +5v | Red | |
| 7 | RF1 | Red | |
| 8 | RF2 | White | |

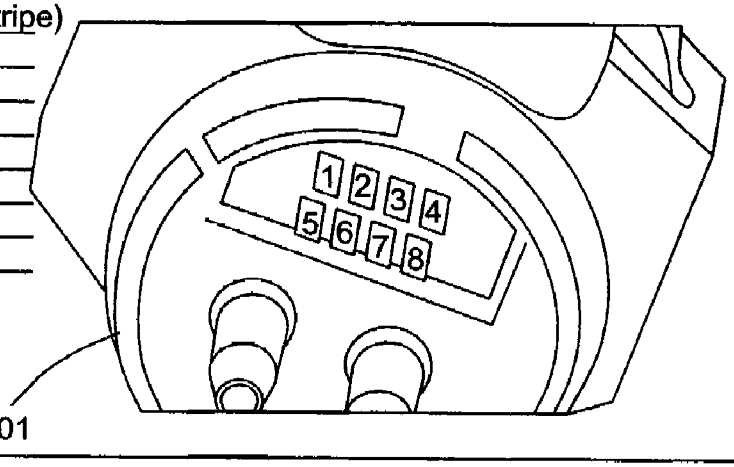

Pin-out For LEMO to ESU:
(1) Earth Ground ⏚
(2) Controller 0v
(3) @Position (Wiper)
(4) Rate Wiper
(5) RF Signal Circuit 0v
(6) RF Signal Circuit Vcc IO's Analog:

AIN(0) @Position (Wiper)
AIN(1) Rate (Wiper)
AIN(2) Stroke (Wiper)
AIN(3) Cushion (Wiper)

DAC(0) Cautery Enable
(Used All/None - Digital)

Digital:

IN(0) Display Inches (Default)
IN(1) Display Centimeters
IN(2) Display Cautery (Default)
IN(3) Enable Cautery OP(8) Vent L (FRONT) Cylinder
OP(9) Pressurize L Cylinder
OP(10) Pressure R (BACK) Cylinder
OP(11) Vent R Cylinder OP(12) Cautery Enable (Sinks Off)
OP(13) Centimeters Preferred (Sinks Off)

FIG. 38C

POWER-ASSISTED TISSUE-ASPIRATION INSTRUMENT SYSTEM EMPLOYING AN ELECTRONICALLY-CONTROLLED AIR-FLOW VALVE ASSEMBLY WITHIN AN EXTERNAL INSTRUMENT CONTROLLER

RELATED CASES

The present Application is a Continuation of copending application Ser. No. 10/442,645 filed May 21, 2003; which is a Continuation-in-Part of: application Ser. No. 09/507,266 filed Feb. 18, 2000, now U.S. Pat. No. 6,394,973 B1; which is a Continuation-in-Part of application Ser. No. 08/882,927 filed Jun. 26, 1997 now U.S. Pat. No. 5,795,323, which is a Continuation of application Ser. No. 08/307,000 filed Sep. 16, 1994, now U.S. Pat. No. 5,643,198, which is a Continuation of application Ser. No. 07/627,240 filed Dec. 14, 1990, now U.S. Pat. No. 5,348,535; each said Application being incorporated herein by reference as if set forth in its entirety.

BACKGROUND OF THE INVENTION

1. Field of Invention

The present invention relates generally to a method and apparatus for performing liposuction, and more particularly to a method and apparatus for performing liposuction in a mechanically assisted manner using powered expedients.

2. Brief Description of the Prior Art

Suction lipectomy, commonly known as liposuction or lipoxheresis, is a well known surgical procedure used for sculpturing or contouring the human body to increase the attractiveness of its form. In general, the procedure involves the use of a special type of curet known as a cannula, which is operably connected to a vacuum source. The cannula is inserted within a region of fatty tissue where removal thereof is desired, and the vacuum source suctions the fatty tissue through the suction aperture in the cannula and carries the aspirated fat away. Removal of fat cells by liposuction creates a desired contour that will retain its form.

Presently, there are two widely accepted techniques of liposuction and each may be practiced using a conventional liposuction cannula. The first and most common method proposed by Yves-Gerard Illouz and described in the paper "Illouz's Technique of Body Contouring by Lipolysis" in Vol. 3, No. 3, July 1984 of Clinics in Plastic Surgery, involves making regular tunnels at a depth of at least 1 centimeter under the skin. According to this method, one or two insertions are made, with radial excursions of the cannula into the fatty tissue of the patient. The result is a multitude of concomitant sinuses formed below the subcutaneous fatty tissue, leaving intact as far as possible the connections between the skin and underlying tissue, thereby retaining the blood vessels, the lymphatics and the nerve endings. The second method is the original liposuction procedure proposed by U. K. Kesselring, described in "Body Contouring with Suction Lipectomy," in Vol. 11, No. 3, July 1984, Clinics in Plastic Surgery. According to the technique, an entire layer of regular, deep fat is removed by aspiration through the cannula, leaving a smooth, deep surface of the residual panniculus. The space thus created is then compressed, optimally followed by skin retraction.

Both of these prior art liposuction techniques require that the surgeon push and pull the entire cannula back and forth almost twenty times for each insertion made. Typically, twenty to thirty tunnels are made. This is necessary to ensure even removal of fat in the targeted region. During this procedure, the surgeon typically massages the flesh in the area of the aperture in the cannula, while at the same time thrusting the rod in and out of the tunnel. Due to the trauma involved during the procedure, the patient's skin turns black and blue for several weeks. Due to the physically exacting nature of the procedure, the surgeon typically comes out of an operating room extremely tired and suffers from muscular fatigue which prevents him from performing, for some time thereafter, delicate operations involved in ordinary plastic surgery.

Recently, the use of a "guided cannula" has been proposed by R. de la Plaza, et al., described in "The Rationalization of Liposuction Toward a Safer and More Accurate Technique," published in vol. 13, Aesthetic Plastic Surgery, 1989. According to the technique, a cannula is used in conjunction with an outer guide sheath through which the cannula can slidably pass while held in place by the handle portion of the guide sheath. Once the cannula and its sheath have been introduced into the fatty tissue, the sheath guide remains in the tunnel and guides successive introductions of the cannula, keeping it in the same tunnel. While the use of this liposuction technique offers some advantages over the conventional unguided liposuction cannulas, the guided cannula nevertheless suffers from several significant shortcomings and drawbacks. In particular, the guided cannula requires manually thrusting the cannula through the guide sleeve repeatedly for each tunnel. Although this is a less physically demanding procedure, the surgeon must thrust the cannula even more times through each tunnel to achieve the desired effect and hence is still easily fatigued and prevented from performing, for some time thereafter, delicate operations involved in ordinary plastic surgery.

In an attempt to solve the above-described problem, U.S. Pat. Nos. 4,735,605 and 4,775,365 and 4,792,327 to Swartz disclose an assisted lipectomy cannula having an aspiration aperture which effectively travels along a portion of the length of the cannula, thereby obviating the necessity of the surgeon to repeatedly push the cannula in and out of the patient's subcutaneous tissue where fatty tissue is to be removed. While this assisted lipectomy cannula can operate on either air or electric power, it nevertheless suffers from several significant shortcomings and drawbacks. In particular, the device requires an outer tube with an elongated slot and an inner tube having a spiral slot which must be rotated inside the outer tube to effectuate a traveling aspiration aperture. In addition to the device's overall construction posing difficulties in assembly, cleaning and sterilization, use with a variety of cannulas and highly effective fat aspiration does not appear possible.

In U.S. Pat. No. 5,112,302 to Cucin, Applicant discloses a powered liposuction instrument which offers significant improvements over the instruments disclosed in US Letters Patents above. However, the powered liposuction instrument designs taught in U.S. Pat. No. 5,112,302 are not without shortcomings and drawbacks. In particular, these liposuction instrument designs employ a single cannula which is designed to reciprocate relative to the instrument housing by relatively large amounts (e.g. 1-10 centimeters). When using instruments of this prior art design, it is possible that such large scale movements of the cannula can accidently rupture tissue walls within the patient, causing complications which are best avoided by practicing surgeons at all costs.

Accordingly, there is a great need in the art for a mechanically-assisted lipectomy instrument which overcomes the shortcomings and drawbacks of prior art lipectomy apparatus.

OBJECTS AND SUMMARY OF THE PRESENT INVENTION

Thus, a primary object of the present invention is to provide an improved method and apparatus for performing liposuction which assists the surgeon in the removal of fat and other subcutaneous tissue (such as but not restricted to gynecomastia, ______) from surrounding tissue, with increased control, patient-safety, and without promoting physical fatigue.

Another object of the present invention is to provide such apparatus in the form of a hand-holdable liposuction instrument having a cannula assembly, in which the location of the aspiration aperture is periodically displaced as the inner or outer cannula undergoes sliding movement relative to the hand-holdable housing.

Another object is to provide such a liposuction instrument in which the rate of reciprocation and the amount of excursion of the aspiration aperture, are selectively adjustable by the surgeon during the course of operation.

Another object the present invention is to provide such a liposuction instrument which can be driven by air or electricity.

A further object of the present invention is to provide such a liposuction instrument, in which the cannula assembly can be simply detached from the hand-holdable housing for ease of replacement and/or sterilization.

An even further object of the present invention is to provide an improved method of performing liposuction, in which one of the cannulas of the cannula assembly is automatically reciprocated back and forth relative to the hand-holdable housing, to permit increased control over the area of subcutaneous tissue where fatty and other soft tissue is to be aspirated.

Another object of the present invention is to provide a power-assisted liposuction instrument, wherein means are provided along the cannula assembly to effecting hemostasis during liposuction procedures and the like.

Another object of the present invention is to provide such power-assisted liposuction instrument, wherein the hemostasis means is realized using RF-based electro-cauterization.

Another object of the present invention is to provide such a power-assisted liposuction instrument, wherein RF-based electro-cauterization is carried out by providing electro-cauterizing electrodes along the cannula assembly and supplying to these electrodes, a RF signal of sufficient power to achieve electro-coagulation and thus hemostasis during liposuction procedures.

Another object of the present invention is to provide such a power-assisted liposuction instrument, wherein the outer cannula is realized from a non-conductive material and electro-cauterizing electrode elements are inserted within the aspiration apertures thereof and electrical wiring embedded along the outer cannula and connected to a contact pad embedded within the base portion thereof, and wherein the inner cannula is made from an electrically conductive material which establishes electrical contact with contact brushes mounted within the central bore of the base portion of the inner cannula.

Another object of the present invention is to provide such a power-assisted liposuction instrument, wherein RF supply and return signals are coupled to the cannula assembly by way of the base portion of the outer cannula.

Another object of the present invention is to provide a power-assisted liposuction instrument, wherein RF-based electro-cauterization is realized using electrically conductive inner and outer cannulas which are electrically isolated by way of thin Teflon coatings applied to the outer surface of the inner cannula and/or the interior surface of the outer cannula.

Another object of the present invention is to provide a power-assisted liposuction instrument, wherein ultrasonic energy of about 40 kHz is coupled to the inner cannula in order to effect protein coagulation about the aspiration apertures and thus achieve electro-cauterization (is hemostasis) during liposuction procedures.

Another object of the present invention is to provide such a power-assisted liposuction instrument, wherein such ultrasonic energy is produced by piezoelectric crystals embedded within the base portion of the inner cannula and driven by electrical signals having a frequency of about 50 kHz.

Another object of the present invention is to provide such a liposuction instrument, wherein the electrical drive signals are supplied to the piezoelectric transducers by way of a pair of electrically conductive rails embedded within the interior surface of the cannula cavity of the hand-holdable housing of the liposuction device.

Another object of the present invention is to provide a way of carrying out RF-based cauterization within a cannula assembly, wherein the operating surgeon is enabled to perform lipolysis by driving the piezo-electric transducers within the base portion of the inner cannula with signals in the frequency range of about 20-25 kHz.

Another object of the present invention is to provide an air-powered tissue-aspiration (e.g., liposuction) instrument system, wherein the powered liposuction instrument has an inner cannula that is automatically reciprocated within a stationary outer cannula by electronically controlling the flow of pressurized air streams within a dual-port pressurized air cylinder supported within the hand-supportable housing of the instrument.

Another object of the present invention is to provide such an air-powered liposuction instrument system, wherein digital electronic control signals are generated within an instrument controller unit and these control signals are used to generate a pair of pressurized air streams within the instrument controller which are then supplied to opposite ends of the dual-port pressurized air cylinder within the powered liposuction instrument.

Another object of the present invention is to provide such an air-powered liposuction instrument system, wherein the rear end of the powered liposuction instrument has a pressurized air-power supply-line connector, an electrical control signal connector, an RF power signal connector, and a tissue-aspirating tubing port.

Another object of the present invention is to provide such an air-powered liposuction instrument system, wherein the front end of the powered liposuction instrument supports an electro-cauterizing dual-cannula assembly releasably connected thereto.

Another object of the present invention is to provide such an air-powered liposuction instrument system, wherein the powered liposuction instrument has a hinged door panel that can be arranged in an open configuration so as to simply install the electro-cauterizing cannula assembly and connect the aspiration tubing thereto.

Another object of the present invention is to provide such an air-powered liposuction instrument system, wherein a hinged spring-biased door panel is provided for controlling the rate of reciprocation of the inner cannula.

Another object of the present invention is to provide such an air-powered liposuction instrument system, wherein the maximum rate of cannula reciprocation is achieved when the hinged spring-biased door panel is manually depressed its maximum amount.

Another object of the present invention is to provide such an air-powered liposuction instrument system, wherein a dual-port air-cylinder is arranged within a hand-supportable housing, in operable association with an inner cannula actuator position sensing transducer, for measuring the instantaneous stroke position of the inner cannula during reciprocation operations.

Another object of the present invention is to provide such an air-powered liposuction instrument system, wherein the base portion of the inner cannula is releasably locked within the a first recess of the carriage portion of the inner cannula actuator and wherein the inner cannula actuator is mounted to a block that is magnetically coupled to the piston within the dual-port air cylinder structure, and wherein the slidable wiper of the actuator position sensing transducer is mounted within a second recess of the carriage portion of the inner cannula actuator.

Another object of the present invention is to provide such an air-powered liposuction instrument system, wherein a cannula reciprocation stroke control switch is mounted on the hand-supportable housing of the instrument for operation by the surgeon's thumb, whereas the cannula reciprocation rate control switch is realized using a flexible potentiometer that is deformed upon the surgeon squeezing a spring-biased hinged door panel provided on the instrument housing.

Another object of the present invention is to provide such an air-powered tissue-aspiration instrument system which comprises: (1) a hand-held air-powered tissue-aspirating instrument adapted for use with a bipolar electro-cauterizing dual cannula assembly, and (2) a stand-alone control console adapted for (i) receiving a source of pressurized air from an external air source, and (ii) generating a controlled stream of pressurized air that is supplied to said hand-held instrument, and also for (iii) receiving RF signals generated from an external (or internal) RF signal generation and supply module and (iv) supplying the received RF signals to said electrode structures within the bipolar electro-cauterizing dual cannula assembly, via said stand-alone control console, during the use of the system in performing tissue aspiration (e.g. liposuction) procedures.

Another object of the present invention is to provide such an air-powered tissue-aspiration instrument system, wherein an intelligent instrument controller (i.e. control unit) is used to supply air-power to the inner cannula reciprocation mechanism within the hand-supportable instrument, and RF power to its electro-cauterizing cannula assembly, while communicating control signals between the instrument and its intelligent controller.

Another object of the present invention is to provide such an air-powered tissue-aspiration instrument system, wherein its instrument controller comprises: an user control console having (i) a plurality of membrane type switches for selecting a desired cannula stroke length dimension (i.e. inches or centimeters) for measurement and display and for enabling and disabling electro-cautery function selection, (ii) a plurality of LED indicators for indicating Power ON/OFF function selection, cannula stroke length dimension selection, and electro-cautery enable/disable function selection, (iii) a pair of LCD-based display panels for displaying graphical (i.e., bar graph) indications of inner cannula reciprocation rate (in cycles/sec) and inner cannula position measured by the cannula position sensor mounted within the hand-supportable instrument, and (iv) a LCD-based panel for displaying measured numerical values for the instantaneous rate of reciprocation for the inner cannula and the instantaneous stroke length thereof; and a controller housing mounting a multi-core (i.e. air-supply/RF-power-signal/control-signal) connector assembly, as well as providing an input port for receiving RF power signals generated from an external RF signal source, and an input port for receiving a source of pressurized air to drive the powered instrument of the present invention.

Another object of the present invention is to provide such an air-powered tissue-aspiration instrument system, wherein (i) analog voltage input signals are generated from within the powered liposuction instrument and supplied as analog input voltage signals to the intelligent instrument controller for detection, A/D conversion and digital signal processing, (ii) digital voltage output control signals are generated within the intelligent instrument controller and supplied as output voltage signals to the powered instrument and also the air-control valve assembly within the instrument controller so as to generate the pair of pressurized air-supply streams that are supplied to the powered instrument via the multi-port connector assembly, and (iii) an analog control voltage output signal is generated within the intelligent instrument controller and supplied to the control input port of the external RF signal source (i.e. generator) to generate an RF power signal and to supply the same to the instrument controller for controlled delivery to the electro-cauterizing dual cannula assembly of the powered instrument.

Another object of the present invention is to provide such an air-powered tissue-aspiration instrument system, wherein its instrument controller comprises a digitally-controlled multi-port air-flow control valve assembly.

Another object of the present invention is to provide such an air-powered tissue-aspiration instrument system, wherein the digitally-controlled multi-port air-flow control valve assembly comprises (i) a central air-flow control port for connection to the external source of pressurized air, (ii) a left air-flow control port for connection to the left side of the air-driven cylinder within the instrument, and (iii) a right air-flow control port for connection to the right side of the air-driven cylinder within the instrument.

Another object of the present invention is to provide such an air-powered tissue-aspiration instrument system, wherein digital output control voltage signals are provided to electrically-controlled solenoid-type air-flow control valves embodied within the multi-port air-flow control valve assembly, so as to electronically control the operation of the air-pressure driven inner cannula reciprocation mechanism employed within the powered instrument of the present invention.

Another object of the present invention is to provide such an air-powered tissue-aspiration instrument system, wherein the instrument controller employs a system control program that runs on a custom-designed digital signal processor.

Another object of the present invention is to provide an air-powered tissue-aspiration instrument system, comprising (i) a hand-supportable air-powered instrument having an electro-cauterizing dual-cannula assembly and a multi-core (i.e. air-supply/RF-power/control-signal) connector assembly, and (ii) an intelligent instrument controller designed to (i) receive a pressurized air flow from an pressurized air source and RF power signals from a RF power signal generator, both external to said intelligent instrument controller, and to (ii) supply a pair of pressurized air streams and RF power signals to the hand-supportable instrument during instrument operation.

Another object of the present invention is to provide an air-powered tissue-aspiration instrument system, wherein a multi-core connector assembly is provided comprising: (i) a first multi-port connector adapted for installation in the rear end portion of the powered instrument housing as well as through the wall of the intelligent instrument controller (as the case may be) and having a pair of pressurized air-flow ports and a multi-pin electrical port for supporting the communication of RF power signals between the instrument controller and instrument and the communication of electrical control signals between the instrument controller and instrument; and (ii) a second multi-port connector plug mated to the first multi-port connector and adapted for connection to a multi-core cable structure including a pair of air-supply tubes, a pair of RF power signal wires, and a set of electrical control signal wires, all of which is encased within a flexible plastic casing.

Another object of the present invention is to provide such an air-powered tissue-aspiration instrument system, wherein the flexible aspiration tubing connected to the inner cannula is routed out through an exit port formed in the side surface of its hand-supportable housing.

Another object of the present invention is to provide such an air-powered tissue-aspiration instrument system, wherein the air-powered instrument employs a curved electro-cauterizing dual cannula assembly, in which the curved hollow outer cannula is rigidly constructed while the hollow inner cannula is made from a flexible, pliant material such as resilient medical grade plastic material or the like.

Another object of the present invention is to provide such an air-powered tissue-aspiration instrument system, wherein the inner cannula flexibly adapts to the rigid curved geometry of the outer cannula structure during instrument operation.

Another object of the present invention is to provide such an air-powered tissue-aspiration instrument system, wherein an improved bipolar-type electro-cauterizing dual cannula assembly is provided for use with the powered instruments.

Another object of the present invention is to provide such an air-powered tissue-aspiration instrument system, wherein the improved bipolar-type electro-cauterizing dual cannula assembly is comprises an electrically conductive (e.g. metal) outer cannula for releasably mounting within the hand-supportable housing of a powered instrument, and a molded or extruded plastic inner cannula for slidable support with the outer cannula and reciprocation by the actuator.

Another object of the present invention is to provide such an air-powered tissue-aspiration instrument system, wherein the non-conductive inner cannula has a fine electrically conductive wire molded within the walls thereof which terminate in an electrically conductive ring about the aspiration aperture of the inner cannula, for conducting RF power signals from the base portion of the inner cannula to the electrically-conductive ring during powered tissue aspiration operations.

Another object of the present invention is to provide such an air-powered tissue-aspiration instrument system with an alternative electro-cauterizing dual cannula assembly, wherein a stream of irrigation fluid is automatically pumped from the base portion of the outer cannula to the distal portion thereof, along a micro-sized fluid conduit formed along the surface walls of the outer cannula, and released into the interior distal portion of the outer cannula through a small opening formed therein, for infiltration and irrigation of tissue during aspiration in order to facilitate pump action.

Another object of the present invention is to provide an air-powered tissue-aspiration instrument system, wherein the inner cannula is loaded through an inner cannula loading port provided at the rear of the instrument housing, and thereafter snap-fitted into position within recess in the carriage portion of the air-powered actuator structure installed therein.

Another object of the present invention is to provide such an air-powered tissue-aspiration instrument system, wherein during such inner cannula loading operations, the outer cannula is first connected to the front portion of the hand-supportable housing, the actuator structure retracted to the rear portion of the hand-supportable housing, and then, the distal portion of the inner cannula is inserted first through the cannula loading port, and then its base portion is snap-fitted within recess in the actuator carriage.

These and other Objects of the present invention will become apparent hereinafter.

BRIEF DESCRIPTION OF THE DRAWINGS

For a fuller understanding of the objects of the present invention, reference is made to the detailed description of the illustrative embodiments which are to be taken in connection with the accompanying drawings, wherein:

FIG. 2E is a cross-sectional view of the electro-cauterizing cannula assembly taken along line 2E-2E of FIG. 2A;

FIG. 3A is a plan view of a cauterizing electrode of the present invention adapted for insertion within the elongated aperture of the electrically non-conducting outer cannula;

FIG. 3A1 is an elevated side view of the cauterizing electrode of the present invention taken along line 3A1-3A1 of FIG. 3A;

FIG. 3A2 is an elevated side view of the cauterizing electrode of the present invention taken along line 3A2-3A2 of FIG. 3A1;

FIG. 3B is a perspective view of the electrically-conductive collar and brush device of the present invention which inserts with the central bore formed in the base portion of the electrically non-conductive outer cannula of the present invention shown in FIG. 2D;

FIG. 3B1 is a cross-sectional view of the electrically-conductive collar and brush device of the present invention taken along line 3B1-3B1 of FIG. 3B;

FIG. 11E is a cross-sectional view of the electro-cauterizing cannula assembly taken along line 11E-11E of FIG. 11A;

FIG. 12A is a plan view of a cauterizing electrode of the present invention adapted for insertion within the elongated aperture of the electrically non-conducting outer cannula shown in FIG. 11;

FIG. 12A1 is an elevated side view of the cauterizing electrode of the present invention taken along line 12A1-12A1 of FIG. 12A;

FIG. 12A2 is an elevated side view of the cauterizing electrode of the present invention taken along line 12A2-12A2 of FIG. 12A1;

FIGS. 28A1 and 28A2, taken together, set forth a hybrid electrical and mechanical schematic representation of the air-powered liposuction instrument systems of FIGS. 20A and 35A, showing (i) analog voltage input signals being generated from within the powered liposuction instrument and supplied as analog input voltage signals to the instrument controller of FIG. 27A for detection, A/D conversion and digital signal processing, (ii) digital voltage output control signals generated within the instrument controller and supplied as output voltage signals to (a) the air-powered liposuction instrument and also the air-control valve assembly within the instrument controller to generate the pair of pressurized air-supply streams that are supplied to the liposuction instrument via the multi-port connector assembly, and (iii) an analog control voltage output signal generated within the instrument controller and supplied to the control input port of the external RF signal source (i.e. generator) to generate an RF power signal and to supply the same to the instrument controller for controlled delivery to the air-powered liposuction instrument;

FIG. 31A through 31E, taken together, sets forth the source code (written in Basic Language) for the primary thread program entitled RECIPROCATE to run on the custom-designed processor employed within the intelligent instrument controller schematically illustrated in FIGS. 28A1 and 28A2 and shown in FIGS. 27A and 27B;

FIG. 32A through 32C, taken together, sets forth the source code (written in Basic Language) for the secondary thread program called ANALOG to run on the custom-designed processor employed within the intelligent instrument controller shown in FIGS. 27A and 27B, and called by the primary program entitled RECIPROCATE;

FIG. 33A through 33C, taken together, sets forth the source code (written in Basic Language) for the tertiary thread program called SCALE to run on the custom-designed processor employed within the intelligent instrument controller shown in FIGS. 27A and 27B, also called by the primary program entitled RECIPROCATE;

FIGS. 38A through 38C, taken all together, set forth a hybrid electrical and mechanical schematic representation of the air-powered liposuction instrument systems of FIGS. 20A and 35A, showing (i) analog voltage input signals being generated from within the air-powered liposuction instrument and supplied as analog input voltage signals to the instrument controller for detection, A/D conversion and digital signal processing, (ii) digital voltage output control signals being generated within the instrument controller and supplied as output voltage signals to (a) the air-powered liposuction instrument via the multi-core cable structure and multi-port connector assembly of the present invention as well as to the air-control valve assembly within the instrument controller to generate the pair of pressurized air-supply streams that are supplied to the liposuction instrument via the multi-port connector assembly, and (iii) an analog control voltage output signal being generated within the instrument controller and supplied to the control input port of the external RF signal source (i.e. generator) to generate an RF power signal and to supply the same to the instrument controller for controlled delivery to the air-powered liposuction instrument via the multi-core cable structure and the multi-port connector assembly of the present invention;

FIG. 40A is an elevated side view of an alternative embodiment of the air-powered liposuction instrument of the present invention, employing a curved bi-polar type electro-cauterizing dual cannula assembly, wherein the curved hollow outer cannula is rigidly constructed while the hollow inner cannula is made from a flexible material such as resilient medical grade plastic material or the like;

Figure 42:
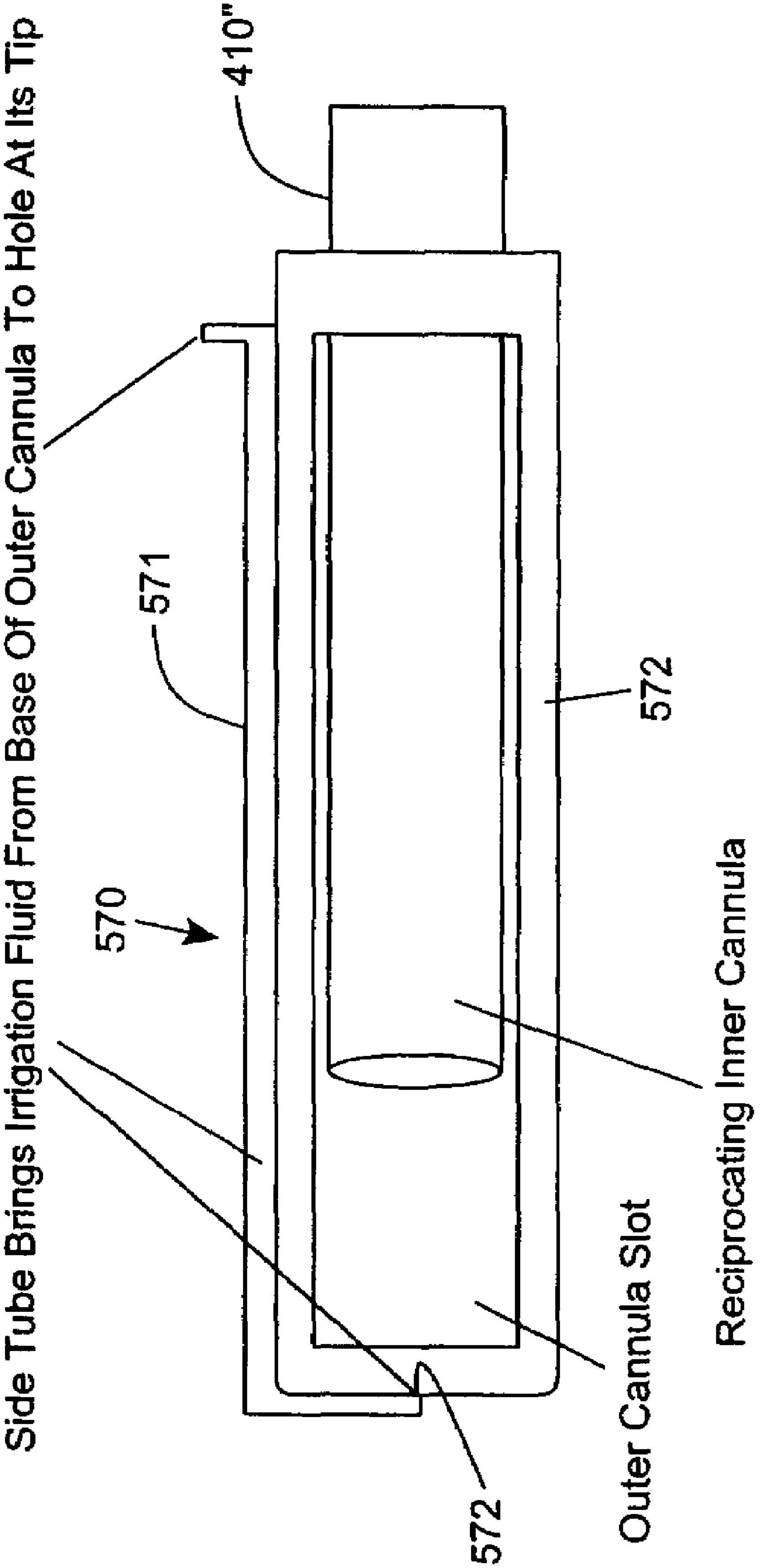
Figure 43A:
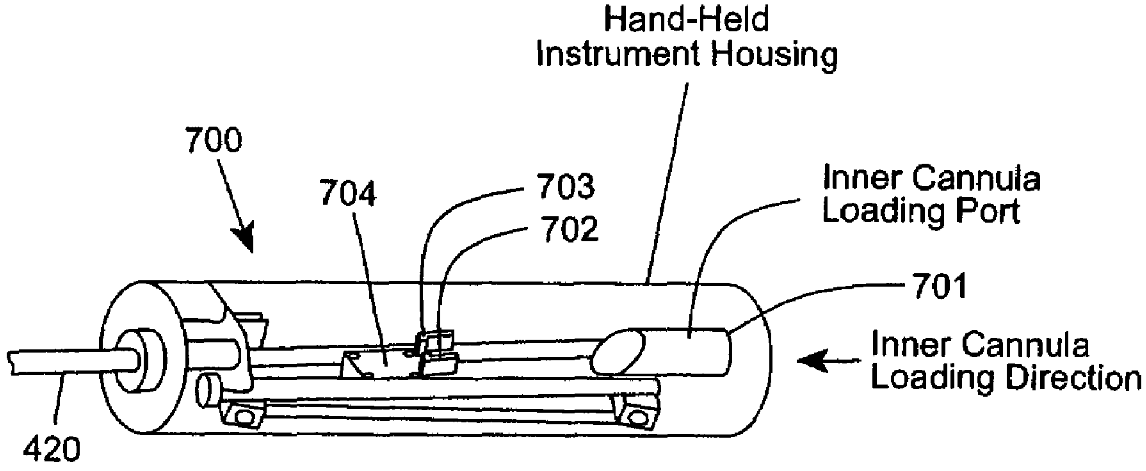
Figure 43B:
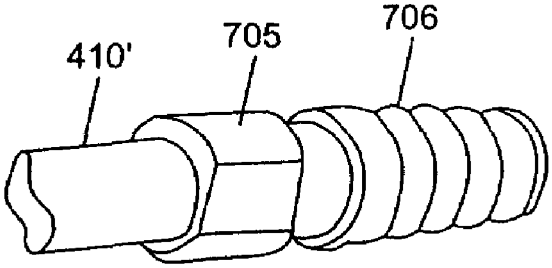

FIG. 42 is a schematic representation of an alternative bi-polar type electro-cauterizing dual cannula assembly for use in the powered liposuction instruments of the present invention, wherein a stream of irrigation fluid is pumped from the base portion of the outer cannula to the distal portion thereof, along a micro-sized fluid conduit formed along the surface walls of the outer cannula, and released into the interior distal portion of the outer cannula through a small opening formed therein, so as to infiltrate and irrigate tissue during aspiration operations;

FIG. 43A is a schematic diagram of an alternate design for an electro-cauterizing powered liposuction instrument of the present invention, wherein the inner cannula is loaded through an inner cannula loading port provided at the rear of the instrument housing and snap-fitted into position within the carriage portion of the air-powered actuator structure installed therein; and FIG. 43B is a schematic diagram of the base portion of the inner cannula designed for use with the rear-loading instrument design shown in FIG. 43A.

DETAILED DESCRIPTION OF THE ILLUSTRATED EMBODIMENTS

With reference to FIGS. 1A through 3D, the first embodiment will be described. In general, liposuction device 1A comprises hand-holdable housing 2, a detachable electro-cauterizing cannula assembly 3 having inner and outer cannulas 4 and 5, and a reciprocation means 6 for causing inner cannula 4 to reciprocate relative to outer cannula 5, which is stationarily disposed with respect to housing 2. This arrangement effectuates periodic displacement of the general location of aspiration along the cannula assembly through the reciprocating movement of inner cannula 4 while permitting electro-cauterization of aspirated tissue during operation of the liposuction device.

As illustrated in greater detail in FIGS. 1B, and 2A through 2E, the electro-cauterizing cannula assembly 3 of the present invention comprises an electrically-conductive inner cannula 4 and an electrically non-conductive outer cannula 5, each comprising hollow inner and outer tubes with distal and proximal ends 4A, 4B and 5A, 5B, respectively.

Figures 2A, 2B, 2C, 2D:
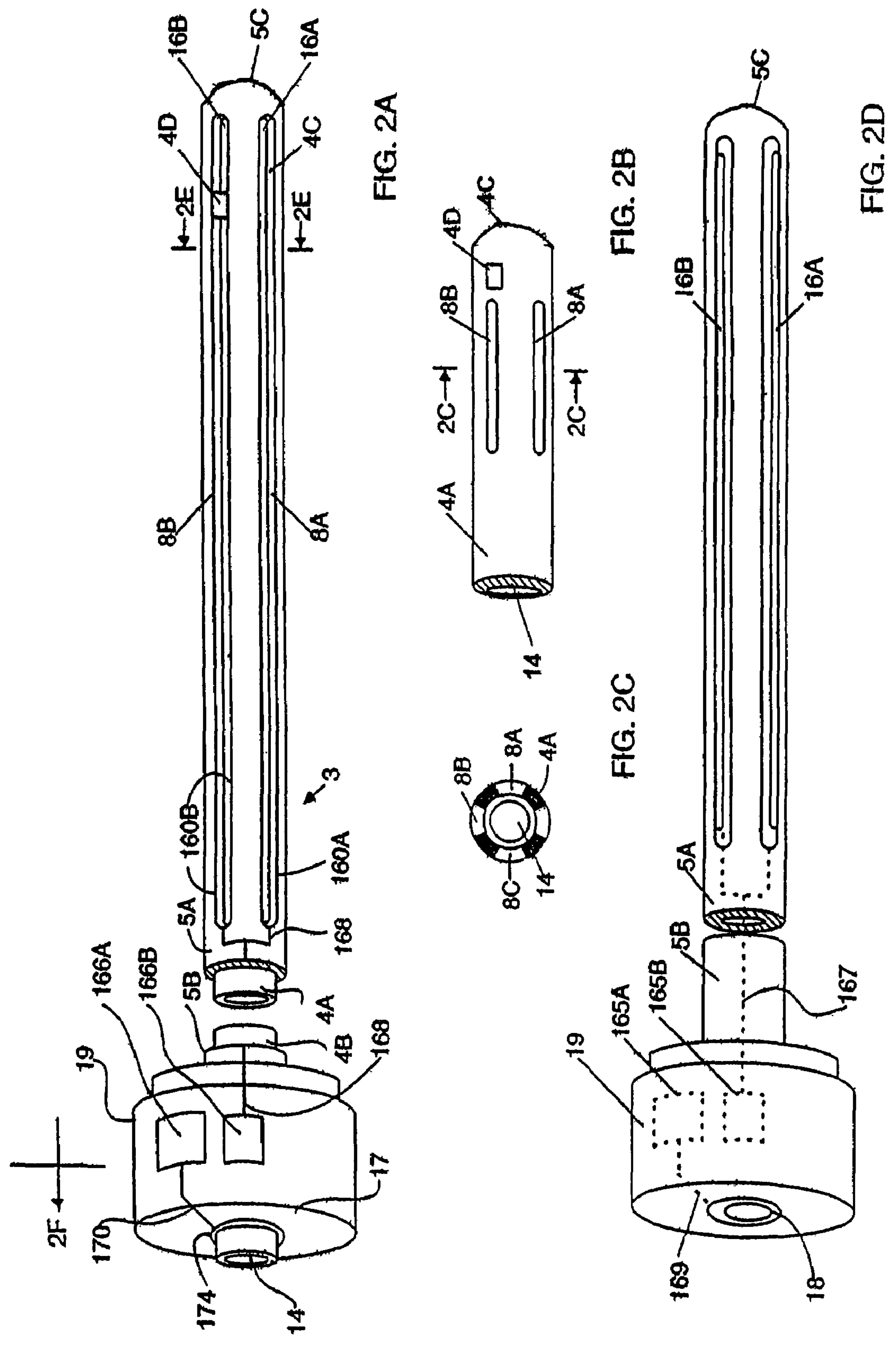
FIG. 2A is a perspective, partially broken away view of the electro-cauterizing cannula assembly of the present invention installed in the liposuction instrument of FIGS. 1A through 8C, in which the electrically-conductive inner cannula adapted to freely undergo sliding movement within the stationary electrically non-conductive outer cannula while electro-cauterization is performed about the aspiration apertures thereof under the control of the surgeon.
FIG. 2B is a perspective view of the distal end of the inner cannula shown in FIGS. 1A, 1B and 2A.
FIG. 2C is a cross-sectional view of the electrically-conductive inner cannula taken along line 2C-2C of FIG. 2B.
FIG. 2D is a perspective, partially broken away view of the electrically non-conductive outer cannula shown in FIGS. 1A, 1B and 2A.

As shown in FIGS. 2B and 2C, the outer cannula 5 comprises a hollow outer tube having a distal end 5A and a proximal end 5B. Four outer aspiration (i.e., suction) apertures generally indicated by reference numerals 8A, 8B, 8C and 8D are provided on the distal end of the inner cannula. As shown, elongated apertures 8A, 8B, 8C and 8D terminate at a predetermined distance away from outer cannula tip 5C, which is essentially blunt for purposes of safety. In general, the length of each of these elongated outer apertures is substantially longer than the longitudinal extent of each respective inner aperture. In the illustrated embodiment, the ratio of these lengths is about 1 to 4; however, in other embodiments, this ration may differ as desired or required in a given application. In a typical embodiment, the length of these elongated outer apertures would be within the range of, for example, two to six inches, commensurate with the amount of displacement to be achieved by each inner aperture.

Figure 1A:
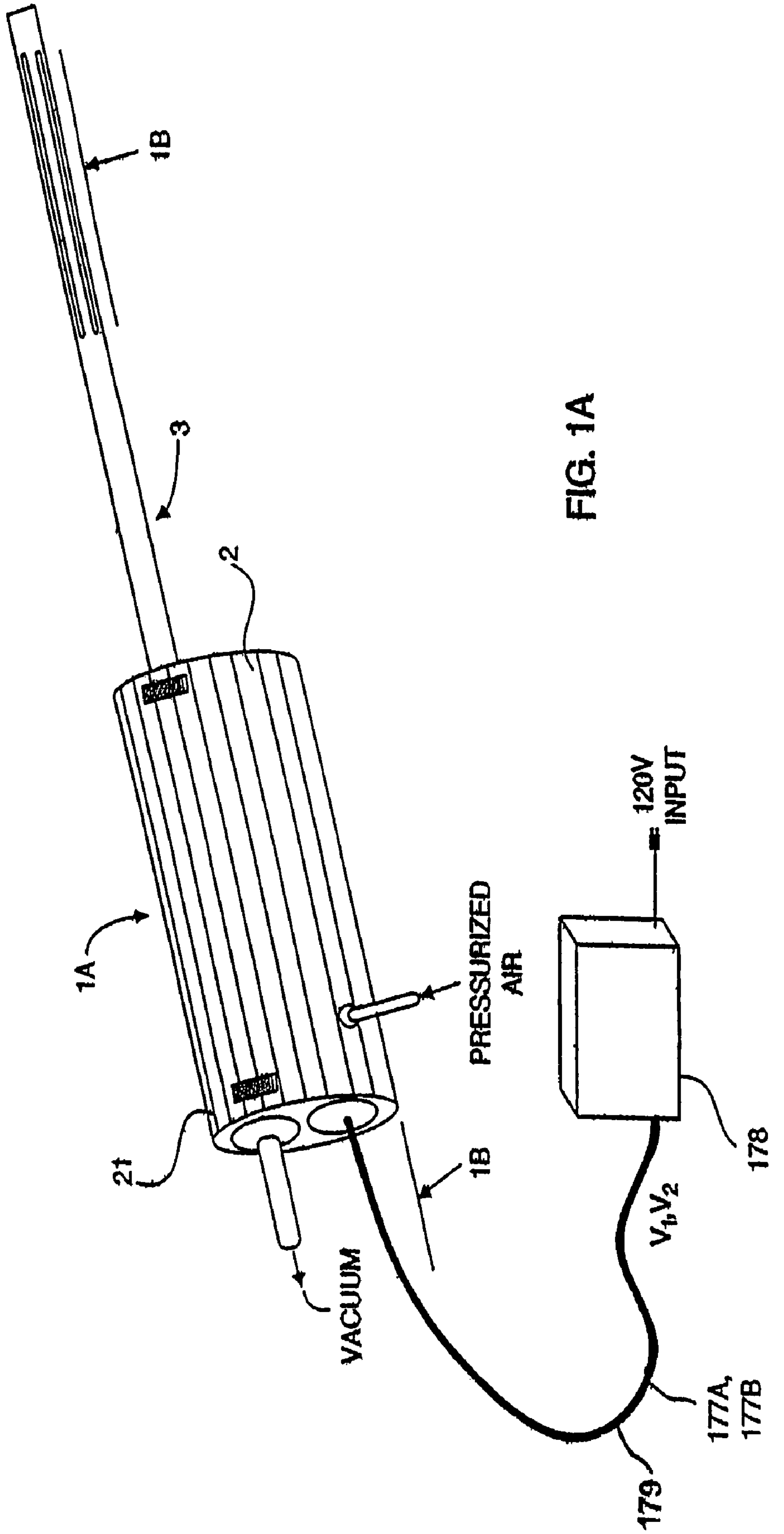
FIG. 1A is a perspective view of a first embodiment of the liposuction device of the present invention.
Figure 1C:
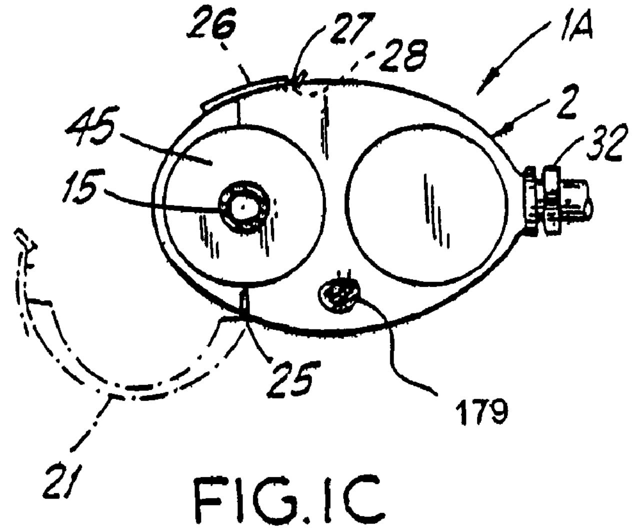
FIG. 1C is an elevated end view of the liposuction device of the present invention illustrated in FIG. 1A, showing the electro-cauterizing cannula assembly thereof retained within the cannula cavity of its hand-holdable housing, and alternatively with the hingedly connected housing cover panel disposed in an open position for removal of the cannula assembly therefrom.
Figure 1B:
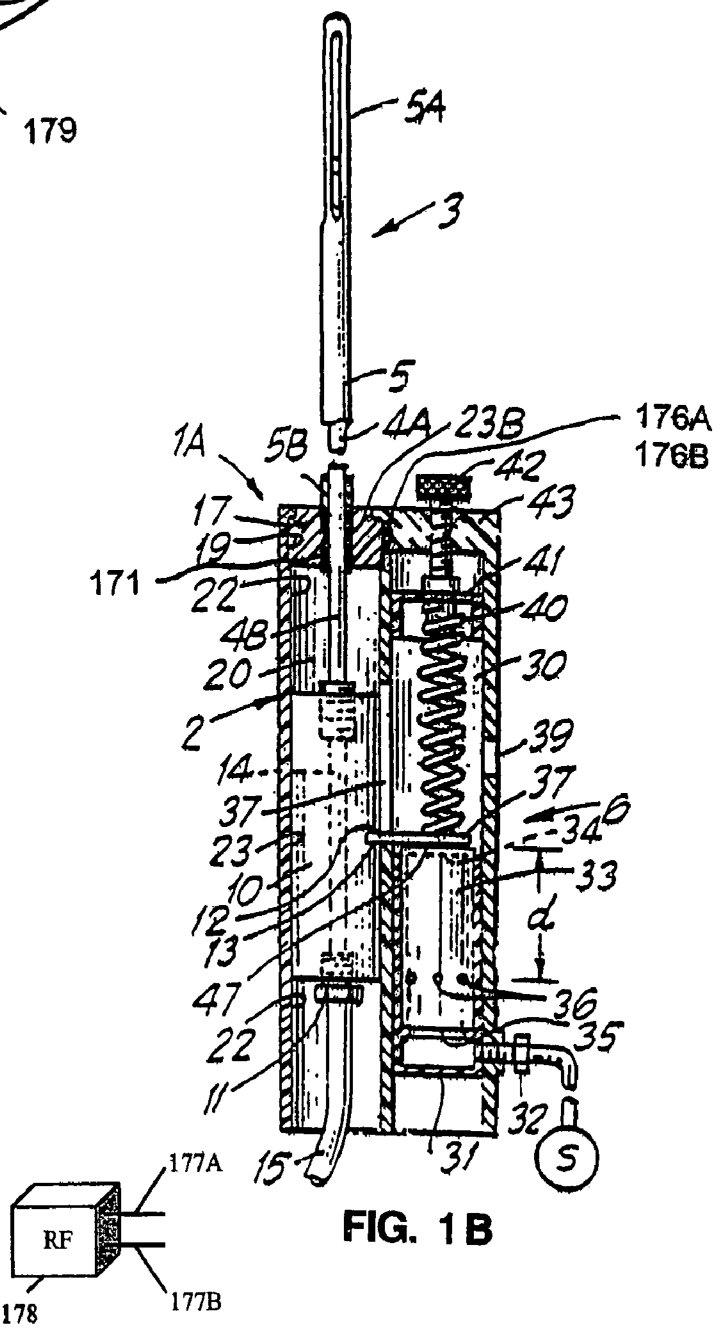
FIG. 1B is a cross-sectional view of the liposuction device of the present invention taken along line 1B-1B of FIG. 1A.

As illustrated in FIG. 1B, an outer cannula base 17 extends from the proximal end of outer tube 5. The outer cannula base 17 comprising a cylindrical structure having a central bore 18, through which distal tip 4C and body of inner cannula 4 can freely pass. The outer cannula base 17 of the illustrative embodiment includes a flanged portion 19 which fits within an annular recess 18 formed in cannula cavity 20 of the hand-holdable housing.

As shown in FIG. 2B, an inner cannula base 10 extends from the proximal end of inner tube 4. As shown, the inner cannula base 10 comprises a cylindrical structure having an outlet port 11 formed in its remote end. The inner cannula base 10 of the illustrative embodiment includes a notch or slot 12 formed in its central most portion. As will be described in greater detail hereinafter, notch 12 functions to releasably receive an extensional portion 13 of actuation element 37, in order to actuate reciprocation of inner cannula 4 within housing 2. As illustrated in FIG. 2B, inner cannula 4 has a continuous passageway 14 which extends from inner aspiration opening 9 to outlet port 11. As shown in FIGS. 2B and 2C, the inner aspiration apertures originate between the distal tip portion 4C. As shown, elongated apertures 16A, 16B, 16C and 16D terminate at a predetermined distance away from outer cannula tip 5C, which is essentially blunt for purposes of safety. In general, the length of each of these elongated inner apertures is substantially longer than the longitudinal extent of each respective outer aperture. In the illustrated embodiment, the ratio of these lengths is about 1 to 4; however, in other embodiments, this ratio may differ as desired or required in a given application. In a typical embodiment, the length of these elongated apertures would be within the range of, for example, two to six inches, commensurate with the amount of displacement to be achieved by each outer aperture with its electro-cauterizing element.

While not shown, a conventional vacuum source is connected to outlet port 11, preferably using optically transparent, semi-flexible tubing 15. With this arrangement, fatty tissue, aspirated fat tissue can be suctioned through apertures 8A, 8B, 8C and 8D and opening 9 and transported along passageway 14 to a reservoir device (not shown), operably associated with the vacuum source.

As illustrated in FIGS. 2A and 2E, electrically-conductive cauterizing electrodes 160A, 160B, 160C and 160D are inserted about the perimeter of outer aspiration apertures 16A, 16B, 16C, and 16D, respectively, and fastened thereto by snap-fitting, adhesive or like means. As shown in FIGS. 3A, 3A1 and 3A2, each electrically-conductive electrode comprises: a sidewall portion 161 which circumferentially extends about the perimeter of the respective aperture formed in the outer cannula; an opening 162 for permitting aspirated tissue and fat and the like to flow therethrough into the interior of the inner cannula; and a circumferential flange 163 substantially perpendicular to sidewall portion 161 and adapted to fit within a recessed groove 164 extending about the upper outer surface of the respective outer aspiration aperture formed in the electrically non-conductive outer cannula. In the illustrative embodiments, cauterizing electrodes 160A through 160D are made from stainless steel, brass, gold or any other electrically-conductive material that is suitable for contact with human tissue during liposuction and like surgical procedures.

As shown in FIG. 2D, the base portion of the outer cannula is provided with a pair of spaced apart recesses 165A and 156B for receiving and securing a first and second electrically-conductive contact pads 166A and 166B, respectively. A first groove 167 is formed within the outer surface of the outer cannula 5 and base portion 19 in order to receive a first length of electrical wiring 168 which establishes electrical contact between the set of cauterizing electrodes 160A through 160D and an electrically-conductive contact pad 166B. Similarly, a second groove 169 is formed within the outer surface of the outer cannula and base portion 19 in order to receive a second length of electrical wiring 170 which establishes electrical contact between the set of cauterizing electrodes 160A through 160D and second electrically-conductive contact pad 166A. A sealing material such as melted plastic can be used to close off the grooves 167 and 169 once the electrical wiring has been recessed within the groove. Alternatively, a thin, outer plastic cannula sleeve having an inner diameter slightly greater than the outer diameter of outer cannula 5 can be slid thereover and secured to the base portion thereof 19 using screw-threads, snap-fit fastening, ultrasonic-welding, adhesive or the like. When completely assembled, electrically-isolated contact pads 166A and 166B are mounted within the side walls surface of the base portion 1, as shown in FIG. 2A. It is understood, however, that contact elements 166A and 166B can be mounted elsewhere in the base portion of the outer cannula.

Figure 2F:
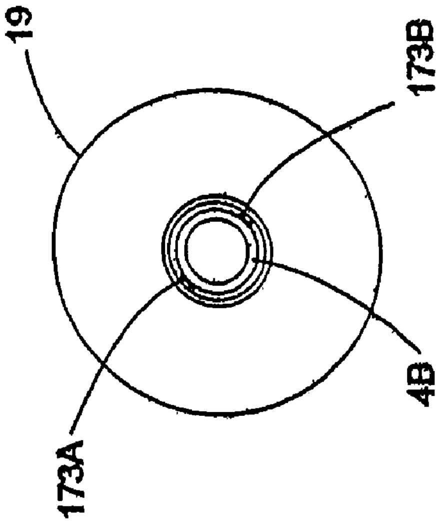
FIG. 2F is a cross-sectional view of the cannula base taken along line 2F-2F of FIG. 2A.

As shown in FIG. 2A, an electrically-conductive collar and brush device 17 shown in FIGS. 3B and 3B1 is inserted within the central bore formed in the base portion 19 of the electrically non-conductive outer cannula. The collar and brush device 171 comprises a cylindrical tube 172 made from electrically-conductive material (e.g., stainless steel) having an outer diameter that is slightly less than the diameter of the central bore formed through the base portion of the inner cannula. As shown in FIGS. 3B and 3B1, a pair of diametrically-opposed leaf-like electrical contact elements 173A and 173B project inwardly from the cylindrical walls of the device towards it s axial center. As best shown in FIG. 2F, the function of electrical contact elements 173A and 173B is to establish electrical contact between second contact pad 166A (on base portion 10) and electrically conductive inner cannula 4 when the inner cannula is slid through the central bore 18 of the outer cannula, as shown in FIG. 2A. A small annular flange 174 is formed on one end of the cylinder 172 to delimit the depth of its insertion.

As shown in FIG. 2E, the sidewall portion 161 of each cauterizing electrode 160A through 160D is of sufficient width ($w_g$) to provide a gap region 175 between (i) the electrically-conductive inner cannula 4 adjacent the electrode and (ii) the sidewall portion 161 thereof. Preferably, the width of each gap 175 is selected so as to minimize electrical arcing (i.e., sparking) between each electrode 160 and the electrically conductive inner cannula 4 when an RF signal of, for example, about 5000 kHz at 800 Volts is applied thereacross during electro-cauterization.

As shown in FIG. 1B, contact pads 166A and 166B establish electrical contact with conductive elements 176A and 176B and are embedded within recess 17. Electrically conductive elements 176A and 176B are connected to the RF supply and RF return signal terminals 177A and 177B, respectively, of bipolar RF signal generator 178. In the preferred embodiment, RF bipolar signal generator 178 is realized as the Instant Response™ Electrosurgical Generator (Model Force FX) by ValleyLab International, a subsidiary of Pfizer. Inc. This Electrosurgical Generator can be easily connected to the electro-cauterizing electrodes hereof by electrical cabling 179 in order to drive the same with bipolar outputs produced from the Electrosurgical Generator. Notably, the Instant Response Electrosurgical Generator 178 includes three bipolar output modes, namely: Low/Precise; Medium/Standard; and Macrobipolar. When operated in the Low and Medium bipolar modes, low output voltages are produced in order to prevent sparking across the electro-cauterizing electrodes.

When inner cannula 4 is installed within outer cannula 5, as shown in FIGS. 1A and 2A, inner apertures 8A, 8B, 8C, and 8D are able to freely slide along elongated outer apertures, 16A, 16B, 16C and 16D, respectively. Also, at each positioning of the inner cannula within the outer cannula, aspiration is permitted through each "effective" aspiration (i.e., suction) aperture formed by the partial registration of each inner aspiration aperture with its corresponding outer aspiration aperture. Aspiration through these resulting effective aspiration apertures or openings, continues along passageway 14 and exits through outlet port 11. Consequently, the general location of aspiration along cannula assembly 3 is periodically displaced as inner cannula 4 is reciprocated relative to outer cannula 5, which is stationary with respect to the hand-supportable housing 2.

In order to maintain inner aspiration apertures 8A, 8B, 8C and 8D aligned with outer aspiration apertures 16A, 16B, 16C and 16D, respectively, and thus ensure partial registration therebetween, the distal end of the inner and outer tubes are provided with a keying system. In the illustrated embodiment, the keying system comprises a keying element 4D disposed on outer surface of the inner cannula, before distal tip 4C. Keying element 4D can be a rigid or flexible element that slides within an elongated outer aperture (e.g. 16B) and prevents axial rotation between cannulas 4 and 5 as they undergo relative reciprocation. To assemble cannula assembly 3, distal tip 4C of the inner cannula is inserted through bore 18 in outer cannula base 17 so that the distal end of inner cannula 4A is slidably received within outer cannula 5, as shown in FIG. 3A. In this configuration, keying element 4D is received and guided within elongated aperture 8B' as shown. In this general configuration, cannula assembly 3 is installed within cannula cavity 20 by first opening housing cover 21, shown in FIG. 1C. Then outer cannula base flange 17 is inserted within annular recess 19 and actuation extension 13 within inner cannula base notch 12. Thereafter, housing cover 21 is closed shut and liposuction device 1A is ready for operation. A conventional vacuum source is then connected to outlet port 11, preferably using optically transparent, semi-flexible tubing 15. With this arrangement, fatty tissue, aspirated through apertures 8A/16B, 8B/16B and 8C/16C and 8D/16D and opening 9, can be transported through passageway 14 to a reservoir device (not shown), operably associated with the vacuum source.

As shown in FIG. 1A, the gross geometry of housing 2 is preferably that of an ellipsoid, however, other geometries such as, for example, a cylindrical structure, can be used in practicing the present invention. Housing 2 contains cannula cavity 20, which extends along the entire longitudinal extent of the hand-holdable housing. In the illustrated embodiment, cannula cavity 20 has generally cylindrical bearing surfaces 22 which match the outer bearing surface 23 of inner cannula base 10, to permit sliding movement of inner cannula 3 within cavity 20. While cylindrical bearing surfaces have been selected in the illustrated embodiment, the use of other forms of bearing surfaces (e.g., rectangular or triangular) is contemplated. To minimize friction, bearing surfaces 22 and 23 may be coated with a Teflon$^R$ or functionally equivalent coating, to facilitate easy sliding of inner cannula base 10 within cavity with low wear. As illustrated in FIG. 1B, cannula cavity 20 also includes annular recess 19, into which annular base flange 19 is adapted to be received in order to render the outer cannula essentially stationary with respect to hand-holdable housing 2.

As shown in FIG. 1B, electrical contact pads 176A and 176B are embedded within surface-recesses formed within the wall surfaces of the annular recess 19. Preferably, electrically-conductive contact pads 176A and 176B are made from electrically conductive material having a shaped which is similar to the shape of electrically conductive pads 166A and 166B that are embedded within the outer surface of the base portion of the outer cannula 5. When the cannula assembly of this embodiment is installed within the hand-holdable housing, the electrical contact pads 166A and 166B on the base portion of the outer cannula will automatically establish electrical contact pads 176A and 176B within recess 19, respectively. In this way, the RF supply and return voltages from RF signal generator 178 are automatically applied to the electro-cauterizing electrodes embedded within the cannula assembly of the present invention.

As illustrated in FIG. 1C, hand-holdable housing 2 is provided with a hinged cover 21. Hinged cover 21 allows cannula cavity 20 to be opened and accessed so that cannula assembly 3 can be selectively installed in cannula cavity 20 and removed therefrom as desired or required. Cover panel 21 has a semi-circular cross-sectional geometry and is connected to the remaining portion of housing 2 by a conventional hinge means 25. To secure cover panel 21 to the remainder of housing 2, a releasable locking means 26 is provided at the interface of hinge cover 21 and housing 2, as shown. Releasable locking means 26 can realized in a variety of ways, including, for example, using a spring biased lamp element 27 which engages in a notch 28 formed in the external surface of the remaining housing portion, as illustrated in FIG. 1C.

In general, there are numerous ways to effectuate reciprocation of inner cannula 4 within cannula cavity 20 and thus within stationary outer cannula 5. Examples of possible reciprocation means 6 include, but are not limited to, gas or electrically driven motor(s). In the embodiments illustrated in FIGS. 1A through 1C, FIGS. 4A through 6A, FIGS. 7 through 8A, FIGS. 6A through 6D, and FIGS. 10 through 14D, one or more gas driven piston-type motors are employed to realize the reciprocation means 6 within the liposuction instrument. In the embodiment illustrated in FIGS. 9A through 9F, a rotary-type motor is used to realize reciprocation means 6 of the present invention.

As illustrated in FIG. 1B, a piston-type motor 6 is mounted within a motor cavity 30 provided adjacent cannula cavity 20 of housing 2. Notably, this reciprocation means cavity 30 extends essentially parallel to cannula cavity 20 and along a substantial portion of the longitudinal dimension of hand-holdable housing as will become more apparent hereinafter. This unique spatial relationship between the cannula cavity and reciprocation means cavity within housing 20, ensures optional cannula displacement relative to longitudinal dimensions of the hand-holdable housing.

In general, motor 6 comprises a chamber housing 31 having a gas inlet port 32 and an inner chamber generally indicated by reference numeral 33. Slidably received within the inner chamber of housing 31 is a movable piston 34 having formed in the lower portion wall 35, one or more gas outlet ports 36. Mounted to the top portion of movable piston 34 is actuation element 37, whose extension 13 projects through longitudinally disposed slot 38 formed in the bearing wall surface 22 of cannula cavity 20. As shown in FIG. 1B, actuation extension 13 passing through slot 38, is received within notch 12 formed in inner cannula base 10 and operably associates inner cannula 3 with motor 6.

As illustrated in FIG. 1B, chamber housing 31 is fixedly disposed within motor cavity 30. Motor cavity 30 is also provided with at least one port 39 for ventilating to the ambient environment, gas released from inner chamber 33 upon movable piston 34 reaching it maximum displacement or excursion. Movable piston 34 is biased in the direction of chamber housing 31 by way of a spring biasing element 40. The compliance of spring biasing element 40 can be adjusted by moving the position of slidable wall 41 by rotating, for example, threaded element 42 passing through a portion 43 of housing 2, as shown. With this arrangement, adjustment of wall 41, closer to or farther from chamber housing 31, results in decreasing or increasing, respectively, the compliance of spring biasing element 40. This mechanism, in turn, provides a simple, yet reliable way in which to control the rate of reciprocation of movable piston 34, and thus the rate of reciprocation of inner cannula 3 relative to housing 2.

The manner of operation of piston-type motor 6 is described as follows. Gas, such as pressurized air or $N_2$ gas, is introduced under constant pressure to inlet port 32 of chamber housing 31. As the gas fills up the volume enclosed by the interior walls of movable piston 34 and chamber 33, inner chamber 33 begins to expand, forcing movable piston 34 upwardly against the biasing force of spring biasing element 40. When movable piston 34 is displaced sufficiently enough from chamber housing 31 so that gas within expanding chamber 33 can be released through gas exit port 39 to the ambient atmosphere, piston 34 will be forced back downwardly into chamber housing 31. The rate of the forced downward piston movement is inversely proportional to the compliance of spring biasing element 40. Subsequently, chamber 33 will again fill up with gas, piston 34 will again be displaced and gas subsequently vented, whereupon reciprocating displacement of piston 34 will be repeated again in a cyclical manner. Since movable piston 34 is operably connected with inner cannula base 10 by way of actuation element 37, this reciprocating movement of piston 34 results in reciprocating movement of inner cannula 3 within cannula cavity 20. Furthermore, this relative reciprocation between the inner cannula and the outer cannula results in periodic displacement of the effective aspiration apertures along the distal end portion of the cannula assembly.

As illustrated in FIG. 1B, the amount of excursion that piston 34 is permitted to undergo before gas venting and subsequent downward piston movement occurs, is determined by the distance “d” defined between gas output port 32 and top wall surface 47 of chamber housing 31. A typical cannula excursion distance of about four inches, for example, will necessitate that the parameter d, defined above, be also about four inches.

Figure 4A:
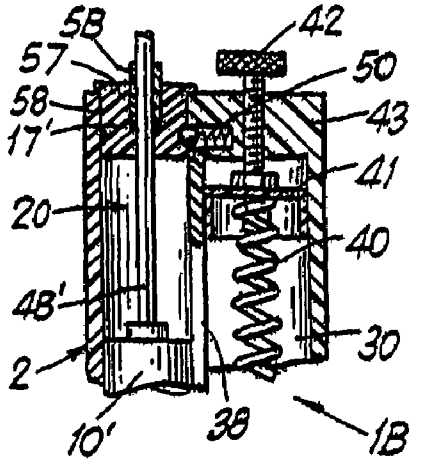
FIG. 4A is a cross-sectional view of a portion of another embodiment of the liposuction device of the present invention, illustrating an alternative outer cannula retention means.
Figure 4B:
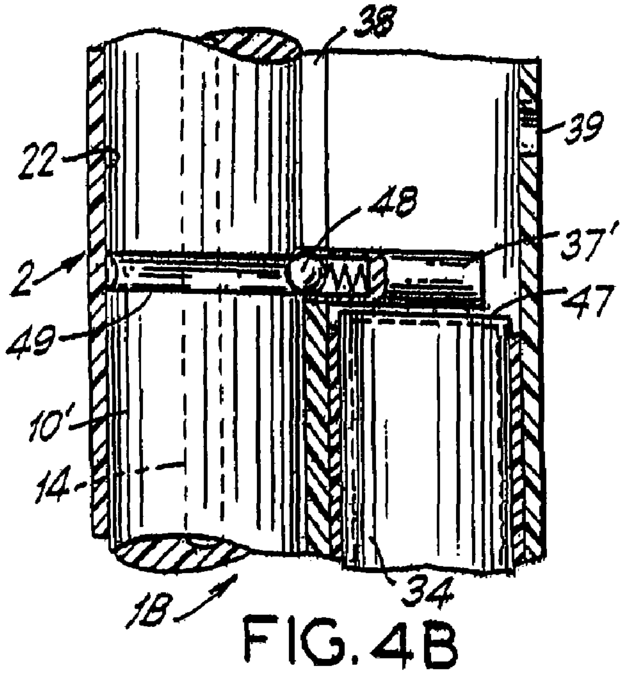
FIG. 4B is a cross-sectional view of a portion of the liposuction device of FIG. 4A, illustrating an alternative inner cannula retention means.

In FIGS. 4A and 4B, a second embodiment of the liposuction device of the present invention is shown. Liposuction device 1B has an alternative cannula assembly retention means while inhering all of the structural features of the first embodiment illustrated in FIGS. 1A through 1C. In particular, liposuction device 1B does not have a hingedly connected housing cover panel, and instead incorporates a snap-fit type cannula assembly retention mechanism. In accordance with this embodiment, actuation element 37' has an extension which is essentially flush with elongated slot 38 formed in cavity wall 22.

In FIGS. 4A and 4B, an alternative embodiment of the electro-cauterizing cannula assembly hereof is shown. This cannula assembly is similar to the above-described cannula assembly in all respectives except the extension on actuation element 37. In this alternative embodiment, the extension on actuation 37' is provided with a spring biased ball bearing 48 that projects slightly beyond cannula cavity wall surface 22. When inner cannula base 10' is pushed into cannula cavity 20 in the vicinity of actuation element 37', ball bearing 48 engages within indentation ring 49 circumferentially formed about inner cannula base 10'. Notably, spring biased ball bearing 48 functions as an engaging means for inner cannula base 10'.

As shown in FIG. 4A, the engaging means for outer cannula base 17' is also realized as a spring biased ball bearing 50 installed through cannula cavity wall 22. Outer cannula base 5' is provided with an annular flange 47 and indentation ring 49 circumferentially formed about outer cannula base 17'. As shown, annular flange 57 establishes surface to surface contact with peripheral surface 58 area of the housing when cannula base 5' is pushed into cannula cavity 20. In this position, ball bearing 50 engages within indentation ring 49 and a snap-fit engagement is established. This arrangement serves to retain both inner and outer cannulas 3' and 4 cannula cavity 20', in a releasable manner, as actuation element 37' is caused to reciprocate periodically. The outer cannula is simply removed from cannula cavity 20 by quickly pulling on outer cannula tube 5 with a modest degree of force, to overcome the bias force of engaged ball bearing 50. Similarly, the inner cannula is simply removed by quickly pulling on inner cannula tube 4' to over come bias force of engaged ball bearing 50. Advantageously, this cannula assembly retention mechanism can also provide a safety release feature, in that if inner cannula 4', for example, becomes snagged during an operation, it will disengage from the reciprocation means 6 if a proper spring biasing force is selected for ball bearing 50.

Figures 6A, 6B, 6C, 6D, 7A, 7B, 8:
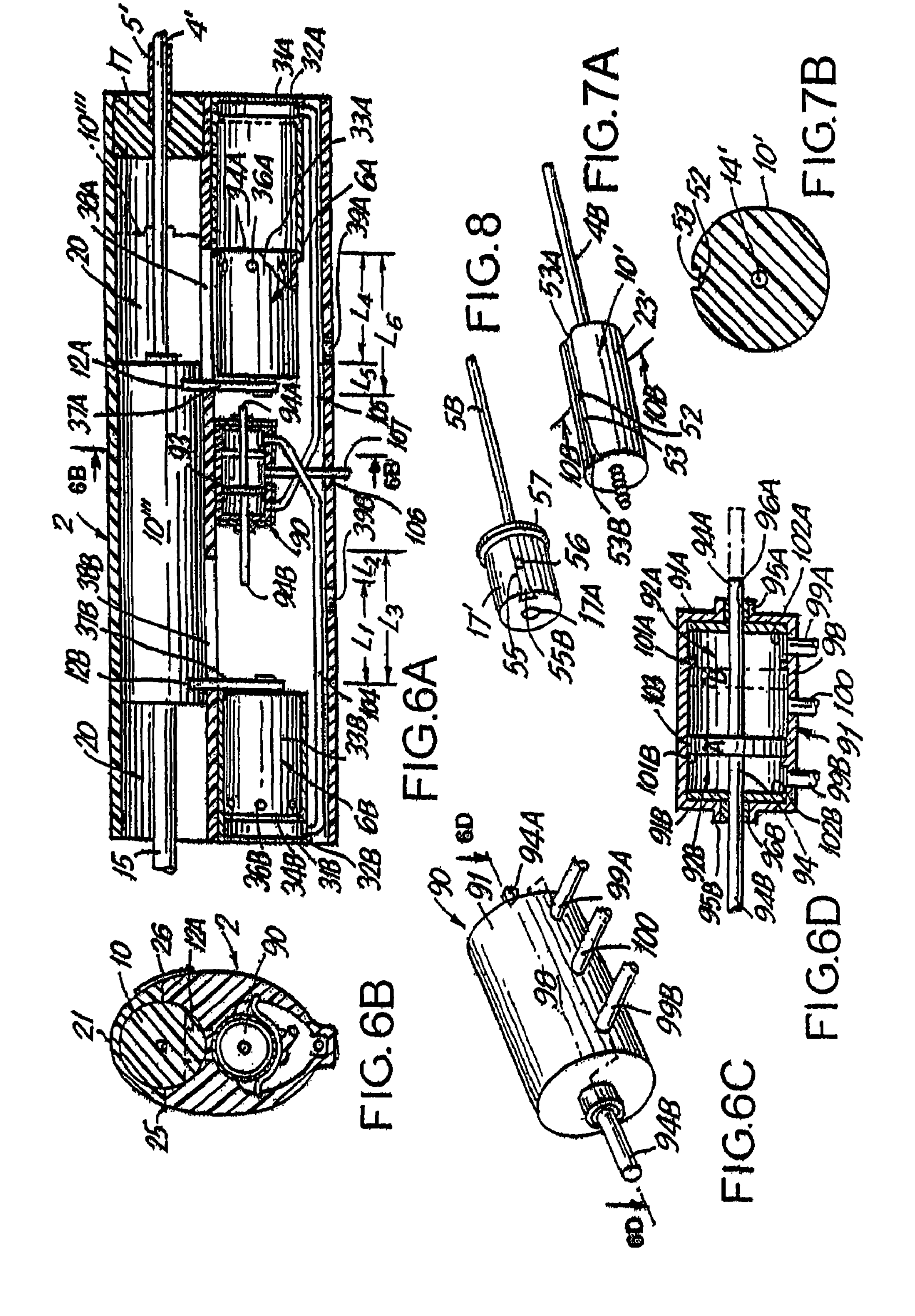
FIG. 6A is a cross-sectional view of another embodiment of the liposuction device of the present invention, illustrating the use of a pair of gas driven piston-type motors and a mechanically-operated gas flow control device disposed in its first state of operation.
FIG. 6B is a cross-sectional view of the liposuction device of the present invention taken along line 6B-6B of FIG. 6A.
FIG. 6C is a perspective view of the preferred embodiment of the mechanically-operated gas flow control device illustrated in FIG. 6A.
FIG. 6D is a cross-sectional view of the gas flow control device of the present invention taken along line 6D-6D of FIG. 6C.
FIG. 7A is a perspective, partially broken away view of a snap-fit type inner cannula intended for use with the liposuction device of FIG. 4A.
FIG. 7B is a cross-sectional view of the outer cannula of the present invention taken along lines 7B-7B of FIG. 7A.
FIG. 8 is a perspective, partially broken away view of a snap-fit type outer cannula intended for use in connection with the liposuction device of FIG. 4A.

FIGS. 7A, 7B and 8 also show an electro-cauterizing cannula assembly according to the present invention which is adapted for use with liposuction instruments having cannula retention capabilities of the snap-in type described above. Notably, the elements which correspond to inner and outer cannulas illustrated in FIGS. 2A through 3B1, are indicated by similar reference numbers.

In the embodiment featured in FIGS. 7A and 7B, inner cannula base 10" has a deeply formed spherical indentation 52 which is adapted to receive ball bearing 48 mounted in the extension of in actuation element 37. To facilitate guiding ball bearing 48 into spherical indentation 52, a longitudinally extending groove 53 is formed in inner cannula base 10". Also, as shown, widened recess portions 53A and 53B are provided at opposite ends of groove 53 to facilitate initial insertion of ball bearing 48 in groove 53. When inner cannula base 10" is slid into cannula cavity 20, ball bearing 48 snaps into indentation 52 to establish a locked position. Biased ball bearing 48 engaged in spherical indentation 52 serves to retain inner cannula 5 within cannula cavity 20, while facilitating reciprocation of inner cannula 5 when actuation element 37' is caused to reciprocate.

Similar to the snap-fit inner cannula retention mechanism illustrated in FIGS. 7A and 7B, FIG. 8 shows outer cannula base 17" having a longitudinally extending groove 55. Also, as shown, widened recess portions 55A and 55B are formed at opposite ends of groove 55 to facilitate insertion of ball bearing 50 into spherical indentation 56. When outer cannula base 17" is slid into cannula cavity 20, ball bearing 50 snaps into spherical indentation 56 to establish a locked position. When this occurs, annular flange 57 will engage with outer peripheral surface 58, about circular access opening leading into cannula cavity, shown in FIG. 4A. Upon such engagement, outer cannula 5 is rendered stationary relative to hand-holdable housing 2. As with inner cannula 4, the outer cannula is simply removed from cannula cavity 20 by pulling on outer cannula tube 5 with a modest degree of force to overcome the bias force of engaged ball bearing 50.

Figure 5:
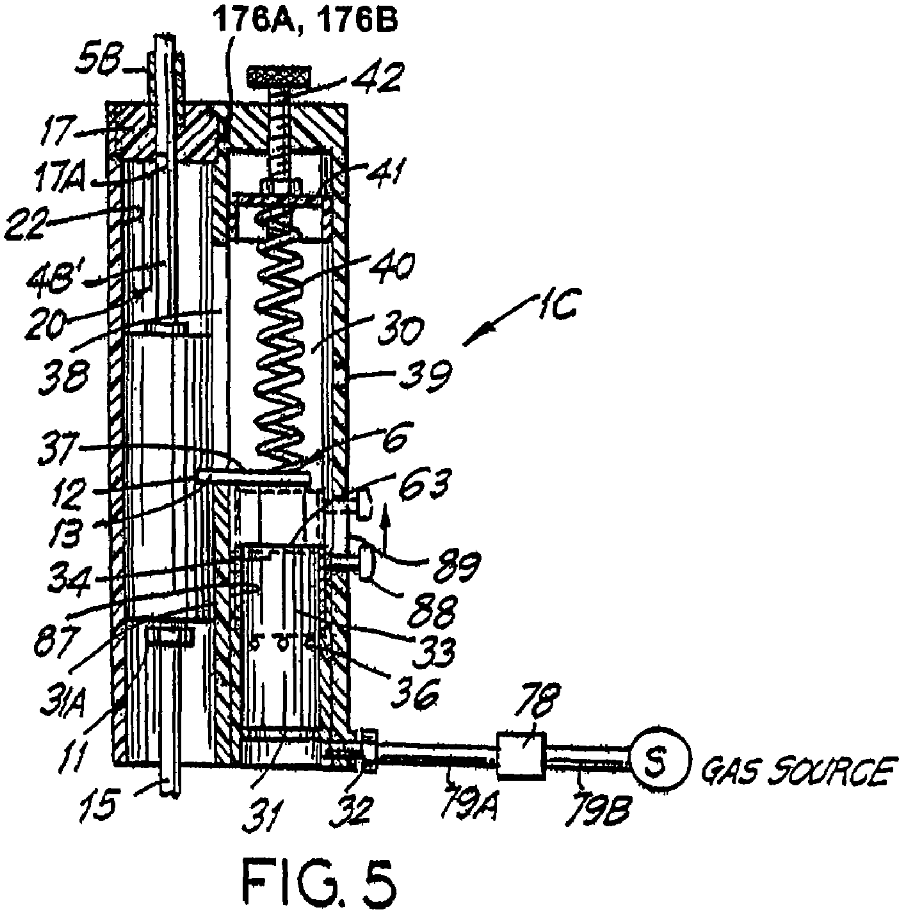
FIG. 5 is a cross-sectional view of another embodiment of the liposuction device of the present invention, illustrating a means for controlling the mount of excursion of the aspiration aperture along the cannula assembly.

In order to selectively adjust the amount of cannula excursion permitted during a liposuction operation, piston-type motor 6 can be modified, as shown in FIG. 5, to produce embodiment of the liposuction device of the present invention. As illustrated in FIG. 5, the basic structure of liposuction device 1C is similar to that shown in FIGS. 1A through 1C, except that a user-adjustable intermediate housing wall 88 is disposed between the inner walls 31A of chamber housing 31 and the outer walls 34A of movable piston 34. Intermediate housing wall 87 is operably associated with an excursion selection means realized as a slidable member 88 fixedly attached to the upper portion of intermediate housing wall 59. Preferably, slidable member 88 extends through a slot 89 formed in the wall of housing 2 and can be slid, for example, by movement of the surgeon's thumb. The function of intermediate housing wall 87 is to effectively raise the height of the chamber housing wall, and thus selectively increase distance d, defined, for example, as the distance between gas outlet port 32 in piston 34 and upper portion 63 of the chamber housing wall. In this way, movable piston 34 must undergo a larger displacement before compressed gas will be released and piston 34 permitted to be forced downwardly under the biasing force of biasing spring element 40.

As illustrated in the embodiment shown in FIG. 5, it is also possible to control the rate of reciprocation of the inner cannula by controlling the rate of gas flow entering chamber 33 of piston-type motor 6. This can be achieved using a conventional gas flow regulation device 78 inserted between source of gas "S" and inlet port 32 of chamber housing 31. As shown, tubing sections 79A and 79B are used to achieve fluid communication between these elements. Typically, cannula reciprocation rates will be in the range of 30 to 90 reciprocation cycles per minute, and the corresponding gas flow rates will depend on parameters including, for example, the compliance of biasing spring 40, the volumes of movable piston 34 and chamber housing 31, the cross-sectional diameter of gas inlet port 32, and the cross-sectional diameter of gas outlet ports 36 in the piston.

Referring to FIGS. 6A through 6D, there is shown another embodiment of the liposuction device of the present invention. In liposuction device 1F, the housing and cannula assembly are generally similar to those of the previously described embodiments, with the exception of several differences which will be described below.

As illustrated in FIG. 6A, a pair of piston-type motors 6A and 6B of the type generally indicated in FIGS. 1A through 1C and 5, are fixedly installed within respective motor cavities 30A and 30B of housing 2. Each piston-type motor 6A and 6B has a respective chamber housing and movable piston, indicated by 31A and 31B, and 34A and 34B, respectively. Actuation elements 37A and 37B are fixedly connected to respective pistons 34A and 34B and project through respective elongated slots 38A and 38B formed in cannula cavity wall 22; this is achieved, in a manner similar to that described in connection with the embodiments shown in FIGS. 1A through 1C, 4A, 4B and 5. While not shown in FIG. 6A, preferably a rod or bar is fixedly attached between actuation elements 37A and 37B in order to maintain them a fixed distance apart, and yet provide an operable connection between the inner cannula 41 and actuation elements 37A and 37B in the manner described below. As shown in FIG. 6B, this embodiment includes hinged cover panel 21 in a manner similar to that described in the embodiments of FIGS. 1A, 1C, 5, 6A and 8A.

As illustrated in FIG. 6A, inner cannula base 10'" has first and second receiving slots or notches 12A and 12B, into which extensions 13A and 13B of respective actuation elements 37A and 37B are received. Such operable connections between movable pistons 6A and 6B and inner cannula base 10'" enables inner cannula 4' to reciprocate relative to housing 2 when actuation elements 37A and 37B are caused to reciprocate relative to respective gas driven motors 6A and 6B.

In order to control the filling and venting of chambers 33A and 33B of the first and second piston motors, to effectuate cyclical reciprocating motion of actuation elements 37A and 37B and thus inner cannula 4', a mechanically-operated gas flow control device 90 is employed in operable association with an external source of pressurized gas (not shown), gas inlet ports 32A and 32B, and movable pistons 34A and 34B.

As illustrated in greater detail in FIGS. 6C and 6D, gas flow control device 90 comprises a shuttle valve housing or casing 91, having first and second shuttle chambers 92A and 92B. These shuttle chambers are separated by a shuttle valve member 93 which is fixedly attached to a slidable shaft 94. As illustrated, shuttle valve member 93 is slidable between two positions or states "A" and "B". In order to achieve this shaft 94 extends through bores 95A and 95B formed in shuttle chamber and walls 91A and 91B respectively, in which seals 96A and 96B are installed in a conventional manner. When the shuttle valve 93 is centrally disposed in casing 91 between states A and B, shaft ends 94A and 94B protrude equally beyond respective bores 95A and 95B.

Adjacent one end of cylindrical shuttle chamber side wall 98, a first gas exit port 89A is formed, whereas adjacent the other end of wall 98, a second gas exit port 98B is formed, as shown. At about intermediate the end walls, a gas inlet port 100 is formed in shuttle chamber side wall 98. A pair of annulus-shaped shuttle valve stops 101A and 101B are formed at opposite end portions of the interior surface of cylindrical wall 98. These stops 101A and 101B serve to limit sliding movement of shuttle valve 93 when shaft 94 is displaced in one of two possible axial directions by actuation elements 37A and 37B, respectively, as shown in FIG. 6A. As will be discussed in greater detail hereinafter, it is these actuation elements 37A and 37B which displace shaft 94 and thus shuttle valve 93 between one of two states, as movable pistons 34A and 34B are caused to reciprocate. Preferably, at least a portion of shuttle valve 93 is formed of a ferromagnetic material so that ferrous end walls 102A and 102B will attract ferromagnetic shuttle valve 93 and pull it against one of stops 101A and 101B and into gas flow state A or B, i.e., when shuttle valve 93 is brought into proximity therewith upon displacement of shaft 94 by one of actuation elements 37A and 37B. Peripheral side surfaces of shuttle valve 93 are provided with seals 103 to prevent gas leakage between shuttle chambers 92A and 92B.

As illustrated in FIG. 6A, first gas exit port 99A of device 90 is in a fluid communication with second chamber housing 31B by gas channel 104, whereas second gas exit port 99B is in fluid communication with first chamber housing 31A by gas channel 105. In the illustrated embodiment, gas inlet aperture 106 is formed through housing 2 and permits gas channel 107 to establish fluid communication between gas inlet port 100 and the external source of pressurized gas. Notably, chamber housings 31A and 31B, shuttle valve housing 91, gas channels 104, 105 and 107 can be realized as discrete elements, as shown, or alternatively as integrally formed elements which are part of the interior of the hand-holdable housing itself.

The principal function of gas flow control device 90 is to control the flow of gas to pistons 34A and 34B so that only one of the gas pistons is actively driven at a time, while the other is passively driven. The manner of operation of gas flow control device 90 in cooperation with the periodic displacement of pistons 34A and 34B, will now, be described.

Owing to the fact that shuttle valve 93 is magnetically biased to be in essentially one of two possible positions, or gas flow states, gas will initially be caused to flow into one of piston-chamber housings 31A or 31B, and cause its respective piston and actuation element to move away (i.e. protract) from its respective chamber housing. Only along a small portion of the piston excursion will shuttle valve shaft 94 and thus shuttle valve 93, be displaced within shuttle valve housing 91 as the actively driven piston is displaced upon buildup of pressurized gas within its respective chamber.

To illustrate this cyclical process, it will be assumed that gas flow control valve 90 is initially in state A, as shown in FIG. 6A. Here, piston 34A has reached its maximal displacement and pressurized gas within chamber 33A has been substantially vented through gas outlet port 26A and through ports 39A and 39B. In this position (state A), shuttle valve 90 is magnetically biased against stops 101B so that gas is caused to flow from the external gas source (not shown), through first shuttle chamber 93A and into second chamber housing 33B. With shuttle valve 92 in this state, gas pressure is allowed to build up in chamber 33B, displacing piston 34B and actuation element 37B to protract from second chamber housing 31B. Therewhile, inner cannula base 10''' is caused to undergo an outwardly directed excursion within cannula cavity 20, commensurate with the active displacement of piston 34B. During piston excursion (i.e., travel) defined over length $L_1$, shuttle valve 93 remains in state A against stop 101B.

Then over piston excursion $L_2$, actuation element 37B contacts shaft end 94B and displaces shuttle valve 93 away from stop 101B to about mid-position in shuttle housing 91, approximately over input port 100, at which point, magnetic shuttle valve 93 is pulled toward ferrous plate 102A into state B and against stop 101A, as shown in FIG. 6A with phantom lines. At this phase in the cycle, piston 34A is fully retracted within chamber housing 31A, while piston 34B is fully protracted from chamber housing 31B and displaced a distance $L_3$ from the upper portion thereof (i.e., $L_3=L_1+L_2$). In State B, gas flow control device 50 directs the flow of pressurized gas from the external source, along channel 107, through second shuttle chamber 92B and along channel 105 and into piston chamber housing 31A.

Magnetically biased shuttle valve 93 remains in state B as chamber housing 31A fills with pressurized gas, expanding the chamber 33A and actively displacing piston 34 A away from chamber housing 31A, while causing piston 34B to passively retract back into its chamber housing 31B. All the while, inner cannula base 10''', being operably associated with actuation elements 37A and 37B, undergoes a commensurate amount of inwardly directed excursion within cannula cavity 20. When piston 34B is displaced an amount of distance $L_4$, actuation element 37A contacts shaft end 94A and displaces shuttle valve 93 a small distance $L_5$, at which point, magnetic shuttle valve 93 is pulled towards ferrous plat 102B, back into state A and against stop 101B. At this phase in the cycle, piston 34B is fully retracted within chamber housing 31B while piston 34A is fully protracted from chamber housing 31A and displaced at a distance $L_6$ from the upper portion thereof (i.e., $L_6=L_4+L_5$). In state A, gas flow control device 90 directs the flow of pressurized gas from the external source, along channel 107, through first shuttle chamber 92A, along channel 104 and into piston chamber housing 31B.

Magnetically biased shuttle valve 93 remains in state A as chamber housing 91B fills with pressurized gas, expanding chamber 3B actively displacing piston 34B away from chamber housing 31B, while causing piston 34A to passively retract back into its piston chamber housing 31A. All the while, inner cannula base 10''', being operably associated with actuation elements 37A and 37B, undergoes once again a commensurate amount of outwardly directed excursion within cannula cavity 20. With a preselected gas pressure and flow rate set at gas inlet port 100 of device 90, the above-described process of gas filling, venting and flow control occurs automatically at a corresponding rate, resulting in periodic reciprocation of inner cannula 10''' relative to hand-holdable housing 2. In turn, this periodic reciprocation of inner cannula 4' results in periodic displacement of the general location of aspiration occurring along the length of the cannula assembly.

Referring to FIGS. 9A through 9F, there is illustrated yet another embodiment of the liposuction device of the present invention. In general, liposuction device 1G has a pistol-shaped housing 110 which comprises a barrel portion 111 and a detachable handle portion 112. Instead of using a reciprocating piston motor to translate inner cannula 4' relative to housing 100, this embodiment utilizes a rotary-type motor 113. In operative association with a cam mechanism, generally indicated by reference numeral 114, rotary-type motor 113 causes actuation element 115 to cyclically slide back and forth and cause inner cannula 4' to periodically reciprocate relative to barrel portion 111 of the pistol-shaped housing.

Figure 9B:
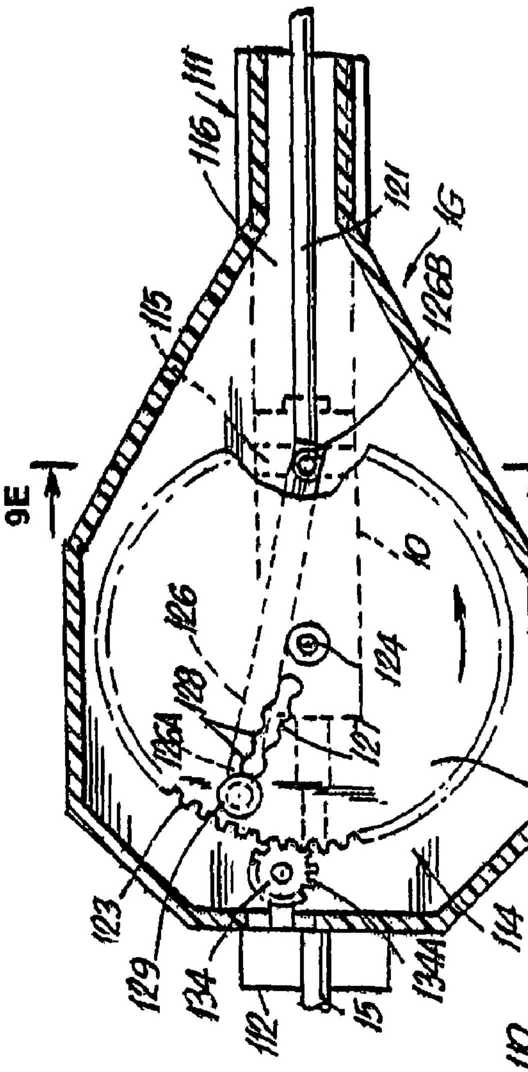
FIG. 9B is a cross-sectional, partially broken away view of the liposuction device of the present invention taken along line 9A-9B of FIG. 9A, showing the cam mechanism of the present invention.
Figure 9D:
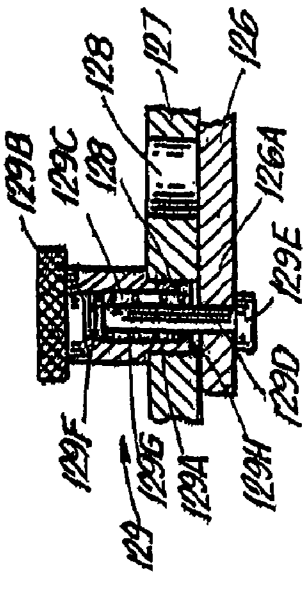
FIG. 9D is a cross-sectional view of a portion of the inner cannula excursion control means shown in FIGS. 9B and 9C.
Figure 9A:
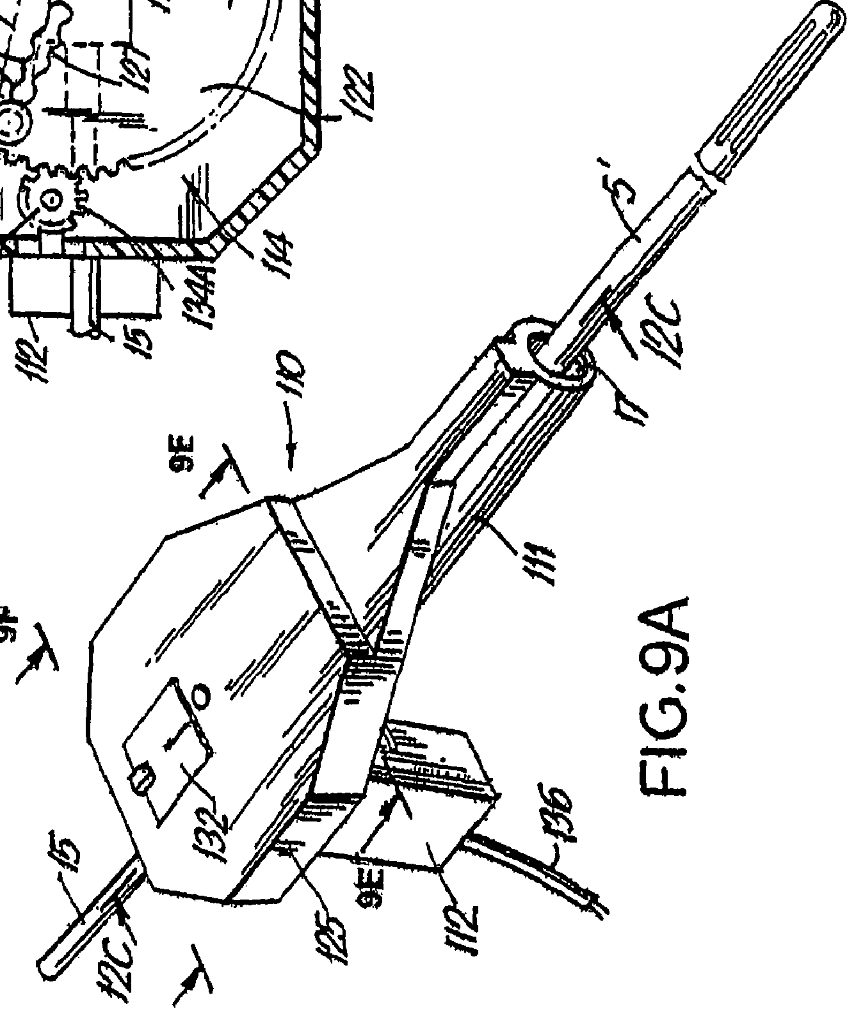
FIG. 9A is a plan cross-sectional view of another embodiment of the liposuction device of the present invention, having a hand-holdable housing realized in the form of a pistol-shaped structure having detachable barrel and handle portions.
Figures 9C, 9E, 9F:
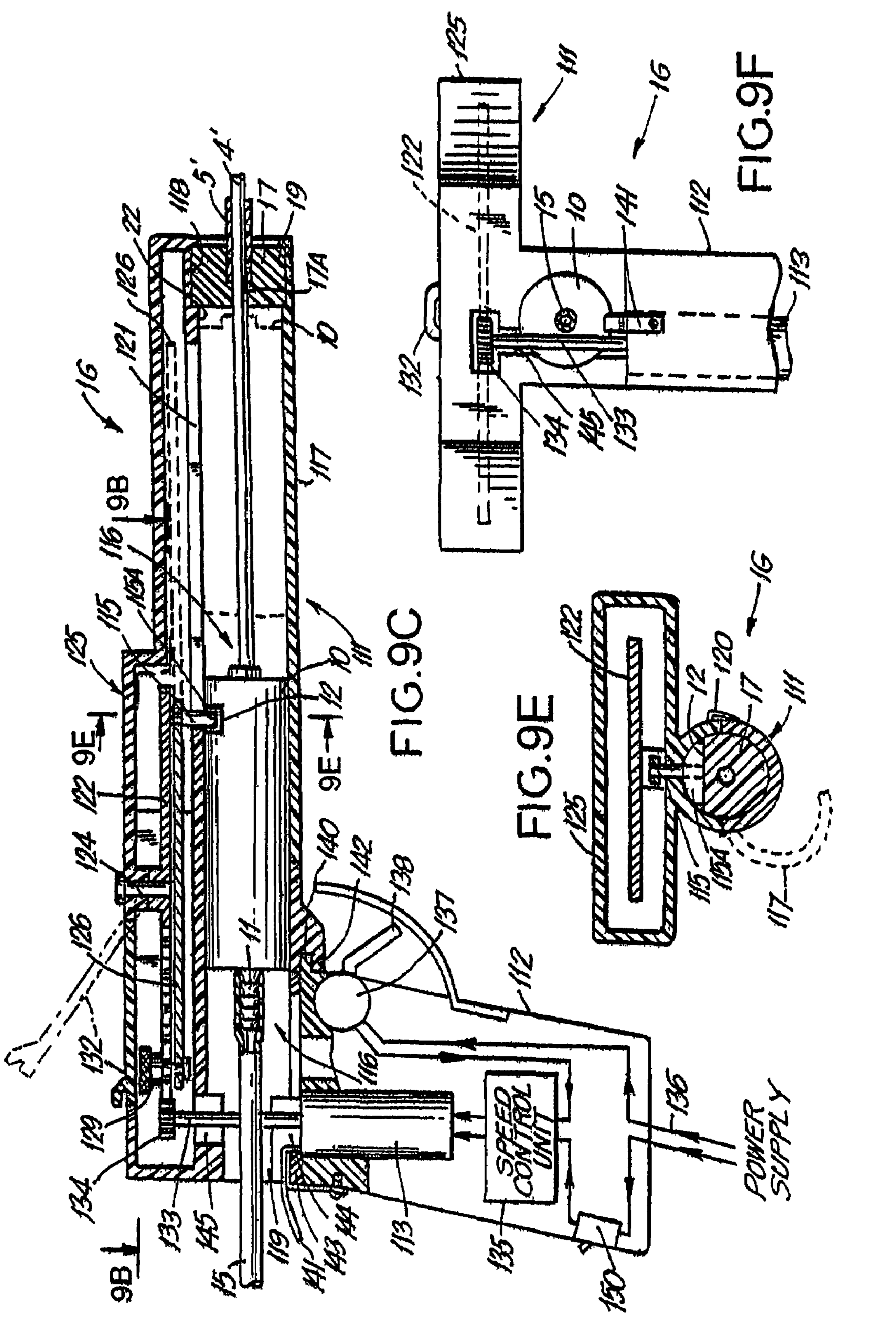
FIG. 9C is an elevated cross-sectional view of the liposuction device of the present invention, taken along line 9C-9C of FIG. 9A, showing the inner cannula disposed at a first position within the cannula cavity of the hand-holdable housing, and the rotary motor and speed control unit in the handle portion thereof.
FIG. 9E is a cross-sectional view of the liposuction device of the present invention taken along line 9E-9E of FIG. 9A, showing the rotary drive wheel of the cam mechanism in operable association with the actuation element which projects through the cannula cavity and is engaged in the slotted base portion of the inner cannula, and also showing in phantom lines the cover panel of the barrel portion disposed in an open configuration permitting insertion or removal of the inner and outer cannulas of the present invention.
FIG. 9F is an elevated partially broken away rear view of the barrel portion of the liposuction device taken along line 9F-9F of FIG. 9A.

As illustrated in FIGS. 9B through 9D, barrel portion 111 of the housing comprises a cannula cavity 116 adapted for slidably receiving cylindrically-shaped base 17 of inner cannula 4', in a manner described hereinabove. Cannula cavity 116 is also provided with a longitudinally extending access opening, over which a hingedly connected cover panel 117 is provided. As illustrated in FIG. 9E, cover panel 117 facilities insertion of the cannula assembly into, and removal of the cannula assembly from, cannula cavity 116 in a manner similar to that described in connection with liposuction instrument 1A of FIGS. 1A through 1C, in particular. As illustrated in FIG. 9C in greater detail, inner cannula base 10 is adapted to be received within cannula cavity 116 and outer cannula base flange 19 releasably received within annular recess 118 formed in cannula cavity wall 22.

To install inner cannula 4' into cannula cavity 116, semi-flexible transparent tubing 15 is connected to inner cannula outlet port 11. Then cover panel 117 is opened and tubing is fed out through rear port 119 of the barrel portion, as illustrated in FIGS. 9C and 9F. Inner cannula base 10 is then slid into cavity 116 with extensional portion of actuation element 115 received in notch 12. Then outer cannula 5' is slid over the distal end of inner cannula 4' until outer cannula base 17 is received within annular recess 118. Thereafter, as shown in FIG. 9E, cover panel 117 is snapped closing using, for example, a spring biased locking device 120, of the type previously described above. Removal of inner and outer cannulas simply involves a reversal of the above procedure.

Alternatively, using spring biased actuation elements and inner and outer cannulas of the type shown in FIGS. 4A and 4B, barrel portion 111 can be realized without necessity of hinged cover panel 117. In such an alternative embodiment, the inner and outer cannulas can be snap-fitted into and pulled out of cannula cavity 116 in a manner similar to that described hereinabove.

As illustrated in FIGS. 9B through 9F, barrel portion 111 houses cam mechanism 114 which is operably associated with (i) rotary motor 113 contained within the handle portion, and (ii) actuation element 115 which slidably passes through a longitudinal slot 121 formed within the upper wall of cannula cavity 116. As in the other previously described embodiments, actuation element 115 includes extension 115A that passes through elongated slot 121 and is received within notch 12 formed in inner cannula base 10. In addition, cam mechanism 114 of the illustrated embodiment inherently embodies gear reduction. In this way, a high angular shaft velocity of rotary motor 113, can be efficiently transformed into reciprocational strokes of the cannula, occurring at a substantially lower rate. With such an arrangement, as rotary motor 113 is caused to rotate under either gas pressure or electrical power, actuation element 115 is caused to reciprocate within elongated slot 121 by way of cam mechanism 114, and thereby cause inner cannula 4' to periodically reciprocate relative to housing 110. This motion results in periodic displacement of the general location of aspiration occurring along the length of the cannula assembly.

As illustrated in FIGS. 9B and 9C, cam mechanism 114 of the preferred embodiment comprises a drive wheel 122 having a first predetermined number of gear teeth 123 disposed thereabout. Drive wheel 122 is rotatably mounted to a shaft 124 mounted through an opening in the top panel of an accommodating section 125 of the barrel portion. Cam mechanism 114 also includes a connective element 126 having first and second ends 126A and 126B, respectively. First end 126A of the connective element is pivotally attached to the drive wheel 122 at a point disposed away from the axial center 124, whereas second end 126B is pivotally connected to actuation element 115 as shown. In order to adjust the distance away from the axis of rotation 124 at which the first end for the connective element is pivotally attached, a radially formed slot 127 is formed in drive wheel 122. A plurality of widened circular apertures 128 are disposed along radial slot 127 as shown in FIGS. 9B and 9D. In this way, a spring-loaded cylindrical pin 129 passing through the first end of connective element 126, can be selectively locked into one of apertures 128 by pulling upwardly upon pin 129 and setting its cylindrical base 129A into the desired aperture 128. In FIG. 9D, pin 129 is shown to further include pin head 129B, a hollow bore 129B, and an axle 129D having heads 129E and 129F. As shown, a spring 129G is enclosed within bore 129C about axle 129D and between head 129F and an inner flange 129H. By selectively locking the first end 126A of connective element 126 into a particular circular notch 128 using springloaded pin 129, the distance of the first end of the connective element from axial center 124 can be set, and thus the amount of inner cannula excursion (and effective aspiration aperture displacement) thereby selected. To permit access to spring-loaded pin 129, the top panel of accommodating portion 125 of the housing is provided with a hinged door 132 that can be opened and snapped closed as desired.

As illustrated in FIGS. 9B and 9C, handle portion 112 of the housing encloses a substantial portion of rotary motor 113 whose shaft 133 projects beyond the handle portion and bears a gear wheel 134. As shown, gear wheel 134 has a second predetermined number of gear teeth 134A disposed circumferentially thereabout, which mesh with drive wheel teeth 123. Notably, to permit the rear portion 119 of cannula cavity 116 to extend all the way towards the rear of the barrel portion for passage and exit of aspiration hose 15, shaft 133 of the motor is mounted off center of handle portion 113, as shown in FIGS. 9C and 9F.

Rotary motor 113 is preferably an electric motor whose shaft speed is controllable by the voltage applied to its terminals. Such speed control can be realized by a conventional speed control circuit 135 connected between motor 113 and a conventional 110-115 volt, 50-60 Hertz power supply. As illustrated in FIG. 9C, conventional electrical cord 136 and on/off power switch 150 can be used to connect control circuit 135 and the power supply. Control over the output voltage produced from speed control circuit 115 and provided to electrical motor 113, can be adjusted, for example, by changing the resistance of a potentiometer 137 which is operably connected to the speed control circuit. As shown in FIG. 6C in particular, this potentiometer 137 can be embodied within a trigger mechanism 138 which is connected, for example, to handle portion 112 of housing 110. By pulling trigger 138, the speed of rotary motor 113 can be controlled, and consequently, so too the rate of reciprocation of inner cannula 4' relative to outer cannula 5', and thus the rate of displacement of the effective aspiration apertures.

To connect handle portion 112 to barrel portion 111 and permit disconnection therebetween for cleaning, sterilization and general service, handle portion 112 is provided with flange 140 and thumb-operable spring element 141. Barrel portion 111, on the other hand, is provided with slot 142, catch 143, and cavity 144. To connect handle portion 112 to barrel portion 111, shaft 133 is vertically passed through channels 144 and 145 until gear 134 is slightly below the plane of drive wheel 122. Then, spring element 141 is inserted within cavity 144 while flange 140 is guided into slot 142. By pushing the rear portion of handle 112 in the longitudinal direction of cannula cavity 116, spring element 141 will snap over and clasp catch 143 as shown in FIG. 12C. In this configuration, handle portion 112 is secured to barrel portion 111 and gear teeth 123 will mesh with drive wheel teeth 134A. To disconnect handle portion 112 from barrel portion 11, the surgeon's thumb simply depresses spring-element 141 downwardly and then, by moving handle portion 112 slightly rearwardly, then downwardly, flange 140 is dislodged from slot 142 and motor shaft 133 can be withdrawn from channels 144 and 145. In this disassembled state, handle portion 110 and barrel portion 112 can be individually cleaned and sterilized using conventional procedures known in the surgical instrument art.

Liposuction device 1G described above employed an electric rotary motor to effectuate reciprocation of inner cannula 4' relative to housing 110. However, in an alternative embodiment, it is possible to effect reciprocation of the outer cannula while the inner cannula is stationary with respect to the housing, as shown in FIGS. 6A through 7. Also, it is possible to employ a conventional gas driven rotary motor in lieu of electric rotary motor 113. In such an embodiment, trigger 138 can be operatively associated with a gas flow control valve. Thus, by controlling the rate of gas flow to the gas rotary motor upon actuation of trigger 138, the angular velocity of shaft 133 can be controlled and thus the rate of reciprocation of inner cannula 4' relative to housing 110.

Having described various illustrated embodiments, it is appropriate at this juncture to describe the method of the present invention using, for purposes of illustration only, the liposuction instrument 1C illustrated in FIG. 5.

In general, the surgeon prepares in a conventional manner, the area of skin below which liposuction is to be performed. Typically, this entails marking various zones where radial displacement of the aspiration apertures is to occur. Liposuction instrument 1C of the present invention is assembled as described above so that aspiration apertures 8A', 8B' and 8C' of cannula assembly 3' are in communication with a vacuum source (not shown). A small incision is then made in the patient's skin in a conventional manner, and the distal portion of the cannula assembly is inserted into a premarked radial zone. As pressurized gas is provided to piston motor 6, inner cannula 10 will automatically reciprocate causing the general location of the suction apertures to be automatically displaced along each tunnel of fatty tissue. During the operation of the instrument, the surgeon's hand holding the liposuction instrument is maintained essentially stationary with respect to the patient. Fatty tissue is aspirated through the periodically displaced aspiration apertures, and transferred into a reservoir tank operably associated with the vacuum source.

As deemed necessary, the surgeon can selectively increase the rate of aspiration aperture travel along the distal end of the cannula assembly. This can be achieved by a foot-operated gas flow control device 78 which controls the rate of gas flow to piston motor 6. Also, the amount of inner cannula excursion (i.e., aspiration aperture travel) can also be selected by adjusting the compliance of spring 40 through rotation of threaded element 42.

In the illustrative embodiments described hereinabove, the outer cannula has been made from an electrically non-conductive material (i.e., achieving electrical isolation between the cauterizing electrodes supported on the outer cannula, and electrically conductive inner cannula). The inner cannula has been made from stainless steel, offering the advantage of being easily cleaned and sterilizable. The plastic outer cannula offers the advantages of electrical insulation, low manufacturing cost and disposability. Preferably, when making the outer cannula from a suitable plastic material, injection moulding processes can be used.

Figures 10, 10A:
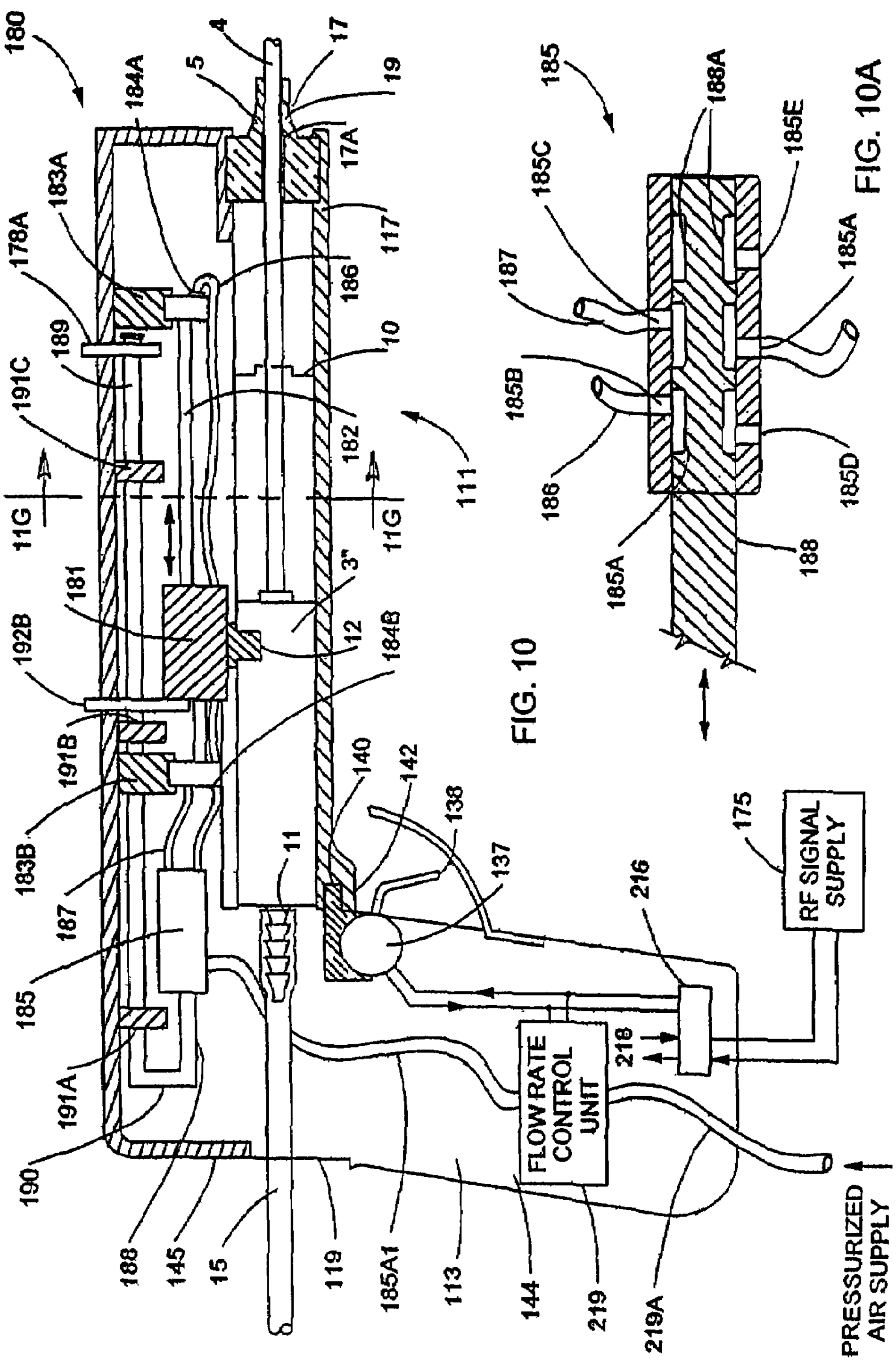
FIG. 10 is a cross-sectional view of another illustrative embodiment of the liposuction device of the present invention, wherein a liposuction device of the present invention is provided, having a double-acting air-powered cylinder with a magnetically-coupled actuator and the electro-cauterizing cannula assembly of the present invention is installed.
FIG. 10A is a cross-sectional schematic diagram of the air flow control device employed in the liposuction device shown in FIG. 10, in which the control valve thereof is mechanically linked to the reciprocating piston contained within the cylinder-style reciprocator within the housing of the liposuction device.

In FIG. 10, an alternative embodiment of the liposuction instrument of FIG. 9 is shown. While this embodiment of the liposuction instrument hereof 180 is similar to the embodiment shown in FIG. 9, there are a number of differences. For example, an actuator 181 magnetically-coupled to an air powered cylinder 182 is used to reciprocate the base portion 10 of the inner cannula of its electro-cauterizing cannula assembly. The magnetically-coupled air powered cylinder and actuator subassembly (182, 181) can be realized as Model No. MG 038 commercially available from Tol-O-Matic, Inc. of Hamel, Minn. As shown in FIG. 10, the ends of the air powered cylinder 182 are supported by an external guide and support system comprises brackets 183A and 183B, which are integrated with interior portions of the hand-holdable housing. The actuator block 181, which is mounted about the cylindrical shaft of the cylinder 182, reciprocates between the support brackets 183A and 183B in response to pressurized air (gas) flowing into its first air input/output port 18A, then the second air input/output port 184B, repeatedly in an alternating manner, causing the actuator 181 to reciprocate along the cylinder 182. Such pressurized air streams are provided by an air-flow control device 185.

As shown in FIG. 10A, the air flow control device 185 has one air supply port 185A, first and second air output/return ports 185B and 185C, and first and second air exhaust ports 185D and 185E. Air supply port 185A is supplied with pressurized air through tubing 185A1 connected to flow rate control unit 219 which is controlled by electrical signals produced by trigger 138 when pulled to a particular degree of angular function of deflection. The control unit 219 is to control the flow of air from supply tubing section 219A connected to an external source of pressurized air. The first and second air output/return ports 185B and 185C, are arranged in fluid communication with the first and second air input/output ports 184A and 184B of the cylinder 182, respectively, by way of air tubing sections 186 and 187.

As shown in FIG. 10A, air-flow control device 185 has an air flow control shaft 188 with air flow directing surfaces 188A. Air flow control shaft is slidably supported within the housing of the device. The function of the flow control shaft is to commute air flow between its various ports described above in response to the position of the actuator 181 along the cylinder 182 during device operation. In order to achieve such functions, the air-flow control shaft 188 of the illustrative embodiment is mechanically coupled to an actuator stroke control rod 189 by way of a mechanical linkage 1990. Linkage 190 is supported by brackets 191A, 191B and 191C and secured to the interior of the hand-holdable housing. Along the actuator stroke control rod 189, a pair of actuator stops 192A and 192B are disposed. In the illustrative embodiment, stops 192A and 192B are realized as slidable rods which are adapted to lock into different detected positions along the stroke control rod 189 when the surgeon presses the top thereof (located outside of the housing) downwardly and then in the direction of adjustment, releasing the control stop at its desired location. In some embodiments, it may be desirable to fix one of the control stops while allowing the other control stop to be adjustable along a selected portion of the length of the stroke control rod 189. In alternative embodiments, actuator stroke control can be realized using other types of adjustment mechanisms including, for example, externally accessible adjustment screw mechanism, in which adjustment (rotation) of a single knob or thumb-wheel enables the surgeon to set the stroke length of the inner cannula and thus the aspiration aperture thereof; electronic control mechanisms, in which actuation of an electronic or electrical device, such as foot pad or electrical switch enables the surgeon to translate the position of one or both of the stroke control stops by electro-mechanical means (including linear motors, geared rotary motors and the like.)

Figures 11A, 11B, 11C, 11D:
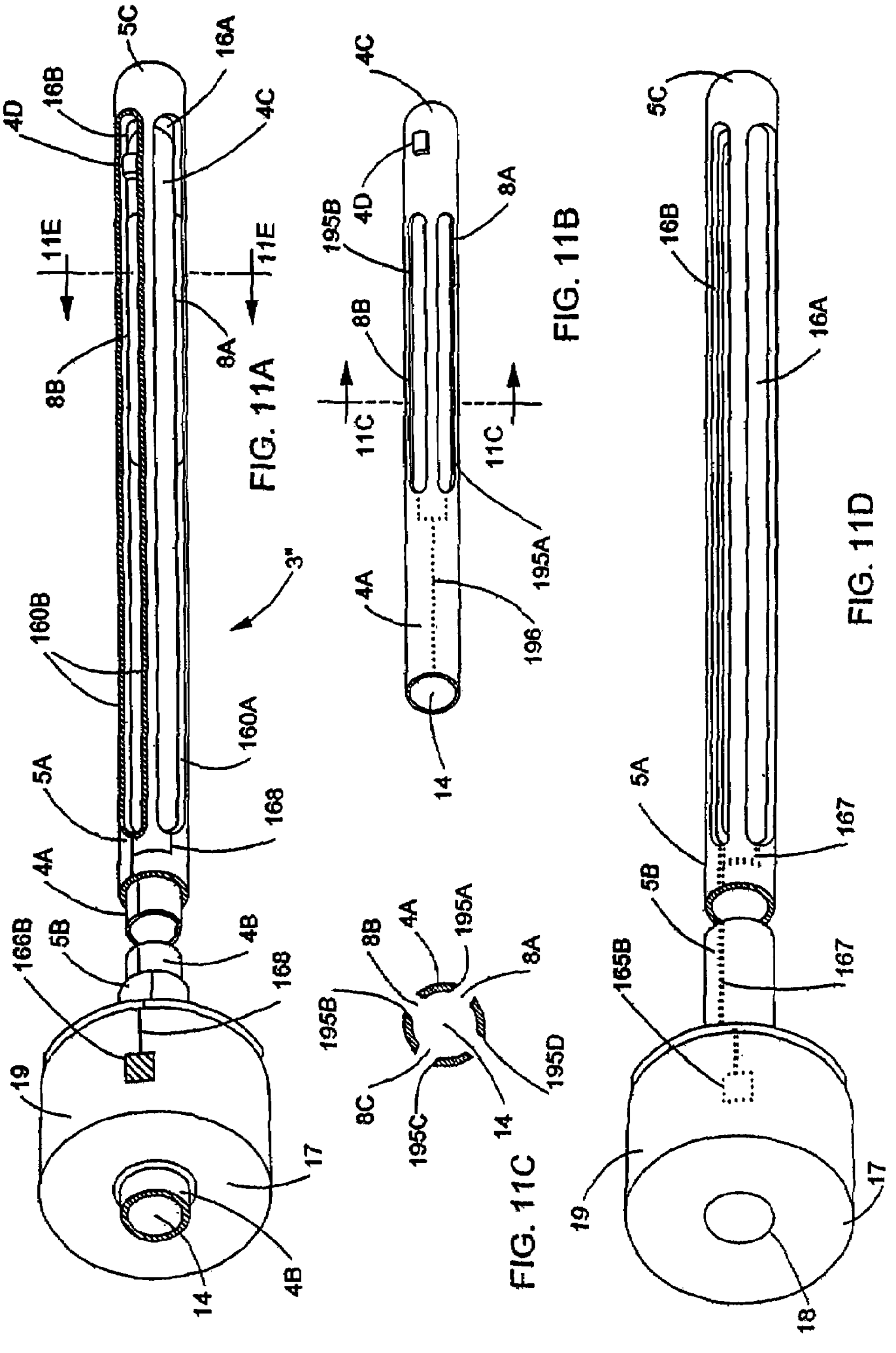
FIG. 11A is a perspective, partially broken away view of the electro-cauterizing cannula assembly of the present invention installed in the liposuction instrument of FIG. 10, in which the electrically-conductive inner cannula is adapted to freely undergo sliding movement within the stationary electrically non-conductive outer cannula while electro-cauterization is performed about the aspiration apertures thereof under the control of the surgeon.
FIG. 11B is a perspective view of the distal end of the inner cannula shown in FIG. 11A.
FIG. 11C is a cross-sectional view of the electrically-conductive inner cannula taken along line 11C-11C of FIG. 11B.
FIG. 11D is a perspective, partially broken away view of the electrically non-conductive outer cannula shown in FIG. 11A.

As shown in FIG. 10A, the air flow control shaft 188 has two primary positions; a first position, in which pressurized air from the air supply port 185A is directed to flow through the second air output/return port 188C of the air flow control device, along tubing 187 and into the second input/output port 184B of the cylinder 182, while the second input/outlet port 184B of the cylinder is in communication with the first exhaust port 185D of the air flow control device 185 causing inner cannula to project away from the housing; and a second position, in which pressurized air from the air supply port 185A is directed to flow through the first air output/return port 188B of the air flow control device, along tubing 186 and into the first input/output port 184A of the cylinder, while the second input/outlet port 184B of the cylinder is in communication with the second exhaust port 185E of the air flow control device 185, causing the inner cannula to retract inwards towards the housing. By virtue of this arrangement, the actuator 181 is automatically driven back and forth between stroke control stops 192A and 192B along the cylinder stroke rod in response to pressurized air flow into the air flow control device 185. When the electro-cauterizing cannula assembly of FIG. 11A is installed within the cannula cavity of the liposuction device, as described hereinabove, the inner cannula 4 will be caused to reciprocate relative to the outer cannula 5. In the illustrative embodiment, the length of the excursion of the inner cannula 4 is determined by the physical spacing between mechanical stops 192A and 192B. By varying the spacing of these stops along the stroke control rod 182, the maximum excursion of the inner cannula relative to the stationary outer cannula can be simply and easily set and reset as necessary by the surge on.

In FIG. 11A, an electro-cauterizing cannula assembly 3" is shown for use with the liposuction instrument of FIG. 10. In this illustrative embodiment, both the inner and outer cannulas are made of an electrically non-conductive material such a sterilizable plastic. In the embodiment of FIG. 10, hand-holdable housing is preferably made from an electrically non-conductive material. Electrically conductive electrodes 195A, 195B, 195C and 195D are inserted within the inner aspiration apertures 8A, 8B, 8C and 8D and electrical wiring 196 run to the inner cannula base portion 10, wherein an electrical contact pad 197 is embedded. Electrically conductive electrodes 160A, 160B, 160C and 160D are also inserted within the outer aspiration apertures 16A, 16B, 16C and 16D, and electrical wiring 168 run to the outer cannula base portion 19, wherein an electrical contact pad 166B is embedded. An electrical contact pad 176B is also embedded within the base portion recess within the hand-holdable housing.

Figure 11F:
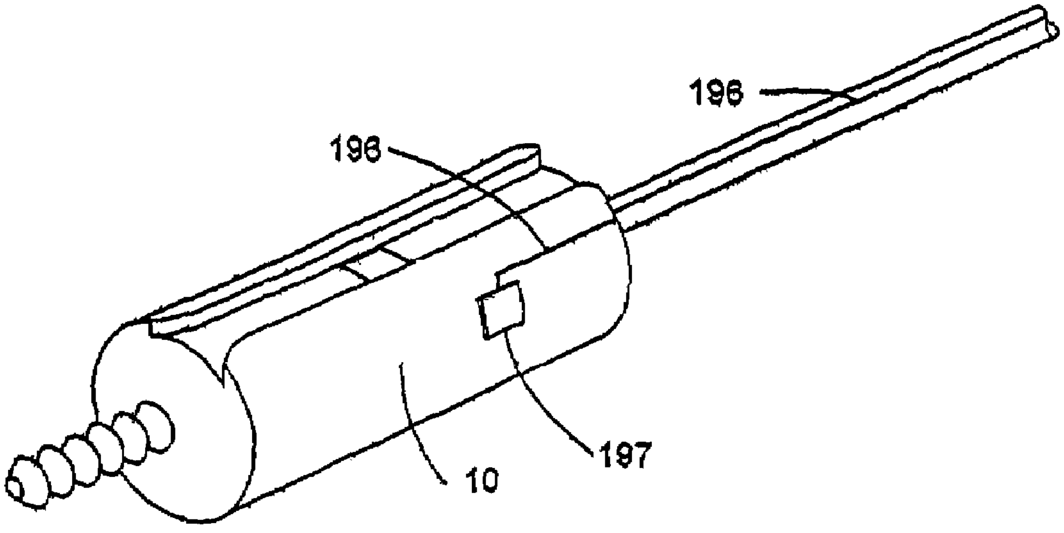
FIG. 11F is a perspective view of the base portion of the electrically-conductive inner cannula shown in FIG. 11 showing an electrical contact pad embedded in the outer surface thereof for conducting the conductive rail embedded in the wall surface of the cannula cavity.
Figure 11G:
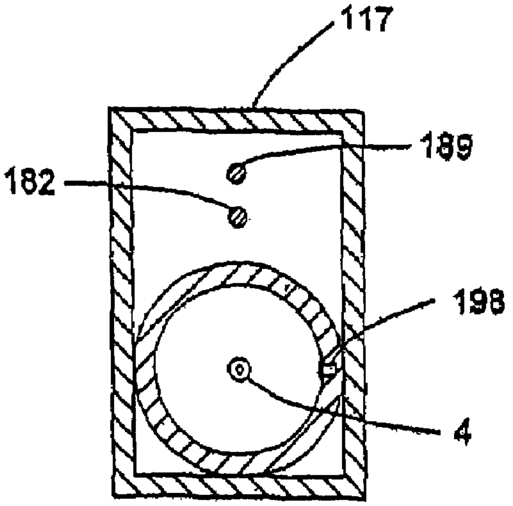
FIG. 11G is a cross-sectional view of the liposuction instrument taken along line 11G-11G of FIG. 10.

As shown in FIGS. 10 and 11, an electrical contact rail 198 is embedded within the side wall surface of the cannula cavity so that electrical contact pad 197 or base portion 10 of the inner cannula establishes electrical contact therewith to apply RF (supply/return) power signals to the electrodes in the inner cannula during liposuction operations. In such circumstances, two sets of electrical connections occur. Firstly, the base portion 10 of the inner cannula is securely engaged by the actuator block 181 (snap-fitting or other suitable means) and the electrical contact pad 197 contact with the electrical rail 198 embedded within the inner side wall surface of the cannula cavity. Secondly, the base portion 19 of the outer cannula is received within the base portion recess of the hand-holdable housing and the electrical contact pad (i.e., RF power supply terminal) 176B embedded therewithin establishes contact with the electrical contact 166B embedded within the base portion of the outer cannula. By virtue of these electrical connections, RF supply potentials are applied to the electrode portions of the inner cannula, while RF return potentials are applied to the electrode portions of the outer cannula, whereby electro-cauterization occurs.

Figures 13A, 13B, 13C, 13D:
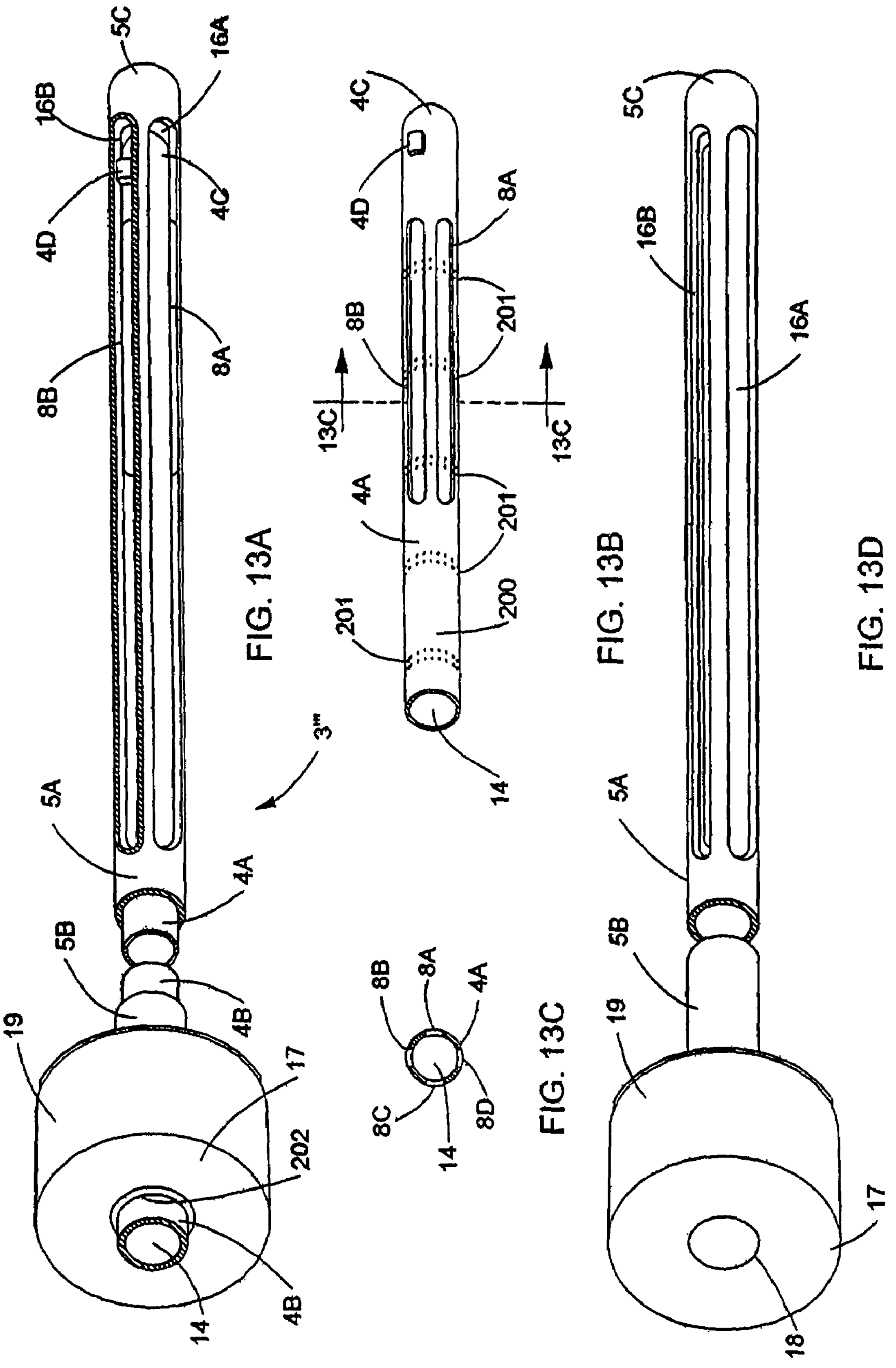
FIG. 13A is a prospective, harshly broken away view of the electrically-conductive outer cannula employed in an alternative embodiment of the electro-cauterizing cannula assembly utilizable in the liposuction device of the present invention with suitable modifications.
FIG. 13B is a prospective view of a distal end of the inner cannula shown in FIG. 13A.
FIG. 13C is a cross-sectional view of the electrically conductive inner cannula taken along line FIG. 13C-13C of FIG. 13A.
FIG. 13D is a prospective harshly broken away view of the electrically conductive outer cannula shown in FIG. 13A, over which an electrically insulating coating such as Teflon is applied to the exterior surface thereof.

In FIG. 13A through 13D, an alternative electro-cauterizing cannula assembly 3''' is shown for use with the liposuction instrument shown in FIGS. 10 and 10A, and readily adaptable for use with other liposuction instruments of the present invention. In this particular illustrative embodiment, both the inner and outer cannulas are made of an electrically conductive material. The hand-holdable housing is made from an electrically non-conductive material (e.g., plastic). Between these electrically conductive cannulas 4 and 5 means are provided for maintaining electrical isolation between the electrically conductive carrier and outer cannula which, during electro-cauterization, are maintained at an electrical potential difference (i.e., voltage) of 800 volts or more. In general, a variety of different techniques can be employed for carrying out this functionality. For example, a thin coating of Teflon$^R$ material 200 can be applied to the outer surface of the outer cannula. Alternatively, a series of electrically-insulating spacer/washers made from Teflon$^R$ ceramic, or like material can be mounted within circumferentially extending grooves formed periodically about the inner cannula to maintain sufficient spacing and thus electrical insulation between the inner and outer cannulas. Preferably, the spacing between each pair of insulating spacers is smaller than the length of the bore 18 formed in the electrically conductive base portion of the outer cannula, as illustrated in FIG. 13A.

The electrical contact rail (i.e., RF power supply terminal) 198 embedded within the cannula cavity establishes electrical contact with the base portion of the inner cannula when the cannula assembly is installed in the housing of the device. Also, electrical contact pad 176B embedded within the recess portion of the housing establishes electrical contact with the base portion of the outer cannula when the cannula assembly is installed within the hand-holdable housing. In the assembled state, two sets of electrical connections occur. Firstly, the electrically conductive base portion of the inner cannula is engaged by the electrical contact rail 198. Secondly, the base portion of the outer cannula is received within the base portion recess and the base portion of the outer cannula establishes contact with the electrical contact 176B embedded within the recess portion. By virtue of these electrical connections, RF supply potentials are applied to the inner cannula, while RF return potentials are applied to the outer cannula. The potential difference(s) between these surfaces about the aspiration apertures enable electro-cauterization of tissue as it is being aspirated through the aspiration aperture moving along the cannula assembly.

In another illustrative embodiment of the present invention, the inner cannula 4 is made of an electrically non-conductive material such as plastic. The outer cannula is made of electrically conductive material (e.g., stainless steel). The hand-holdable housing is made from an electrically non-conductive material (e.g., plastic). Electrically conductive electrodes are inserted within the inner aspiration apertures thereof, and electrical wiring run to the inner cannula base portion, wherein an electrical contact rail is also embedded.

Figures 14, 14A:
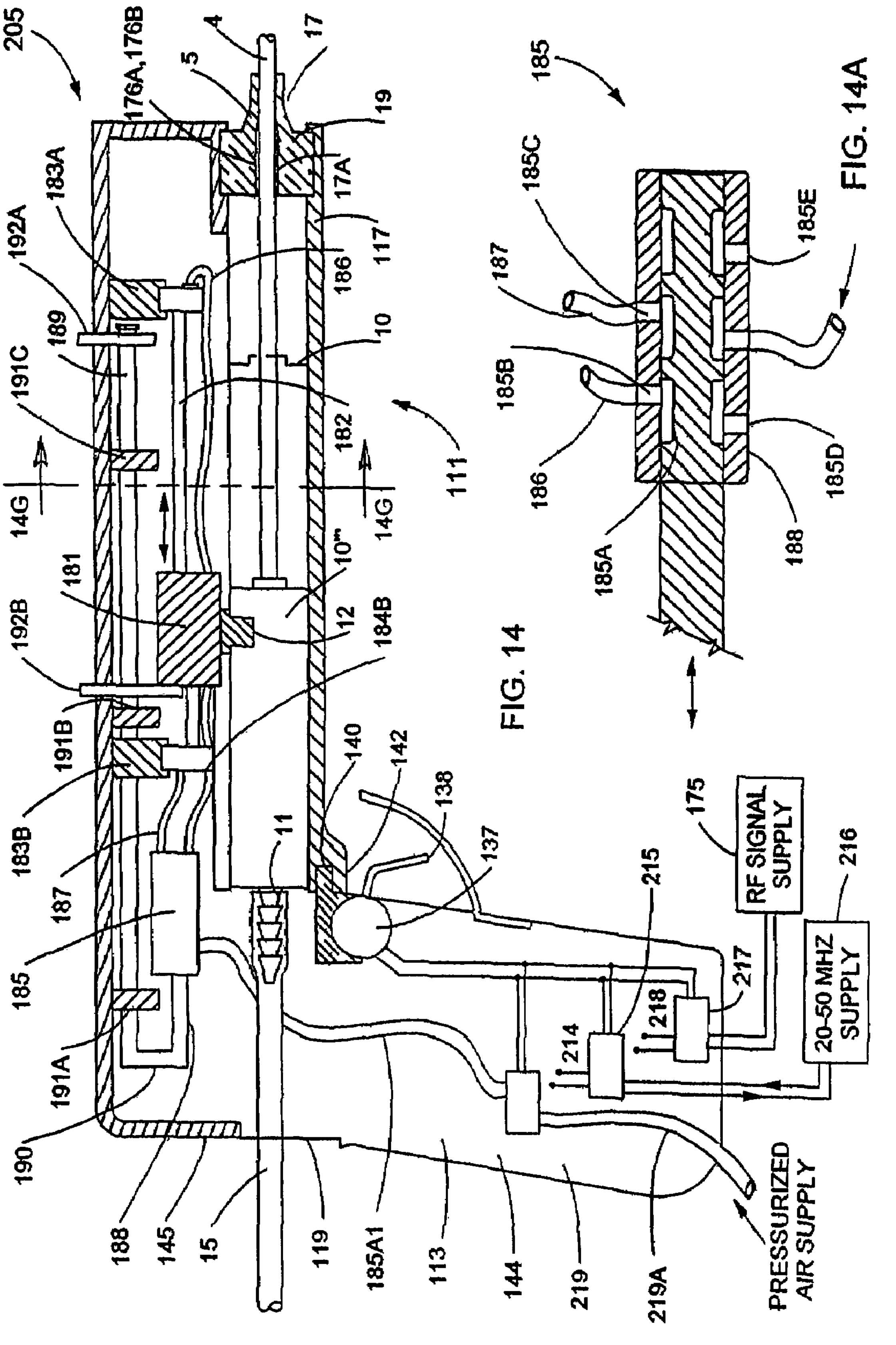
FIG. 14 is a cross-sectional schematic diagram of an alternative embodiment of the electro-cauterizing liposuction instrument of the present invention, wherein the reciprocation means is realized using a cylinder-style actuator powered by a supply of pressurized air.
FIG. 14A is a schematic cross-sectional view of the airflow control device employed within the liposuction instrument of FIG. 14.
Figure 14B:
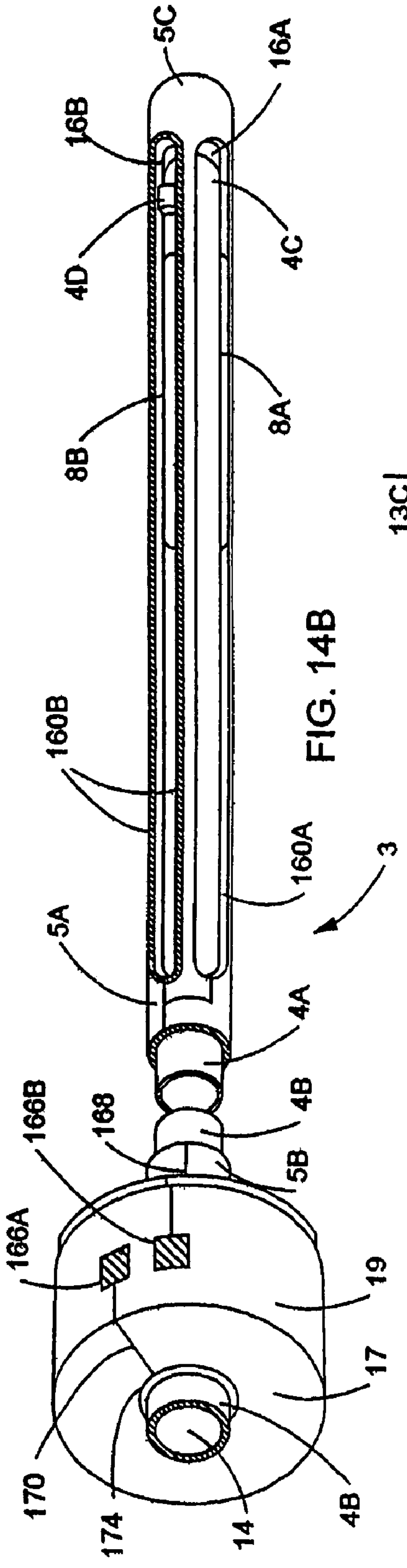
FIG. 14B is a prospective, harshly broken away view of the electrically-nonconductive outer cannula employed in alternative embodiment of the electro-cauterizing cannula assembly utilized in the liposuction instrument of FIG. 14.
Figure 14C:
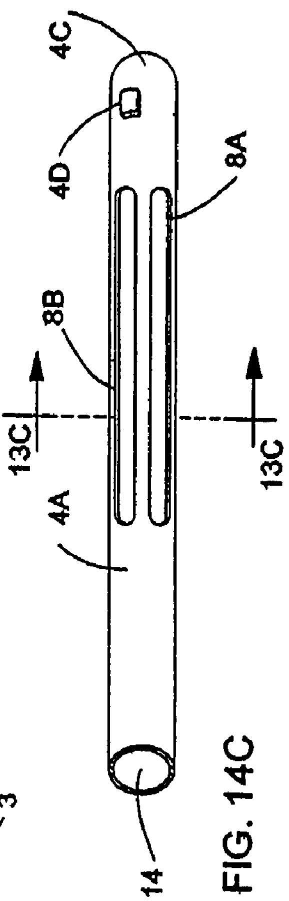
FIG. 14C is a prospective view of a distal end of the inner cannula shown in FIG. 14B.
Figure 14D:
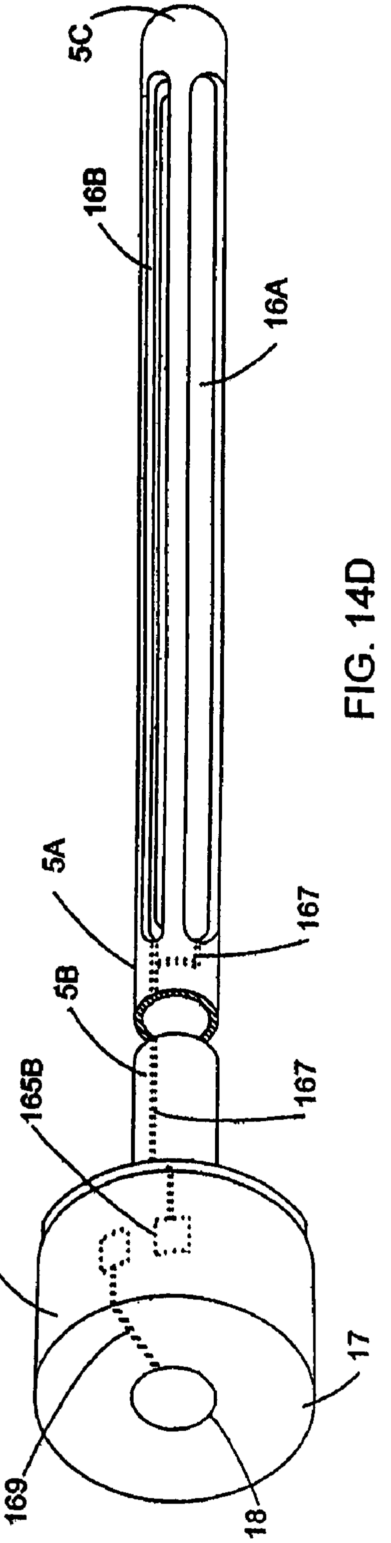
FIG. 14D is a prospective harshly broken away view of the electrically nonconductive outer cannula shown in FIG. 14B, over which an electrically insulating coating such as Teflon is applied to the exterior surface thereof.
Figure 14E:
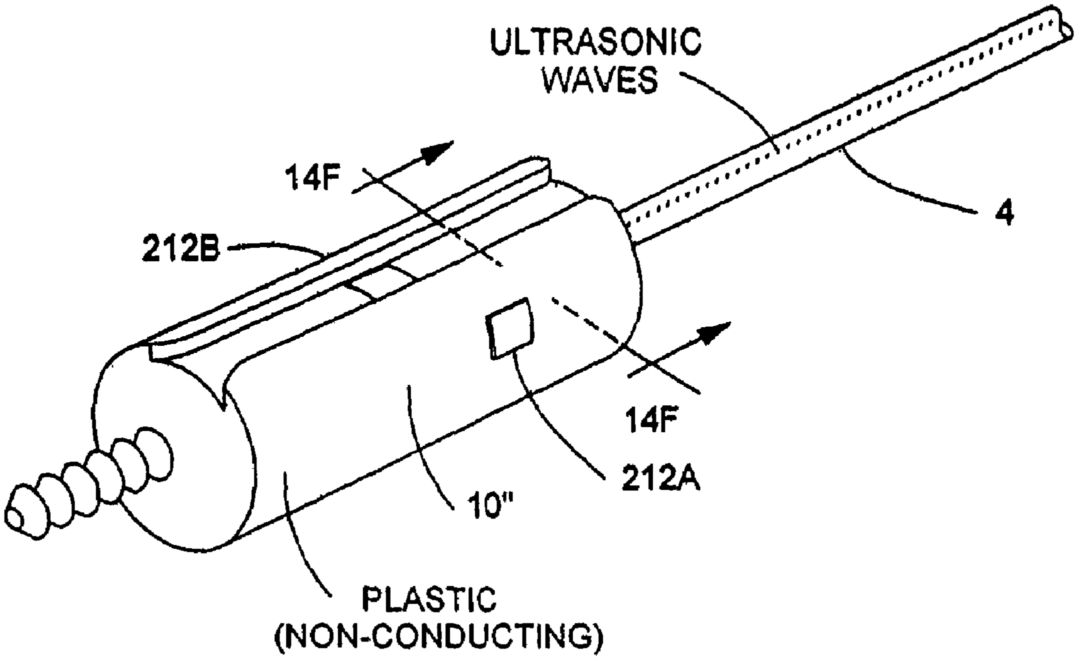
FIG. 14E is a prospective view of the base portion of the inner cannula used in the cannula assembly of FIG. 14B, wherein an electrical contact pad is embedded in the side wall surface thereof of the base portion for engagement with an electrically conductive rail embedded within the side wall surface of the cannula cavity within the liposuction instrument of FIG. 14.
Figure 14F:
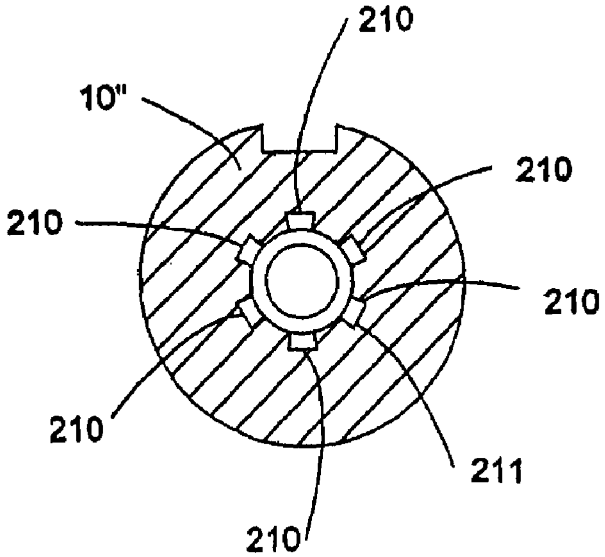
FIG. 14F is a cross sectional view of the base portion of the inner cannula taken along line 14F-14F in FIG. 14E, showing a plurality of piezo-electrical transducers arranged about the lumen of the inner cannula for producing and conducting ultrasonic energy signals for propagation along the length of the inner cannula.
Figure 14G:
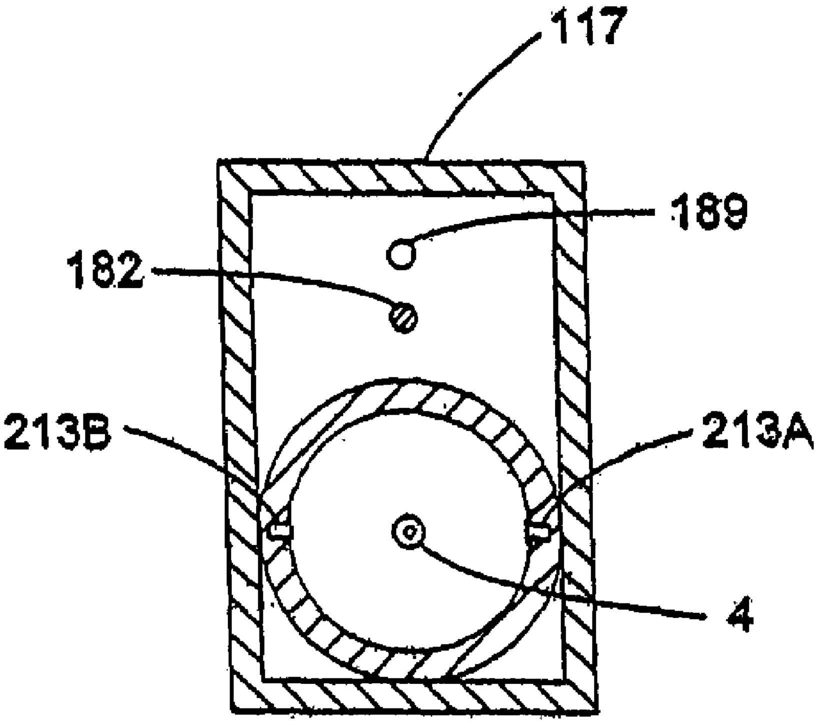
FIG. 14G is a cross sectional view of the liposuction instrument of FIG. 14 taken along line 14G-14G of FIG. 14, showing a pair of diametrically opposed electrically conductive rails embedded within the interior wall surfaces of the cannula cavity of the liposuction instrument, which establish electrical contact with a pair of electrical contact pads embedded within the base portion of the inner cannula and are connected to the array piezo-electric transducers mounted about the outer lumen of the inner cannula.
Figure 15:
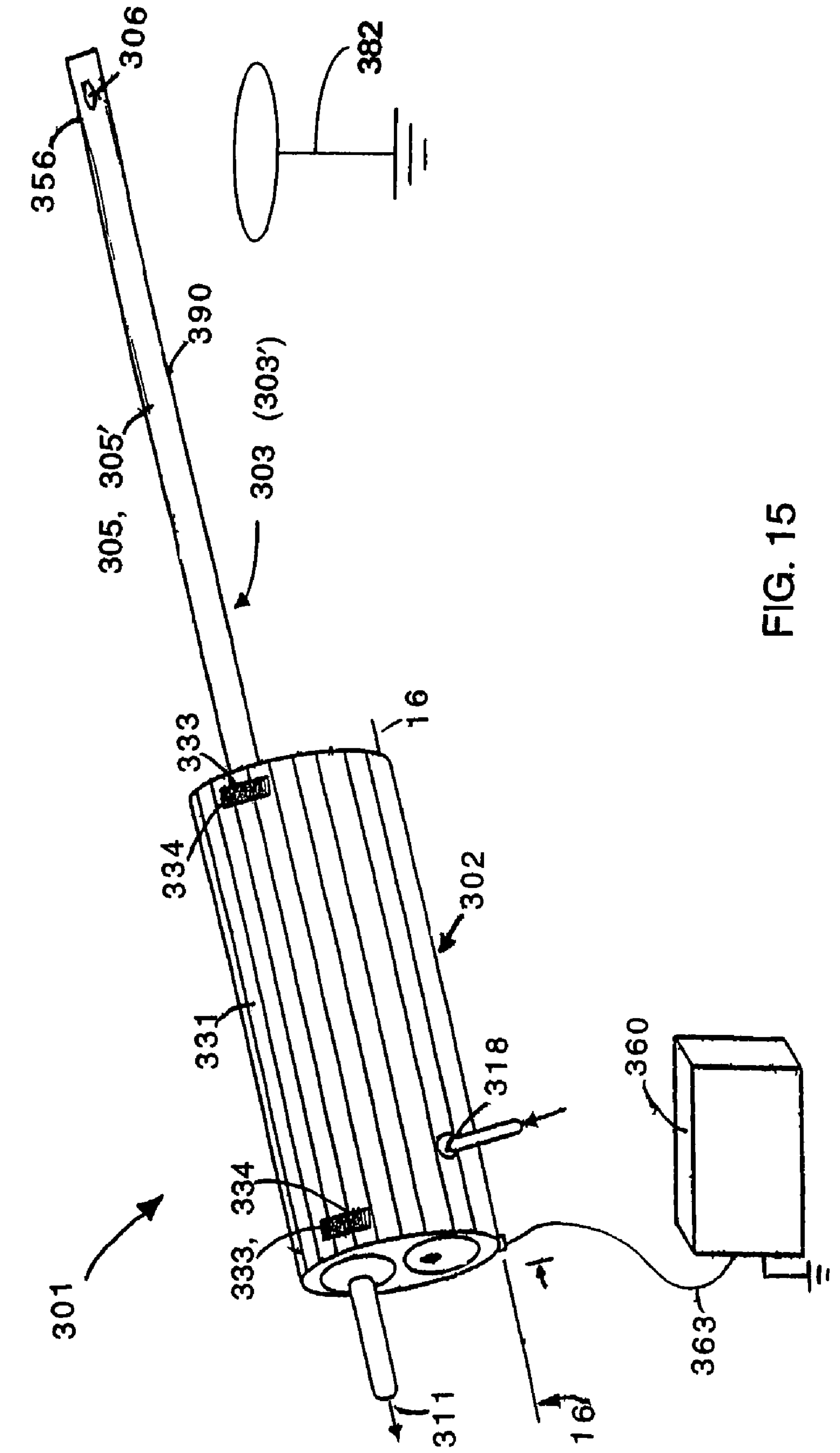
FIG. 15 is a perspective view of another embodiment of the liposuction device of the present invention provided with monopolar electrocautery electrode structures along the distal portion of a single cannula assembly.

As shown in FIG. 14G, an electrical contact rail 213A is also embedded within the side wall of the cannula cavity. An electrical contact pad embedded within the recess of the plastic hand-holdable housing establishes electrical contact with the base portion of the electrically conductive outer cannula. Thus, when the cannula assembly is installed within the hand-holdable housing, two sets of electrical connections occur. Firstly, the base portion of the inner cannula is engaged by the actuation means and the electrical contact pad therewithin establish contact with the electrical contact embedded within the base portion of the outer cannula. By virtue of these electrical connections, RF supply potential are applied to the electrode portions of the inner cannula, while RF return potentials are applied to the electrode portions of the outer cannula.

In yet other alternative embodiments of the present invention, hemostasis can be carried out in the powered liposuction instruments hereof by producing ultrasonic energy (having a frequency of about 50 kilohertz) and delivering the same to the aspiration aperture regions of the cannula assembly during liposuction procedures. Such ultrasonic energy will cause protein coagulation of aspirated tissue in the regions of the aspiration apertures. When the frequency of the ultrasonic energy is reduced to about 20-25 kilohertz, liquefaction or lipolysis of the aspirated tissue will occur. Such modes of operation can be added to any of the electro-cauterizing liposuction instruments of the present invention, or to liposuction instruments with electro-cauterizing capabilities.

In FIGS. 14 through 14C, a preferred embodiment of the ultrasonic cauterizing liposuction instrument of the present invention is shown. In general, the embodiment shown in FIGS. 14 through 14C is similar to the liposuction instrument of FIG. 10, except that it includes several additional means which enable it to effect protein coagulation (and thus hemostasis) during liposuction using ultrasonic energy having a frequency of about 50 kilohertz and sufficient power. As shown, a set of piezo-electric crystals 210 are embedded about the lumen of the inner cannula and encased within the base portion of the inner cannula made of plastic.

As shown in FIG. 14, an electrical signal generator 216 external to the liposuction device is provided for supplying electrical drive signals to terminals 214 via control circuit 215 when it is enabled by manual actuation of trigger 138. The electrical signal generator 216 should be capable of producing electrical signals having a frequency in the range of about 15 to 60 kHz, at a sufficient power level. Any commercially available signal generator, used in medical applications, can be used to realize this system component. The electrical signals produced from generator 216 are applied to the terminals of the piezo-electric transducers embedded within the electrically non-conductive base portion of the inner cannula.

When the generator 216 is switched to produce signals in range centered about 20 kHz, these signals are delivered to the array of piezo-electric transducers embedded within the base portion of the inner cannula. These drive signals cause the piezo-electric transducers to produce ultrasonic signals in substantially the same frequency range to propagate along the surface of the inner cannula and out the inner and outer aspiration apertures, enabling lipolysis or liquefaction of aspirated fat tissue.

When the generator is switched to produce signals in range centered about 50 kHz, these signals are delivered to the array of piezo-electric transducers embedded within the base portion of the inner cannula. These drive signals cause the piezo-electric transducers to produce ultrasonic signals in substantially the same frequency range to establish standing waves within the inner cannula which propagate out the apertures of inner and outer cannula, enabling coagulation of protein molecules within aspirated tissue, thus achieve hemostasis.

While carrying out lipolysis using ultrasonic energy producing means within the liposuction device hereof, the surgeon may also desire to conduct hemostasis by coagulating protein molecules within tissue being aspirated. As shown in FIG. 14, by pulling trigger 138, control circuit 217 automatically commutes RF supply and return signals from the RF signal supply unit 175 to power supply terminals 218 which, in turn, are connected to contact pads 176A and 176B embedded within recess 17A, supporting the base portion of the outer cannula with respect to the hand-holdable housing.

As shown in FIGS. 10 and 14, a flow control switch 219 is provided within the handle of the housing in order to enable the flow of pressurized air from air supply to the reciprocation means (e.g., cylinder 182, etc.) only when manually actuated trigger 138 is manually actuated (or a foot pedal is depressed). When the trigger 138 is pulled, an electrical signal is sent to the flow control switch 219 which, in turn, permits a selected amount of pressurized air to flow into the reciprocation device (e.g., cylinder 182). The trigger switch 138 can have a number of positions, at which different electrical signals are produced for enabling flow control switch 219 to allow pressured air to flow to the reciprocation means 182 at different flow rates. This can be used to control the rate of reciprocation of the inner cannula relative to the outer cannula, providing the surgeon with additional control over the tissue aspiration process.

Notably, an improved degree of surgical control and user safety is provided by the liposuction instrument of the present invention described above.

In particular, control circuit 217 prevents the liposuction instrument hereof from carrying out cauterization along the length of its cannula assembly, unless the cannula is reciprocating and/or aspirating. This condition is detected when the trigger 138 is pulled to a particular degree of angular deflection. The reason for providing such control over the electro-cauterization functionality of the liposuction device hereof is to prevent inadvertent burning of tissue during liposuction and like procedures.

The function of the control logic circuit 215 is to enable the commutation of 20-25 kilohertz electrical signals between the generator 216 and the power supply rails 213A and 213B (to energize the piezo-electric transducers 210 in the base portion of the inner cannula) only when aspirated tissue is flowing through the inner cannula. This condition is detected when the trigger 138 is pulled to a particular degree of angular deflection.

The electro-cauterization electrodes of the liposuction devices hereof can be controlled in a variety of different ways. One way would be to continuously enable RF-based electro-cauterization during sensed tissue aspiration. In such "continuously-enabled" embodiments of the present invention, there will typically be no need for external switches to activate the electro-cauterizing electrodes embodied within the cannula assembly of the present invention.

Another way would be to enable RF-based electro-cauterization by way of switching RF supply and return signals to the electrodes during sensed tissue aspiration and supply of an activation signal by the surgeon. Generation of the activation signal can be realized by manually actuating a second trigger, or pushing a button, or depressing a foot pedal, external to the hand-supportable housing, or by automatically detecting a particular condition along the aspiration channel of the device or elsewhere therein.

While the liposuction instruments described above have been shown to include four symmetrically arranged aspiration apertures, it may be desired in particular applications to provide a cannula assembly having inner and outer cannulas with one, two or three aspiration apertures, rather than four as shown in the illustrative embodiments.

In some applications it may be desired to provide a cannula assembly having a pair of diametrically opposed aspiration apertures, and an outer cannula with a single aspiration aperture. The outer cannula assembly can be adapted to be rotatable in one of two angular positions about the inner cannula. In the first position, the single aspiration aperture formed in the outer cannula is aligned in registration with the first aspiration aperture along the inner cannula. When rotated into its second angular position, the single aspiration aperture of the outer cannula is aligned in registration with the second aspiration aperture along the inner cannula. The surgeon can easily switch the outer cannula between its first and second angular positions by rotating a small radially extending projection, adjacent the hand-holdable housing, in either a clockwise or counter-clockwise direction to align the aspiration aperture on the outer cannula in registration with the selected aspiration aperture on the inner cannula. This feature of the present invention provides the surgeon with the option of changing which side of the distal end of the cannula assembly is enabled to aspirate tissue during a liposuction procedure without the necessity of removing, repositioning and reinserting the cannula assembly within the housing. This technical feature can be used in conjunction with both electro-cauterizing as well as ultrasonic cauterizing functionalities of the present invention described above. When this aspiration aperture orientation control feature is provided in a liposuction instrument of the present invention having cauterizing electrodes embedded about the aspiration aperture(s) of a plastic outer cannula, an electrical communication mechanism can be embodied within the outer cannula the proximal portion thereof and its base portion so that electrical connectivity can be achieved between the cauterizing electrode on the outer cannula and its electrically conductive contact pad embedded within the base portion of the outer cannula.

As shown in FIGS. 15 through 19, the liposuction device of the present invention may be equipped with a monopolar-type electrocauterizing cannula assembly, in contrast with the bipolar designs shown and described in detail hereinabove. While the monopolar-type liposuction instrument of the present invention is shown embodied within the general design of FIGS. 1A through 1C, with appropriate modifications, it is understood that any of the alternative embodiments shown and described hereinabove can be readily modified to provide a monopolar-type electrocauterizing cannula assembly in accordance with the principles of the present invention As illustrated in greater detail in FIGS. 15 and 16, the liposuction device 301 comprises an hand-holdable housing 302, a detachable cannula 303 with a monopolar electro-cauterizing electrode(s), and a reciprocation mechanism 304 for causing the cannula 303 to reciprocate relative to the housing. Cannula 303 of the present invention comprises an elongated tube 390 having an aspiration (i.e. suction) aperture 306 at its distal end and a base 307 operably associated with the proximal end of the tube 390. Preferably, cannula base 307 has an outlet port 308 formed at its remote end, and a notch or recess like structure 309 formed in its central most portion, as shown. As will be described in greater detail hereinafter, notch structure 309 functions to releasably receive a terminal portion of the electrically-conductive actuator element 312, in order to engage therewith and thereby actuate reciprocation of cannula 303 within housing 302 during operation of the reciprocation mechanism 304. In alternative embodiments of the present invention, the notch like structure 309 can be realized in variety of different ways depending, of course, on the structure of the actuator 312.

Figure 16:
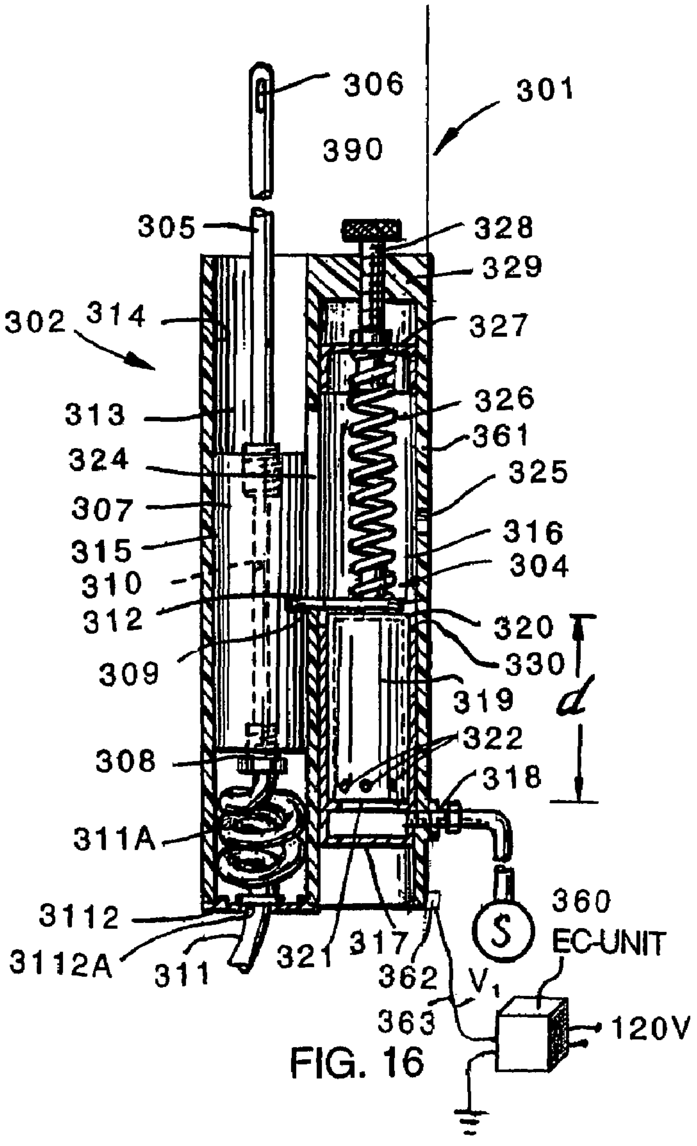
FIG. 16 is a cross-sectional view of the liposuction device of the present invention taken along line 16-16 of FIG. 15.
Figures 18, 18A, 18B:
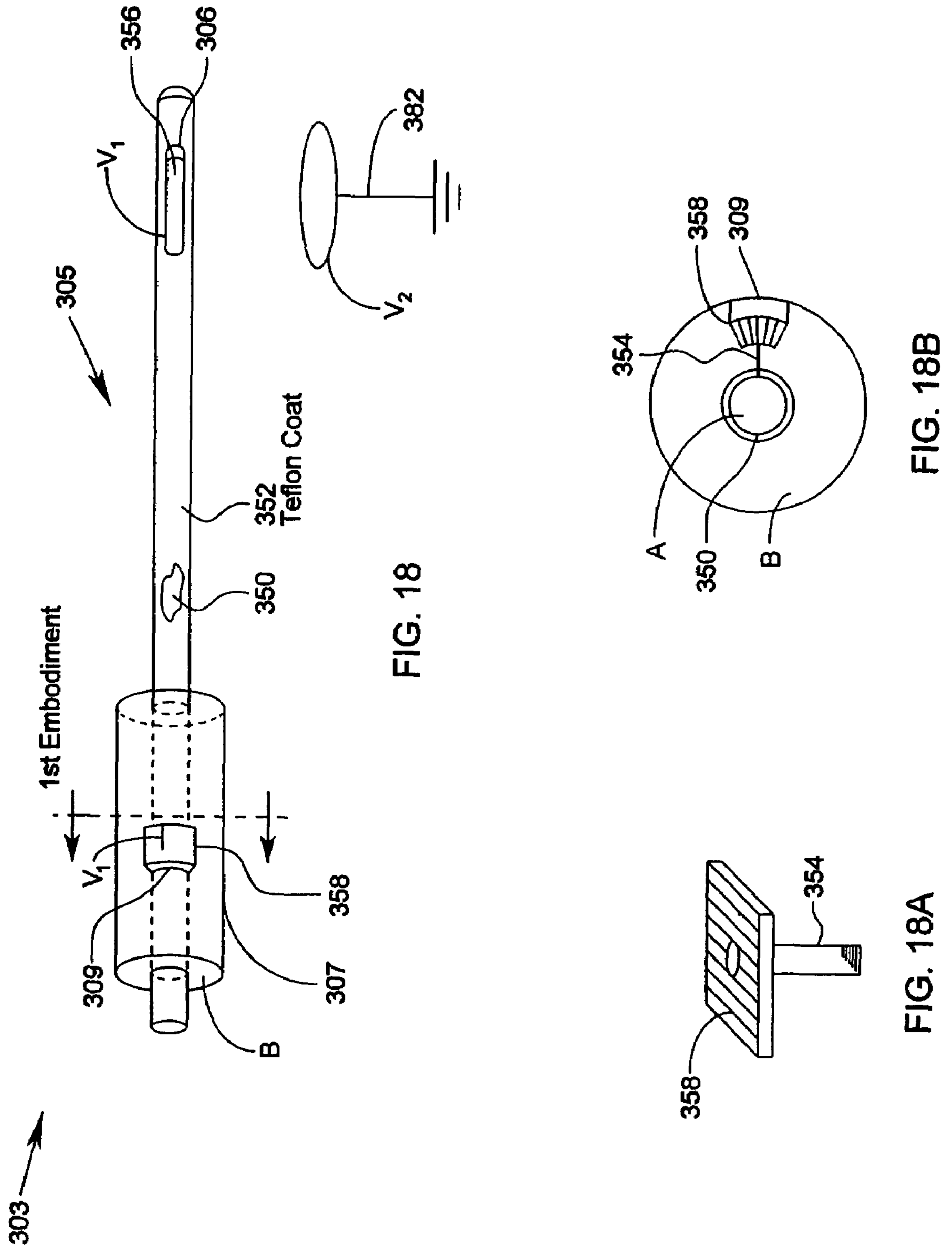
FIG. 18 is a perspective view of a first illustrative embodiment of the monopolar electro-cauterizing cannula assembly of the present invention shown removed from the hand-supportable device of FIG. 15, wherein an electrically-insulative outer coating is applied over an electrically conductive cannula structure that is electrically connected to the active lead of a unipolar electro-cautery power supply unit when the cannula assembly is installed within the hand-supportable device and the device is electrically connected to the power supply unit by way of any electrical cable.
FIG. 18A is a perspective view of the electrically-conductive contact element installed in the notch structure of the cannula assembly, for establishing electrical contact between the cannula assembly and the power source in the hand-held housing.
FIG. 18B is a cross-sectional view of the base portion of the cannula assembly shown in FIG. 18, taken along line 18B-18B drawn therein.
Figure 19:
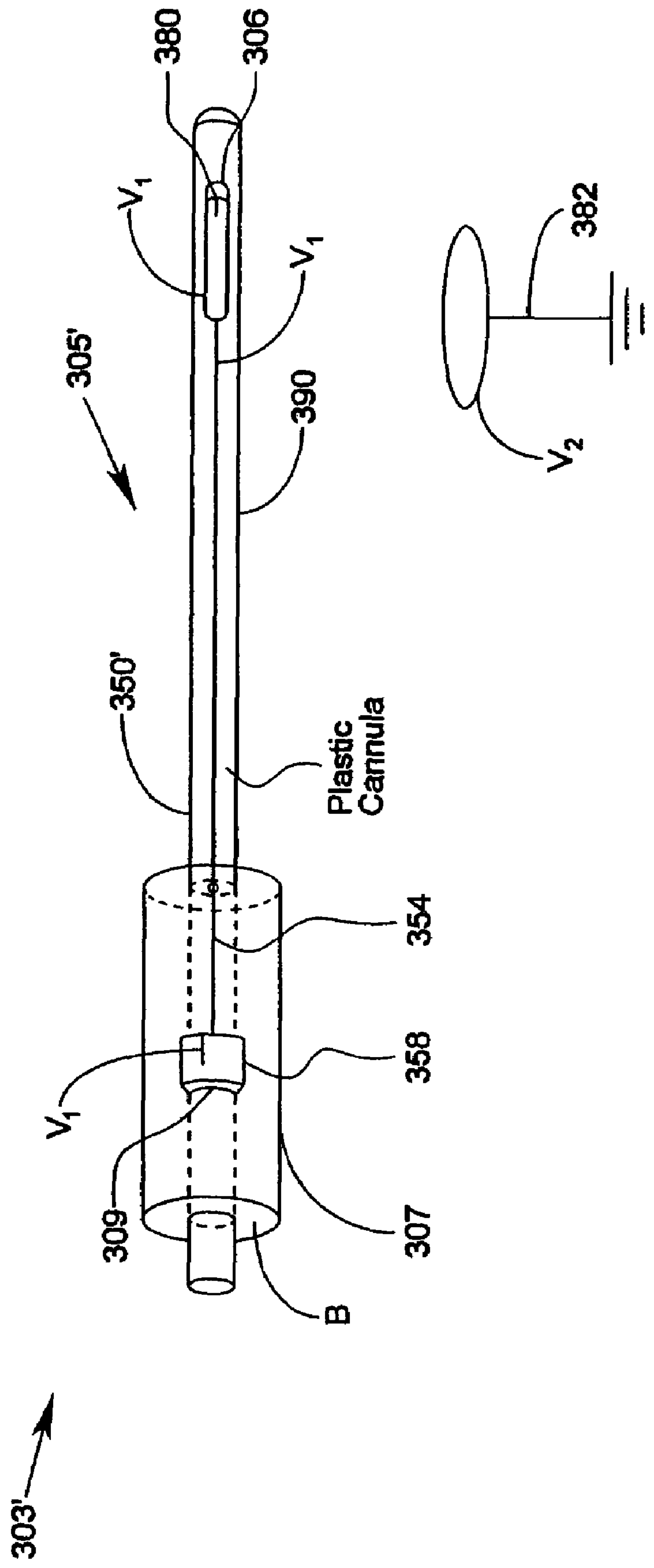
FIG. 19 is a perspective view of a second illustrative embodiment of the monopolar electro-cauterizing cannula assembly of the present invention shown removed from the hand-supportable device of FIG. 15, wherein an electrically-conductive cauterizing electrode, in the form of an eyelet-like structure, is mounted about the perimeter of the aspiration (i.e. suction) aperture in the cannula assembly, and electrically connected to the active lead of a unipolar electro-cautery power supply unit when the cannula assembly is installed within the hand-supportable device and the device is electrically connected to the power supply unit by way of any electrical cable.

As shown in FIGS. 16, 18 and 19, the shape of cannula base 307 is preferably cylindrical and will match the bearing surfaces which guide the cannula as it is caused to reciprocate within housing 302. As illustrated, cannula 303 (303') has a continuous passageway 310 which extends from aspiration aperture 306 to outlet port 308 for transporting aspirated fat tissue through aperture 306 to a conventional vacuum source (not shown). To achieve this function, the vacuum source is connected to outlet port 308 using preferably optically transparent, semi-flexible tubing 311.

As shown, the gross geometry of the housing 302 is preferably that of an ellipsoid, however, other geometries such as, for example, as a cylindrical structure, can be used in practicing the present invention. Housing 302 has a cannula cavity generally indicated by reference numeral 313, and has generally cylindrical bearing surfaces 314 which match the outer bearing surface 315 of cannula 303, to permit sliding movement of cannula 303 within 313. While cylindrical bearing surfaces have been selected in the preferred embodiment, the use of other forms of bearing surfaces (e.g., rectangular or triangular) is contemplated. To minimize friction, bearing surfaces 314 and 315 may be coated with a Teflon$^R$ or functionally equivalent coating, to facilitate easy sliding of cannula base 307 within cavity 313 with low wear.

Figure 17:
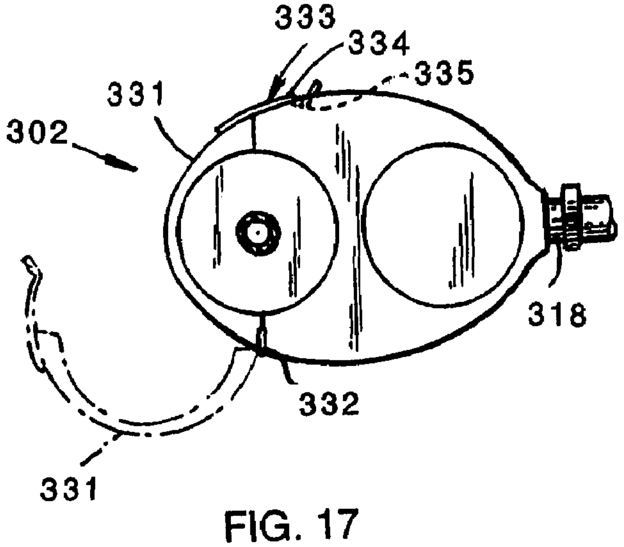
FIG. 17 is an elevated end view of the liposuction device of the present invention illustrated in FIG. 15, showing the monopolar electro-cauterizing cannula assembly thereof retained within the cannula cavity of its hand-holdable housing, and with the hingedly connected housing cover panel disposed in an open position for removal of the cannula assembly therefrom.

As illustrated in FIG. 17, housing 302 of the illustrative embodiment is provided with a hinged cover 331. Hinged cover 331 allows cannula cavity 313 to be opened and accessed and cannula 303 to be selectively installed in and removed from housing cavity 313. Cover panel 331 has a semi-circular cross-sectional geometry and is connected to the remainder portion of the housing 302 by a conventional hinge means 332. To secure cover panel 331 to the remainder of housing 302, a releasable locking means 333 is provided at the interface of hinge cover 331 and the remainder portion of housing 302, as shown. Releasable locking means 333 can be realized in a variety of ways, including, for example, using a spring biased clamp element 334 which engages in a notch 335 formed in the external surface of the remainder portion of the housing 302, as illustrated in FIG. 17.

In the case of the cannula assembly design of the first illustrative embodiment shown in FIG. 18, the distal and proximal portions of the cannula 303 are made from an electrically conductive lumen material 350 having a non-conductive coating 352 (e.g. made from TFE coating or outer plastic sheath) applied thereover. Preferably, the non-conductive coating 352 disposed upon or applied over the electrically-conductive cannula 303 forms a cauterizing electrode 356 about on the inner edge walls of the aspiration aperture 306, as shown in FIG. 18.

The function of the aspiration aperture 306 is to ensure that aspirated fatty tissue is subject to an electrical potential difference (i.e. V1−V2) maintained between the cauterizing electrode and reference ground, which is sufficient to electro-cauterize fatty tissue as the same is being aspirated through the aspiration aperture. In this illustrative embodiment, the electro-cauterizing electrode 356 formed about the outer edge of the aspiration aperture 306 is maintained at electrical potential V1 by way of a first electrically conductive pathway realized along the cannula assembly, best illustrated in FIGS. 18, 18A and 18B. As shown in these drawings, electrical contact plate 358 can be embedded within the notch 309 formed in the base portion 307 of the cannula assembly, while an electrically conductive post 354 affixed to contact plate 358 establishes electrical contact with the distal portion of the electrically conductive lumen 350. By virtue of the fact that the electro-cauterizing electrode 356 is realized from the conductive material of the electrically conductive lumen 350, which is in electrical contact with the electrical contact plate 358 via electrically-conductive post 354.

In the case of the cannula assembly design of FIG. 19, the cannula 303' is made from an electrically non-conductive material (e.g. plastic) having an electro-cauterizing electrode 380 (realized in the form of any eyelet or like structure) mounted about each cannula aspiration aperture 306 provided at the distal end of the cannula. As will be described in greater detail below, preferably the electrode

380 is formed on the inner edge wall of the aspiration aperture and is maintained at electrical potential V1 whereas the human patient is maintained at electrical ground potential V2=0 Volts, so that, during liposuction procedures, aspirated fatty tissue is subject to a potential difference (i.e. V1−V2), sufficient to electro-cauterize the fatty tissue as it is being aspirated through the aspiration aperture 306. As shown in FIG. 19, the same or modified electrical contact plate 358 of FIG. 18A can be embedded within the notch 309 formed in the base portion 307 of the cannula assembly 305'. As shown, the base portion of the electrically conductive post 354 is maintained in electrical contact with the electro-cauterizing electrode 380 by an electrical wire 354, embedded within the outer surface of the electrically non-conductive lumen 350', and electrically connected thereto so as to maintain these structures at the same electrical potential.

As shown in FIG. 16 when either cannula assembly 305 or 305' is properly loaded within the hand-supportable housing 302 of the liposuction instrument of the present invention, the electrically-conductive actuator 312 engages with the electrical contact plate 358 in notch 309 of the cannula base portion. In order to maintain the electro-cauterizing electrode(s) provided along the distal portion of the cannula assembly (305 or 305'), electrical contact plate 358, to which the electro-cauterizing electrodes are connected, must be electrically connected to the output lead of a unipolar cautery unit 360 which generates a radio-frequency (RF) power signal maintained at voltage potential V1, referenced to electrical ground, V2, which is zero volts. This electrical connection between the cautery unit 360 and embedded electrical contact 358 in the base portion of the cannula assembly (305 or 305') can be established using internal wiring 361 which extends from electrically-conductive spring support plate 327 and power jack 362 mounted within the wall of the housing. Such internal electrical wiring can be embedded within the walls of hand-supportable housing 302 or otherwise routed within the same. Notably, the actuator 312, spring 326 and spring support plate 327 are each made from an electrically conductive material so as to each be maintained at substantially the same electrical potential.

As shown in FIG. 16, a flexible shielded-type power cable 363 is used to electrically connect the power jack 362 on the liposuction instrument to the output power lead of the electro-cautery power supply unit 360. By way of this arrangement, the electro-cauterizing electrode 356 in the cannula assembly (305 or 305') is maintained at a relatively high electrical voltage V1, while the tissue of the patient to be aspirated is maintained at a substantially lower voltage V2 by virtue of indifferent/defuse electrodes attached to the patient during a liposuction procedure conducted in accordance with the principles of the present invention.

In alternative embodiments of the present invention, the hand-supportable housing may not be provided with a hingedly connected cover panel, as shown in FIG. 17, but rather the base portion of the cannula can be adapted to slide into the cannula cavity 313 and snap-fit into the actuator 312 which may be realized using a spring-loaded ball or like structure, as taught in Applicant's U.S. Pat. No. 5,112,302, incorporated herein by reference in its entirety. In other embodiments, the base portion of the cannula assembly and the actuator associated with the reciprocation mechanism may be realized in virtually any manner than enables slidable movement of the cannula relative to the hand-supportable housing, and supply of the electrical voltage V1 to the electro-cauterizing electrode associated with the cannula, regardless of whether the electro-cauterizing electrode is realized using the methods illustrated in FIGS. 16, 18 and 19, or by any other means.

In general, a gas, air or electrically driven motor(s) can be used to realize the reciprocation mechanism 304 of present invention and thus effectuate reciprocation of cannula 303 within cannula cavity 313. In the embodiments illustrated in FIGS. 15 through 19, a gas driven piston-type motor is employed, although it is understood, that other type of motor, including rotary and linear motors alike, can be used to the realize reciprocation mechanism 304 of the liposuction instrument of the present invention.

As illustrated in FIG. 16, a piston-type motor 304 is mounted within a motor cavity 316 provided adjacent cannula cavity 313 of housing 302. In general, motor 304 comprises a chamber housing 317 having a gas inlet port 318 and an inner chamber generally indicated by reference numeral 319. Slidably received within the inner chamber of housing 317 is a movable piston 320 having formed in its lowermost wall 321, one or more gas outlet ports 322. Mounted to the top portion of movable piston 320 is actuation element 323, which projects through a longitudinally disposed slot 324 formed in the bearing wall 314 of cannula cavity 313. Projection 312 of actuation element 323 through the slot 324, is received within notch 309 formed in cannula base 307 and operably associates cannula 303 with motor 304.

As illustrated in FIG. 16, chamber housing 317 is fixedly disposed within motor cavity 316. Motor cavity 316 is also provided with at least one port 325 for ventilating to the ambient environment, gas released from movable piston 320 upon reaching it maximum displacement or excursion. Movable piston 320 is biased in the direction of chamber housing 317 by way of a spring biasing element 326. The compliance of spring biasing element 326 can be adjusted by moving the position of slidable wall 327 by rotating, for example, threaded element 328 passing through a portion 329 of the housing 302, as shown. With this arrangement, adjustment of wall 327, closer to or farther from chamber housing 317, results in decreasing or increasing, respectively, the compliance of spring biasing means 326. This, in turn, provides a simple, yet reliable way in which to control the rate of reciprocation of movable piston 320, and thus the rate of reciprocation of cannula 303 relative to housing 302.

The manner of operation of piston-type motor 304 is described as follow. Gas, such as pressurized air of $N_2$ gas, is introduced under constant pressure to inlet port 318 of chamber housing 317. As the gas fills up the volume enclosed by the interior walls of the movable piston and the chamber, inner chamber 319 begins to expand, forcing movable piston 320 upwardly against the biasing force of spring biasing element 326. When movable piston 320 is displaced sufficiently enough from chamber housing 317 so that gas within expanding chamber 319 can be released through gas exit port 325 to the ambient atmosphere, and piston 320 will be forced back downwardly into chamber housing 317 at a rate inversely proportional to the compliance of spring biasing element 326. Subsequently, chamber 319 will again fill up with gas, piston 320 will again be displaced and gas subsequently vented, whereupon reciprocating displacement of piston 320 will be repeated again in a cyclical manner. Since movable piston 320 is operably connected with cannula base 307 by way of actuation element 323, this reciprocating movement of piston 320 results in reciprocating movement of cannula 303 within cannula cavity 313.

As illustrated in FIG. 16, the amount of excursion that the piston is permitted to undergo before gas venting and subsequent downward piston movement occurs, is determined by the distance "d" defined gas output port 322 and top wall surface 330 of chamber housing 317. Typically, a cannula excursion distance of three inches, for example, will necessitate that the parameter d, defined above, also be about three inches.

To use the liposuction device 301 of the illustrative embodiment described above with either cannula assembly 305 or 305', the surgeon inserts either the cannula assembly shown in FIG. 18 or 19 into the cannula cavity of the hand-supportable housing 302 so that the actuator 312, or other embodiment thereof, engages within the notch 309 or like structure within the base portion of the cannula assembly, and secures the cannula assembly within the hand-supportable housing, as shown, for example in FIG. 16. An indifferent/defuse electrode 382 is applied to the skin of the patient in a conventional manner, and the indifferent/diffuse electrode is then connected to the V2 terminal of the electro-cautery power supply unit 360. The surgeon then activates the air power supply to the instrument, as well as the electro-cautery power supply unit 360. Then, while holding the housing within the grasp of the surgeon's hand, the surgeon performs a liposuction procedure in a normal manner. During the procedure, the instrument effectuates periodic displacement of the general location of aspiration along the distal end of the cannula assembly, through the reciprocating movement of cannula while permitting electro-cauterization of aspirated tissue during operation of the liposuction device.

When performing a liposuction procedure using the cannula assembly shown in FIG. 18, the tissue of the patient to be aspirated through the aspiration aperture 356 is maintained at electrical ground potential by way the indifferent/diffuse electrode 382. At the same time, the electro-cauterizing electrode 356 is maintained in electrical contact with the active output terminal of the unipolar cautery power unit 360 by virtue of the electrical pathway established therebetween and described in detail above. It is understood, however, that there are a variety of different electrical paths that may be established to maintain the electro-cauterizing electrode(s) 356 in electrical contact with the output power terminal of the unipolar cautery power unit 360. Thus, during a liposuction procedure, the sample of tissue about to be aspirated through the aspiration aperture is maintained at a difference in electrical potential (i.e. at a voltage) equal to the electrical potential of the active output power terminal $V_2$, referenced to zero volts ground potential $V_1$. In practice, this voltage is sufficient to electro-cauterize tissue during aspiration to prevent hemorrhaging and the like to the patient, thereby improving the safety of the procedure.

The above-described mono-polar electro-cauterizing liposuction instrument can be modified in many ways. For example, the form factor of the hand-supportable housing may be realized in the form of the other hand-supportable housing shown herein. Also, the means and way by which the electro-cauterizing cannula assembly physically and electrically connects to the actuator and thus the reciprocation mechanism within the hand-supportable housing may vary from embodiment to embodiment of the present invention.

In the illustrative embodiments of the present invention described above, the powered liposuction instrument employed either a pneumatically-powered or an electrically powered reciprocation mechanism to drive the actuator engaging the inner cannula structure of the instrument. In case of the illustrative embodiments of the pneumatically-powered liposuction instruments described above, control over pressurized air flow streams, used to drive the motion of the actuator during instrument operation, is carried out onboard of the hand-supportable liposuction instrument. In alternative embodiments like the ones shown in FIGS. 20A through 38B, and described in detail hereinafter, control over pressurized air-flow streams used to drive the liposuction instrument is carried out external to the hand-supportable instrument, preferably within an external instrument control unit (i.e. instrument controller) having a control console that support various instrument control and display functions.

Figure 20A:
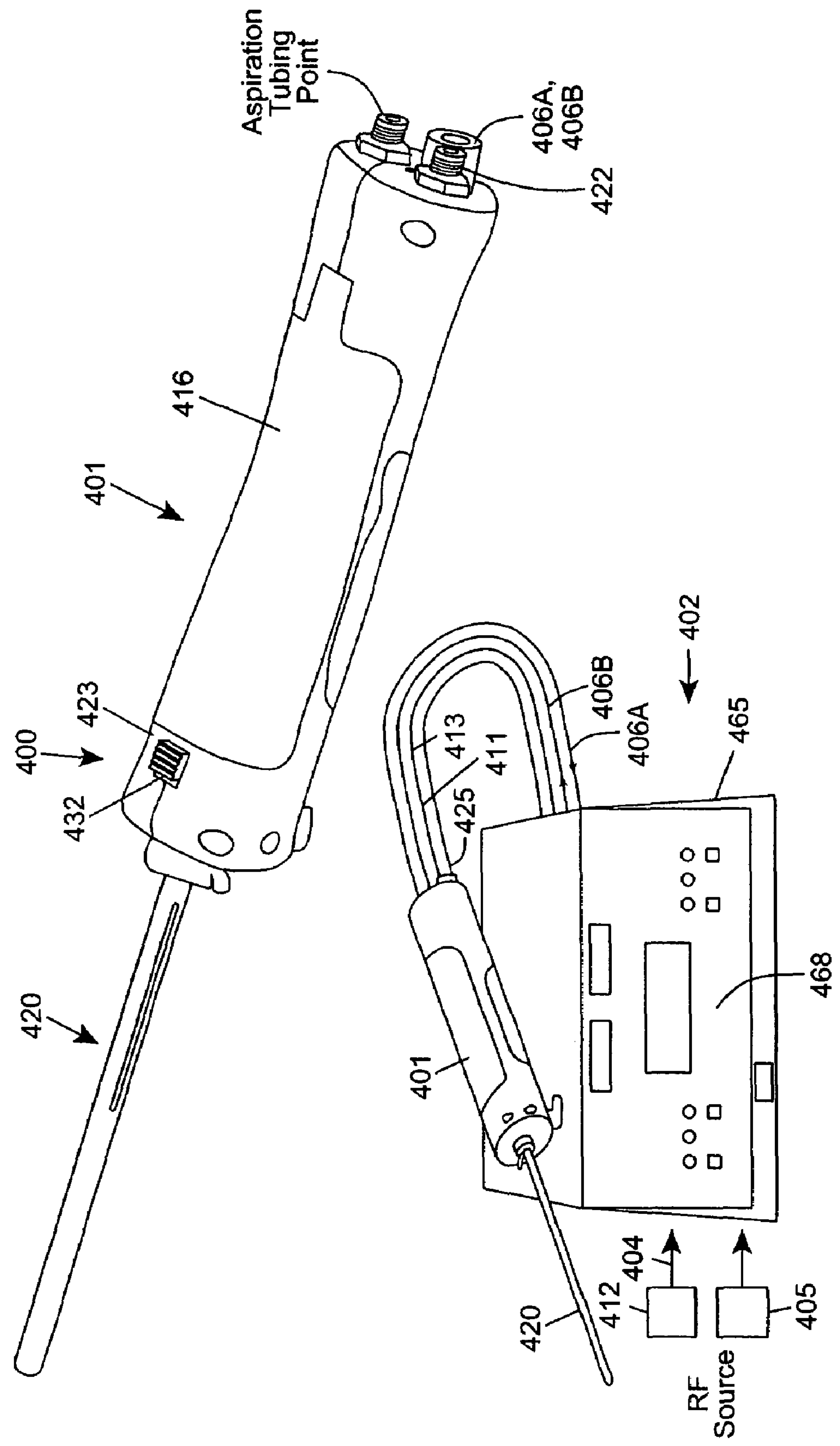
FIG. 20A is a perspective view of another alternative illustrative embodiment of the air-powered liposuction instrument system of the present invention, wherein the automatic reciprocation of the inner and outer cannulas of the powered liposuction instrument is achieved by electronically controlling the flow of pressurized air streams within a dual-port pressurized air cylinder supported within the hand-supportable housing of the instrument, using digital electronic control signals generated within an instrument controller.

Air-Powered Liposuction Instrument System Having an Intelligent Instrument Controller with an Electronically-Controlled Air-Flow Control Valve Assembly and RF Power Signal Input/Output Port Referring to FIGS. 20A through 34, another illustrative embodiment of a pneumatically-powered (i.e., air-powered) liposuction instrument system of the present invention 400 will be described in detail. As shown in FIG. 20A, the air-powered liposuction system comprises: a pneumatically-powered liposuction instrument 401; an intelligent instrument controller 402 provided with an electronically-controlled air-flow control valve assembly 403 and an RF power signal input/output port 404; an external pressurized air supply source (i.e. generator) 405 for supplying a pressurized air flow stream to the electronically-controlled air-flow control valve assembly 403, and from which a pair of pressurized electronically-controlled air flow streams 406A and 406B are generated within the instrument controller 402 and supplied to a dual-port air cylinder (i.e. reciprocation mechanism) 407 within the hand-supportable liposuction instrument 401 by way of a dual air-flow tubing structure 408 (connected between the instrument and the controller) so as to drive the actuator 409 within the instrument and thus reciprocate the inner cannula structure 410 employed therein during power-assisted liposuction operations; an electrical wiring cable 411 connected between the instrument 401 and the instrument controller 402, to support the communication of low-voltage electrical control and monitoring signals between the instrument 401 and the controller 402; and a RF power signal source (i.e. generator) 412, connected to the RF power input signal port 404 on the instrument controller by way of a short length of RF power signal cable 413, for generating and supplying a RF power signal (of suitable frequency and power characteristics) to the instrument controller 402 for electronically-controlled delivery of the generated RF power signal, from RF output port 422, to the hand-supportable liposuction instrument 401 by way of a longer-length flexible RF power signal cable structure 413 connected between the RF power output port 404 on the instrument controller 402 and the RF power signal input port 404 on the hand-supportable liposuction instrument 401. During operation of this powered liposuction instrument system, the inner and outer cannulas of the powered liposuction instrument are automatically reciprocated in response to a pair of electronically controlled pressurized air flow streams generated within the instrument controller and supplied to the opposite ends of the dual-port pressurized air cylinder 407 within the instrument, to thereby cause the actuator and this inner cannula within the instrument to reciprocate at a stroke length and rate manually selected by the surgeon manipulating reciprocation stroke length and rate control switches 415 and 416 mounted on the instrument housing.

Figure 27A:
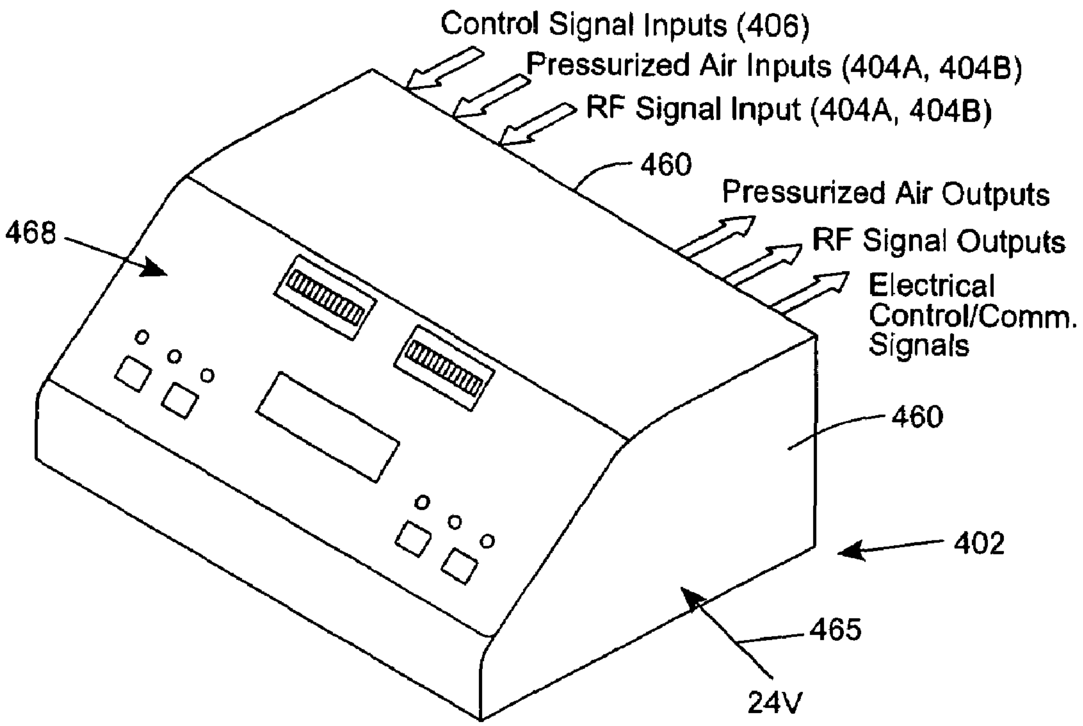
FIG. 27A is a perspective view of the intelligent instrument controller (i.e. control unit) of the present invention used in conjunction with the air-powered liposuction instruments illustrated in FIGS. 20A, 35A, and 40A, wherein the instrument controller is shown comprising a number of components, namely: (1) a user control console having (i) four membrane type switches for selecting a desired cannula stroke length dimension (i.e. inches or centimeters) for measurement and display and for enabling and disabling electro-cautery function selection, (ii) six LED indicators for indicating power ON/OFF function selection, cannula stroke length dimension selection, and electro-cautery enable/disable function selection, (iii) a pair of LCD-based display panels for displaying (bar graph indications of inner cannula reciprocation rate (in cycles/sec) and inner cannula stroke position measured by the cannula position sensor mounted within the hand-supportable liposuction instrument, and (iv) a LCD-based panel for displaying measured numerical values for the instantaneous rate of reciprocation for the inner cannula and the instantaneous stroke length thereof, and (2) a compact housing mounting the multi-core connector assembly of the present invention, as well as an input port for receiving RF power signals generated from an external RF signal source and an input port for receiving a source of pressurized air to drive the air-powered liposuction instrument of the present invention.
Figure 27B:
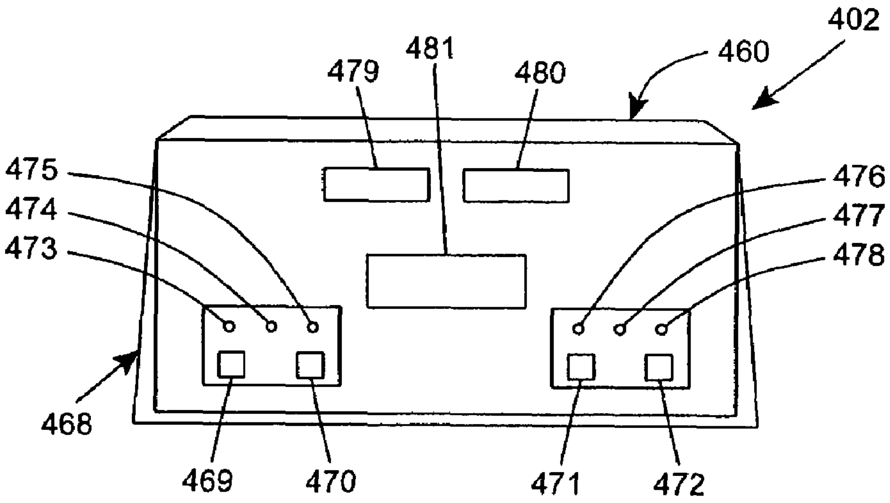
FIG. 27B is a graphical representation of the user control console portion of the intelligent instrument controller shown in FIG. 27A.
Figure 27C:
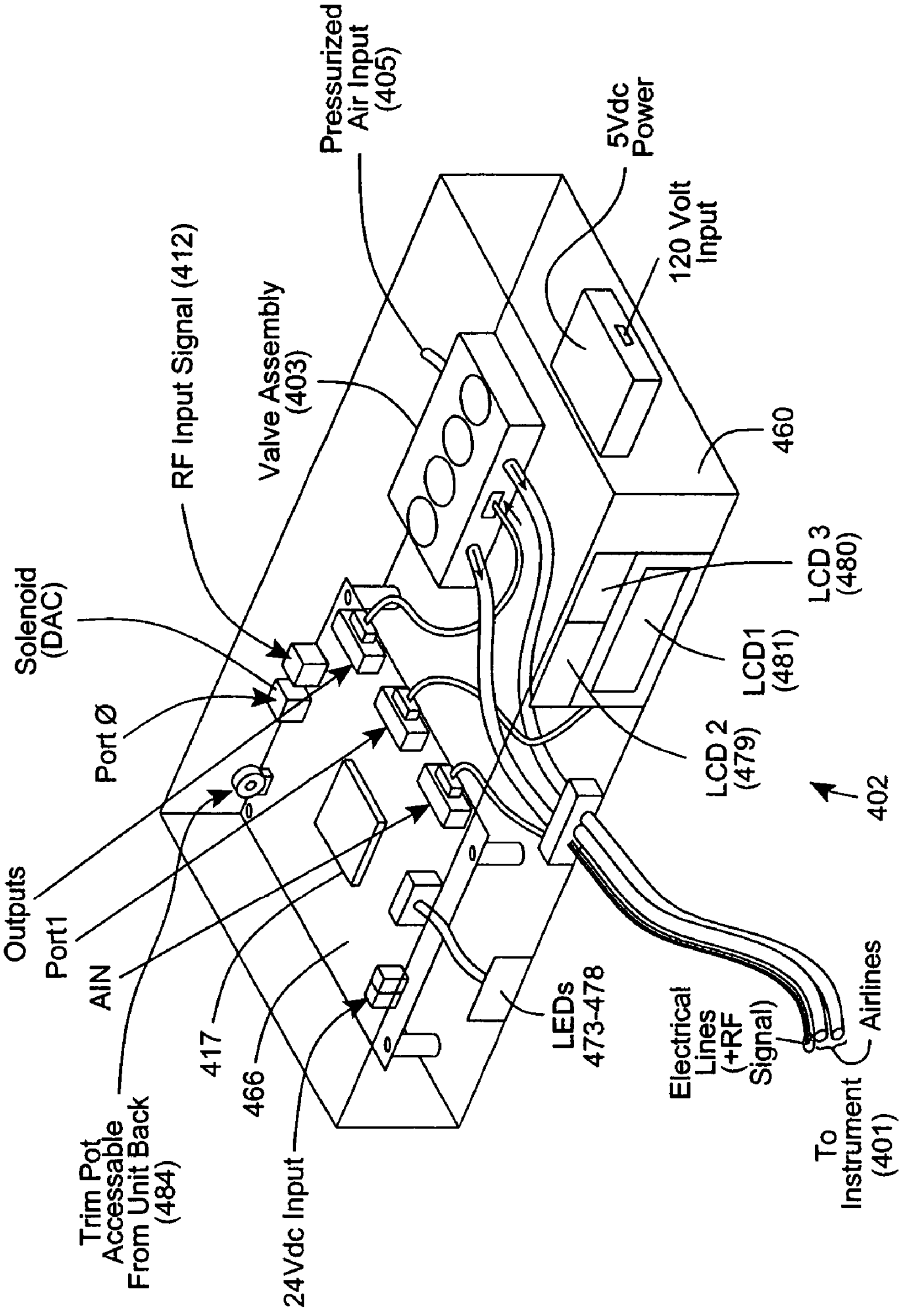
FIG. 27C a schematic representation of an exemplary layout of the components comprising the instrument controller of FIGS. 27A and 27B, and showing the various electrical and mechanical ports supported therewithin.
Figure 30:
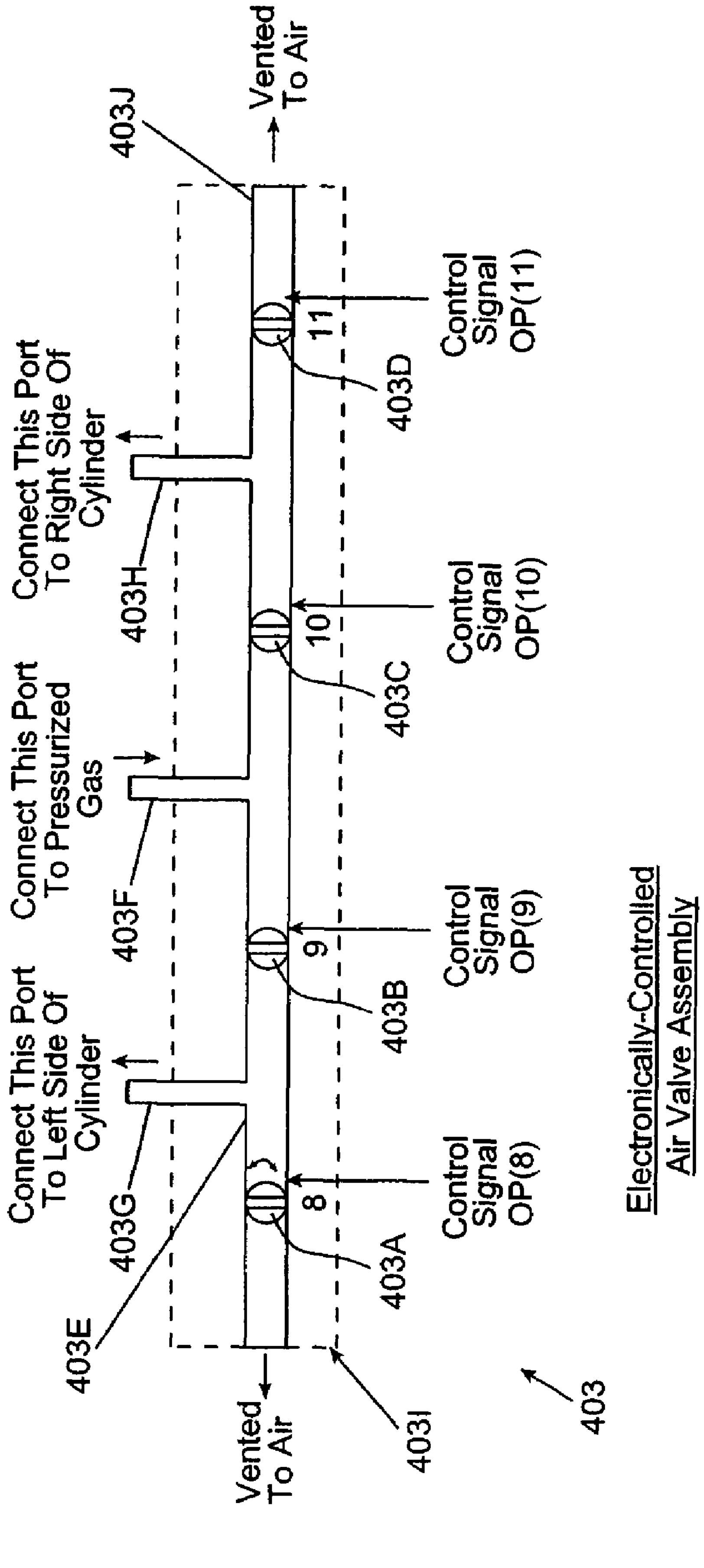
FIG. 30 is a schematic representation of the digitally-controlled multi-port air-flow control valve assembly employed in the instrument controller of FIGS. 27A and 27B, illustrating its central air-flow control port being connected to the external source of pressurized air, its left air-flow control port being connected to the left side of the air-driven cylinder within the liposuction instrument via the multi-core cable structure of the present invention, and its right air-flow control port being connected to the right side of the air-driven cylinder within the liposuction instrument via the multi-core cable structure of the present invention, whereas digital output control voltage signals OP(8) through OP(1) are provided to the electrically-controlled valve solenoids, as shown, to electronically control the operation of the air-pressure driven inner cannula reciprocation mechanism employed within the powered liposuction instruments shown in FIGS. 27A through 28H.

As shown in FIGS. 27C and 30, the pair of electronically controlled pressurized air flow streams 406A and 406B are used to power the reciprocation mechanism within the liposuction instrument. These pressurized air-flow streams are produced within the instrument controller 402 by (i) automatically generating digital control signals OP(8) through OP(11) from a programmed microprocessor 417 aboard the instrument controller 402 running the control programs illustrated in FIGS. 31A through 33C, and (ii) supplying these digital control signals OP(8) through OP(11) to the electronically-controlled air flow valve assembly 403 shown in FIG. 30, mounted aboard the instrument controller. Also, bipolar RF power signals 418 are (i) generated from external RF power signal generator 412, (ii) controllably switched through the intelligent instrument controller 402, and (iii) ultimately supplied to the bipolar terminals of the electro-cauterizing dual cannula assembly of the instrument system 420. During instrument operation, these bipolar RF power signals are produced aboard the instrument controller by (i) generating digital control signal DAC(0) and (ii) supplying this digital control signal to a solenoid relay 421 aboard the instrument controller. When the solenoid relay 421 is switched, it commutes the RF power signal supplied to RF power signal input port 404 to the RF power signal output port 421, and is thus supplied to the electro-cautery cannula assembly by way of flexible RF power signal cable construction 413, as shown in FIG. 20A.

Figure 20B:
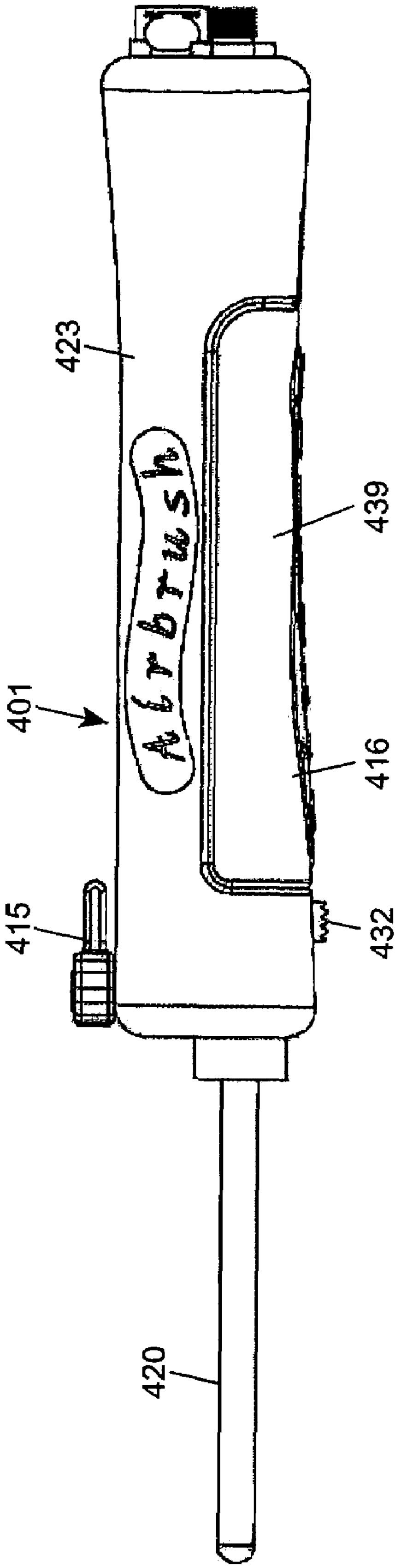
FIG. 20B is an elevated side view of the powered liposuction instrument shown in FIG. 20A.
Figure 20C:
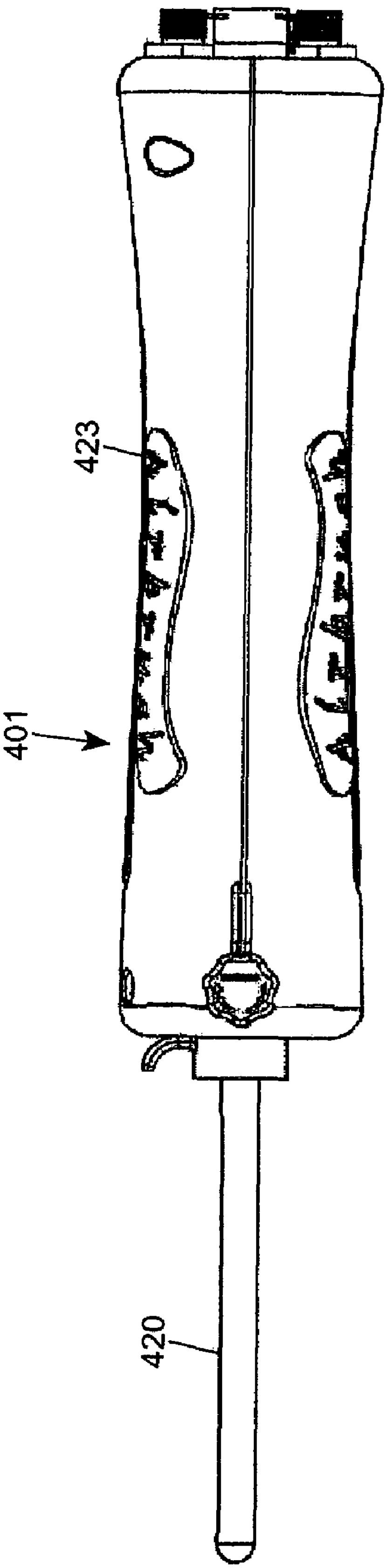
FIG. 20C is a top view of the powered liposuction instrument shown in FIG. 20A.
Figure 20E:
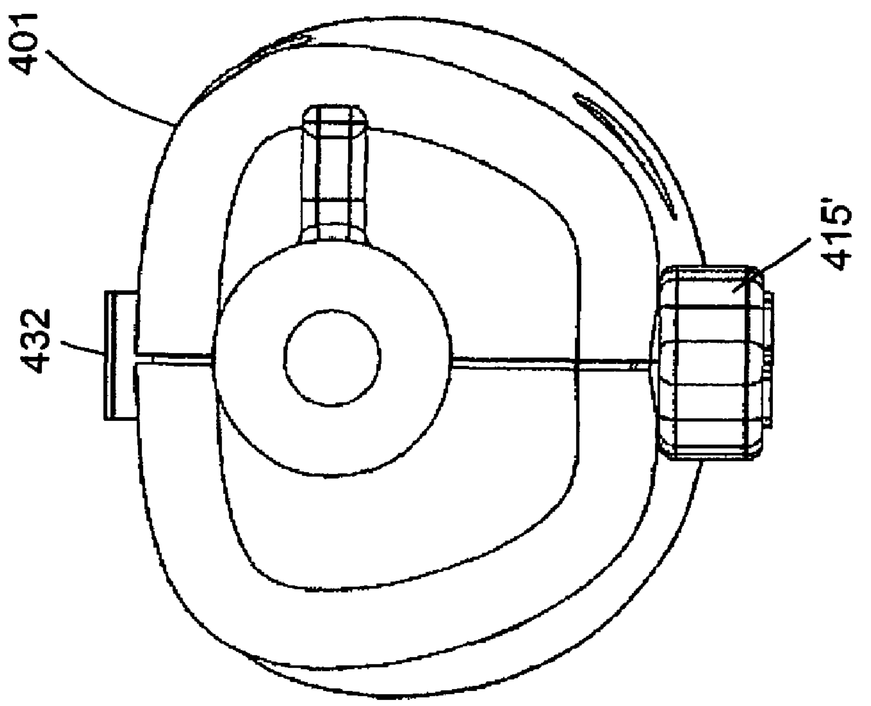
FIG. 20E is an elevated view of the front end of the air-powered liposuction instrument of FIG. 20A, showing the electro-cauterizing dual-cannula liposuction assembly of the illustrative embodiment releasably connected to the front portion of the air-powered liposuction instrument.
Figure 20D:
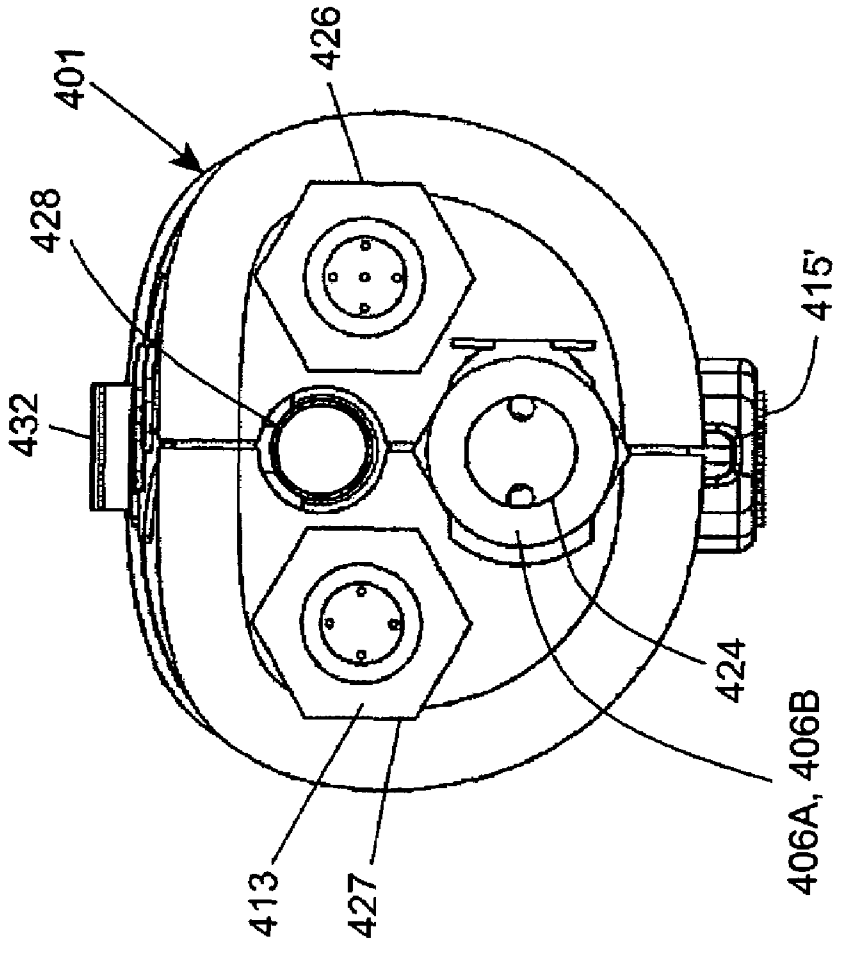
FIG. 20D is an elevated view of the rear end of the powered liposuction instrument of FIG. 20A, showing its pressurized air-power supply-line connector, its electrical control signal connector, and its RF power signal connector, and also its vacuum-pressurized aspiration tubing establishing a physically interface with the base portion of the inner cannula through the rear end portion of the air-powered liposuction instrument.

As shown in FIG. 20D, the rear end of the powered liposuction instrument housing 423 supports a number of connectors (ports), namely: a pressurized dual air-power supply-line connector 424, for connecting one end of the dual air-flow tubing structure 425 to the instrument, while the other end thereof is connected to a matching connector mounted on the rear panel of the instrument controller; an electrical control signal connector 426 for connecting one end of electrical control signal cable 411 to the instrument, while the other end thereof is connected to a matching connector mounted on the rear panel of the instrument controller; an RF power signal connector 427 for connecting one end of the flexible RF power signal cable 413 to the instrument, while the other end thereof is connected to a matching connector mounted on the rear panel of the instrument controller 402; and a tissue-aspirating tubing port 428, in communication with a cylindrical recess 429 extending along the central longitudinal axis of the instrument housing 423, for permitting the flexible aspiration tubing 430, connected to a barbed tube receiving structure 431 formed on the base portion of the inner cannula, to freely slide along the cylindrical recess during cannula reciprocation operations.

Figure 21A:
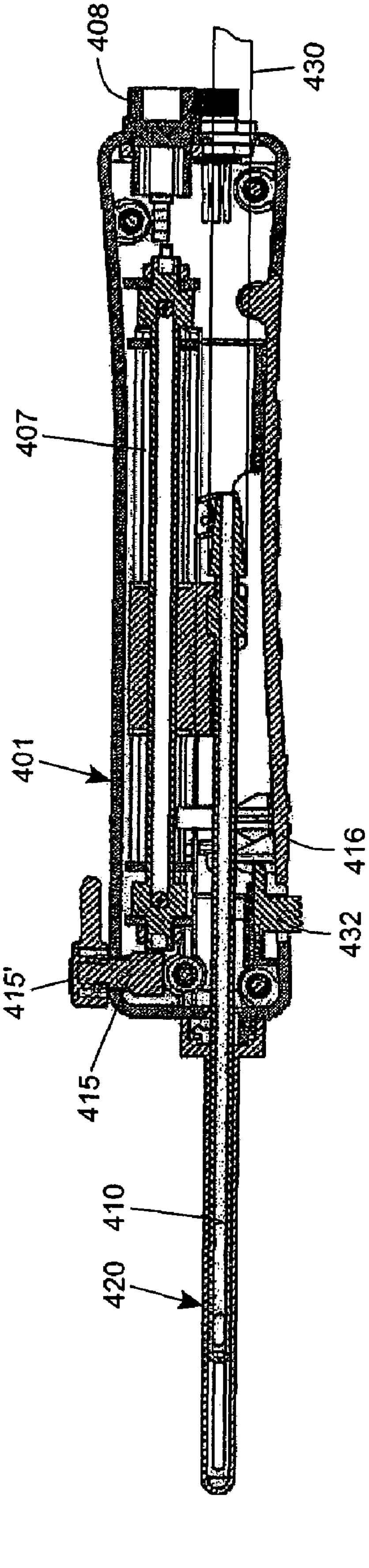
FIG. 21A is a cross-sectional view of the air-powered liposuction instrument of FIG. 20A, taken along line 21A-21A in FIG. 20C.
Figure 21B:
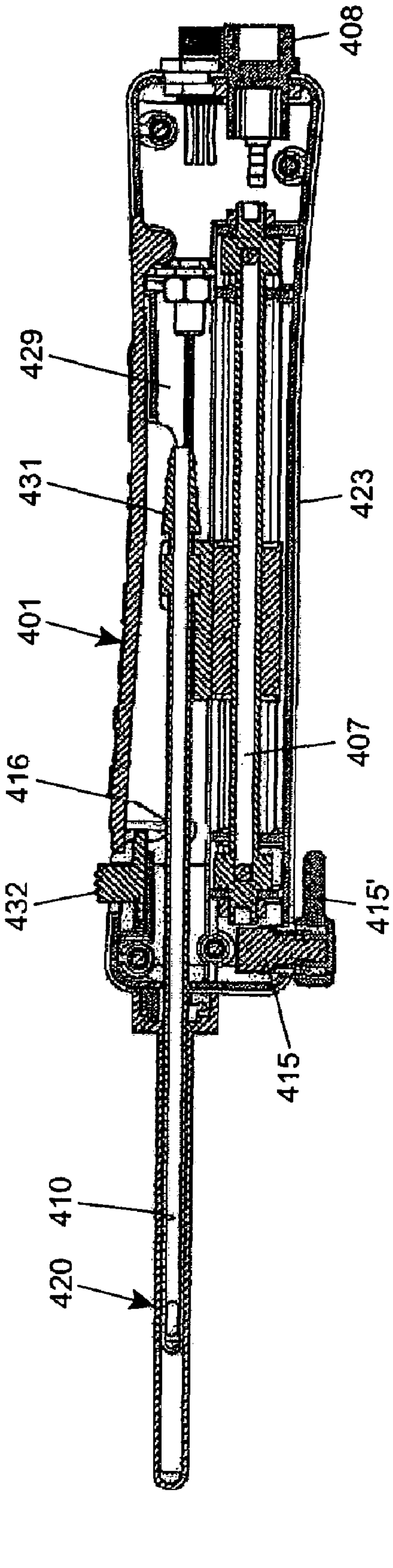
FIG. 21B is a cross-sectional view of the air-powered liposuction instrument of FIG. 20A, taken along line 21B-21B in FIG. 20C.
Figure 23A:
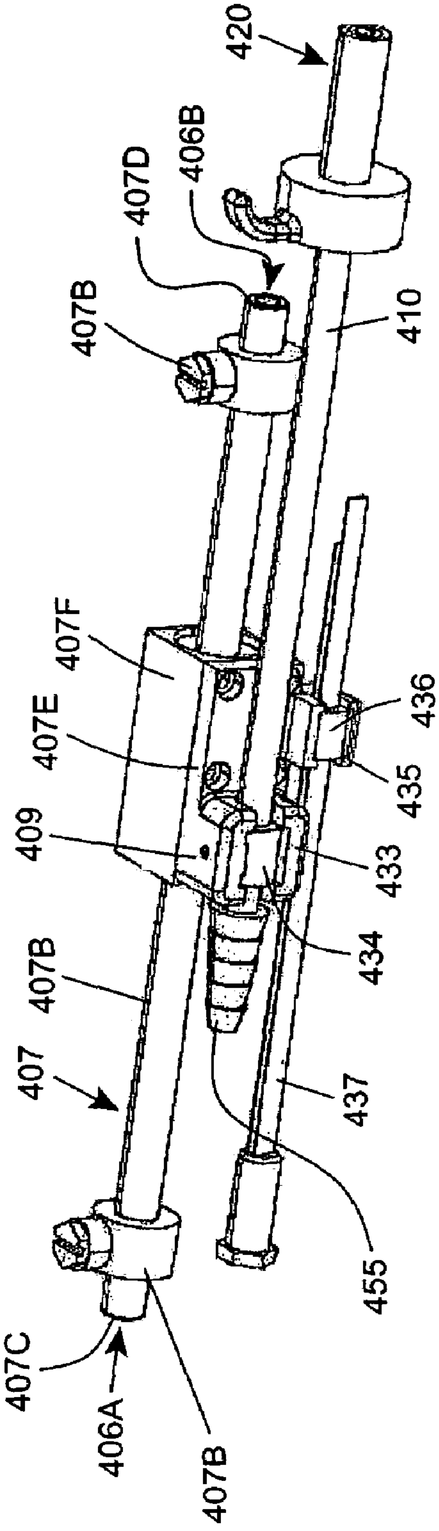
FIG. 23A is a perspective view of the dual-port air-cylinder driven inner cannula reciprocation subassembly arranged in association with its inner cannula actuator position sensing transducer, shown removed from the hand-supportable housing structure of the powered liposuction instrument of FIG. 20A, and with the base portion of the inner cannula locked within the carriage portion of the inner cannula actuator along with its actuator position sensing transducer.
Figure 23B:
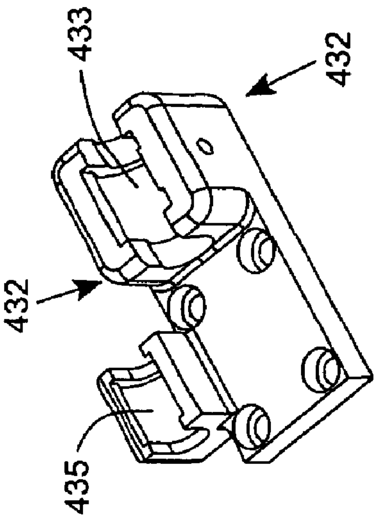
FIG. 23B is a perspective view of the inner cannula actuator employed in the inner cannula reciprocation subassembly shown in FIG. 23A.

FIGS. 21A and 21B show cross-sectional view of the hand-supportable liposuction instrument, and the various subcomponents contained therein comprising the same. Notably, the dual-port air-cylinder structure 407 used to realize the cannula reciprocation mechanism is operably coupled to the base portion of the inner cannula 410 by way of an actuator 409 having a carriage assembly 423. As shown in FIGS. 23A and 23B, actuator 409 is provided with a first recess 433 for receiving the base portion 434 of the inner cannula in a snap-fit manner, and also a second recess 435 for receiving the slidable electrode 436 associated with the actuator position sensing device 437 (i.e. slidable potentiometer) also in a snap-fit manner.

In this illustrative embodiment, the cannula reciprocation stroke length control switch (i.e. rotatable potentiometer) 415 is manipulated by a knob or like structure 415' located on the top surface of the instrument, whereas the cannula reciprocation rate control mechanism 416 is realized within the spring-biased hinged housing cover panel 439. These reciprocation mechanism controls will be described in greater detail hereinbelow.

Figure 21C:
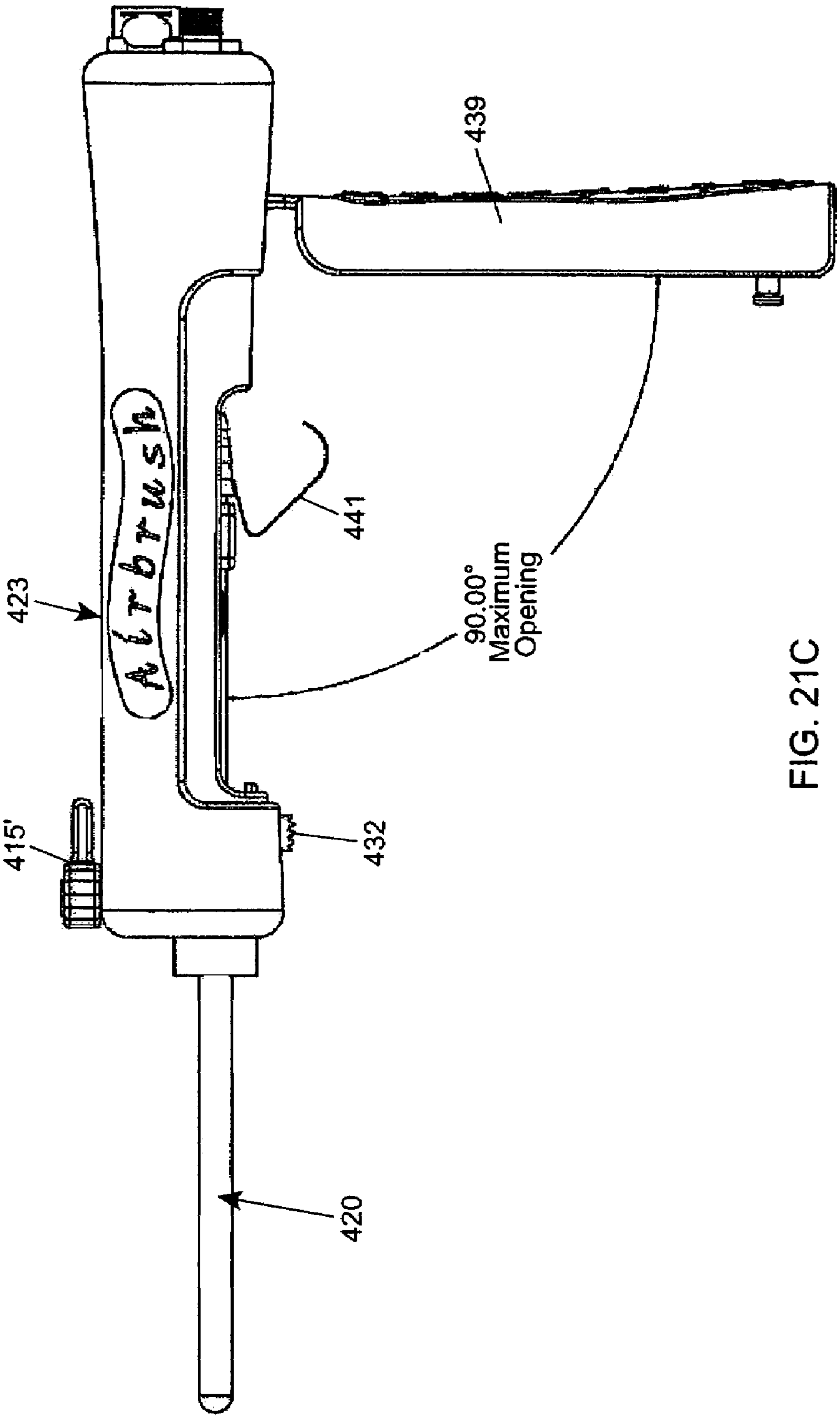
FIG. 21C is an elevated side view of the air-powered liposuction instrument of FIG. 20A, showing its hinged door panel arranged in its open configuration with its electro-cauterizing cannula assembly installed within the hand-supportable housing of the instrument, and its flexible aspiration tubing disconnected from the end of the inner cannula (and not shown)

As illustrated in FIG. 21C, the spring-biased hinged door panel 439 is shown arranged in its open configuration so as to permit access to and connection and/or disconnection of the flexible aspiration tubing 430 on the end of the inner cannula (not shown). During typical liposuction and other types of tissue aspiration operations carried out using the liposuction instrument of the present invention, it is expected that the surgeon will need to often change cannulas to perform different types of body sculpturing or contouring operations. To change cannulas, the surgeon will simply slide lever 432 to open the spring-biased door cover 439 and access the base portion of the inner cannula to either connect or disconnect a length of flexible aspiration tubing 430, as the case may be. Thereafter, the surgeon simply snap shuts the hinged door cover 439 and resumes instrument operation.

As shown in FIGS. 20B and 20C, the length the inner cannula 410 which is permitted to undergo during cannula reciprocation operations (i.e. termed cannula stroke length) is controlled by the surgeon during instrument operation by simply rotating the cannula reciprocation stroke control switch 415 with the surgeon's thumb, whereas the rate of cannula reciprocation is controlled by the surgeon depressing the spring-biased cannula reciprocation rate control switch 416 operated by the surgeon squeezing the spring-biased hinged cover panel 439 of the instrument housing.

Figure 21D:
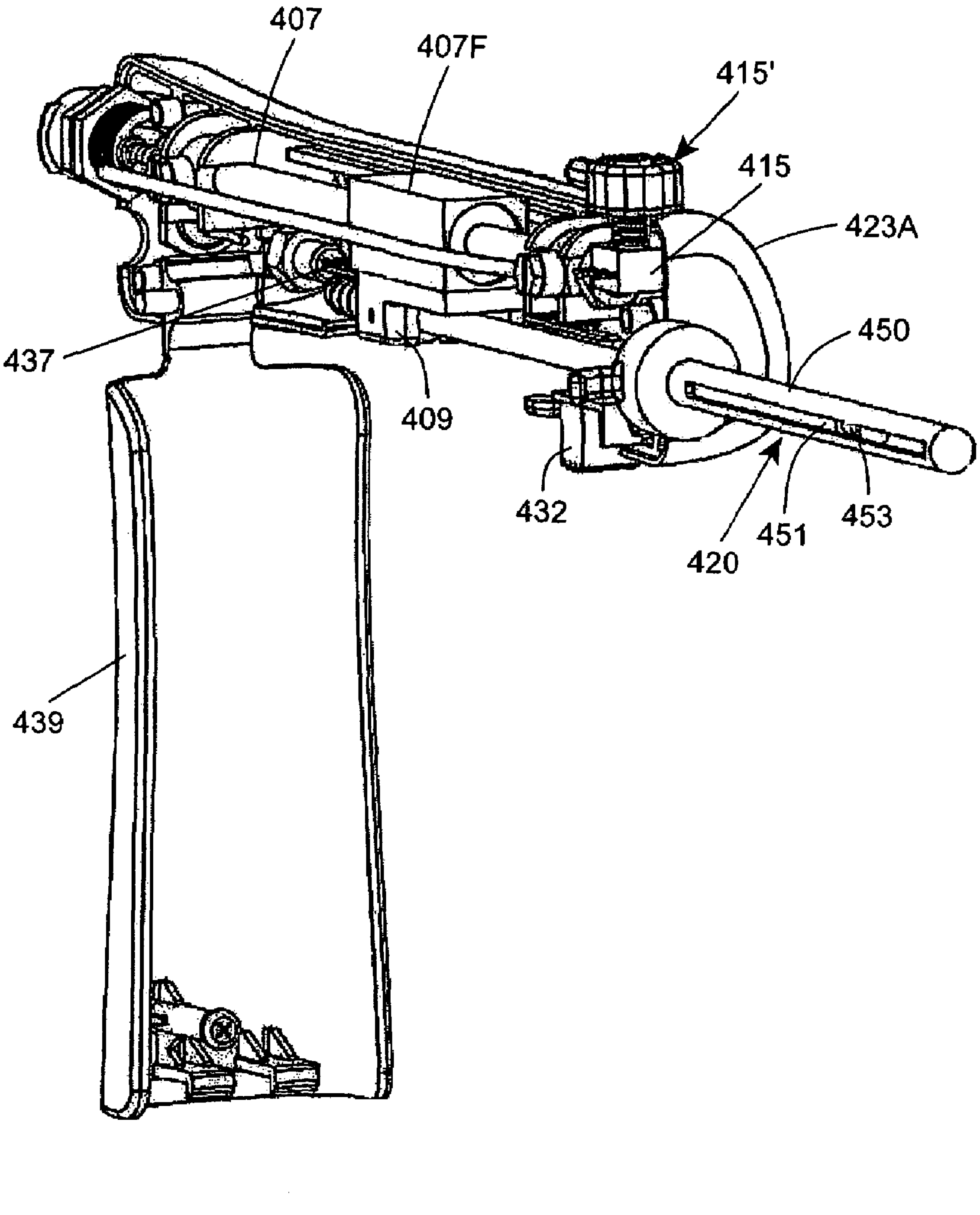
FIG. 21D is a perspective view of the partially-assembled air-powered liposuction instrument of FIG. 20A, shown with its right-half housing portion removed and its hinged spring-biased door panel arranged in its open configuration with its electro-cauterizing cannula assembly installed within the hand-supportable housing of the air-powered liposuction instrument.
Figure 21E:
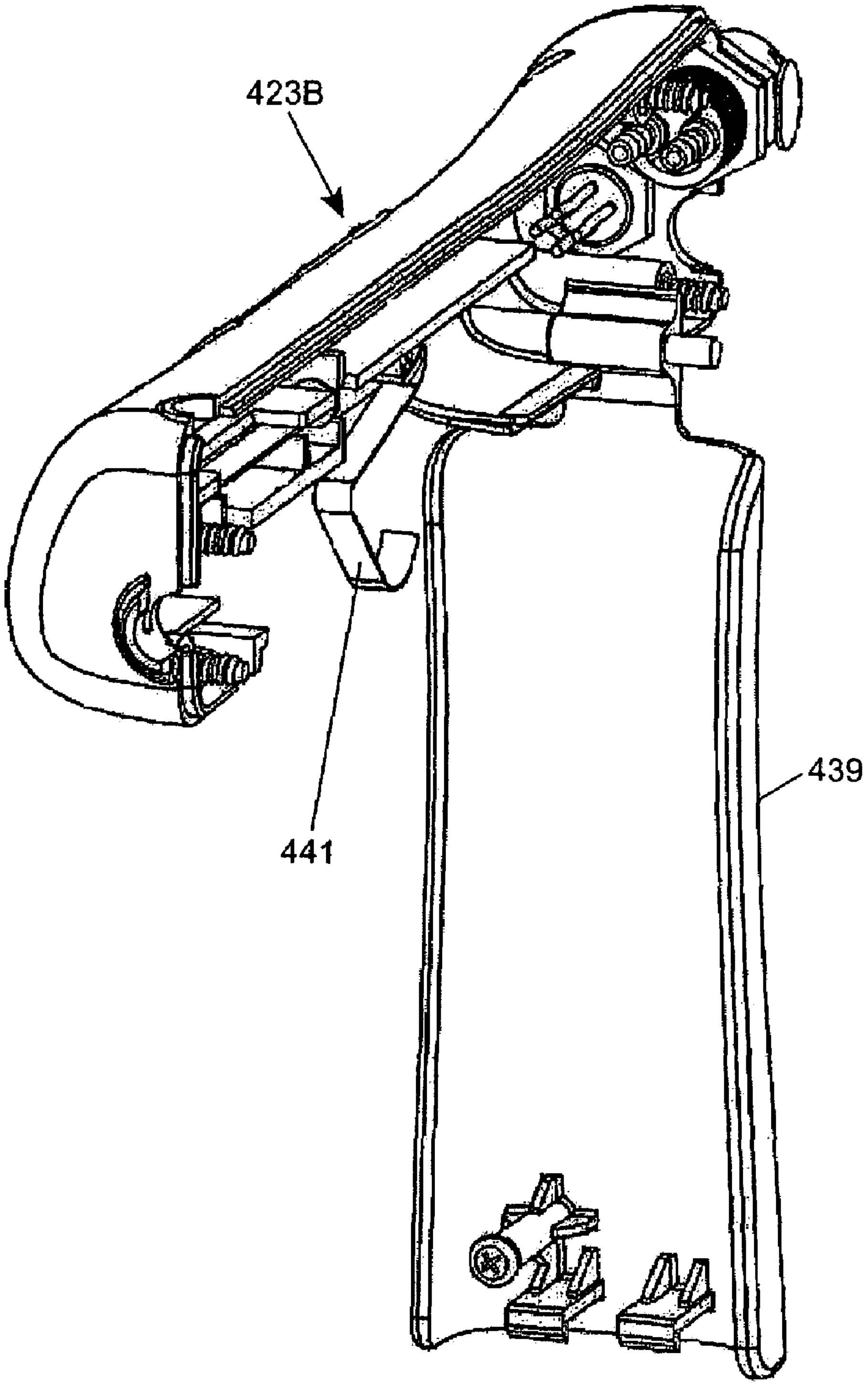
FIG. 21E is a perspective view of the partially-assembled air-powered liposuction instrument of FIG. 20A, shown with its left-half housing portion, its dual-port air-powered cylinder (i.e. reciprocation mechanism), its cannula reciprocation stroke length control switch, its cannula reciprocation rate control switch, and its electro-cauterizing cannula assembly removed from its hand-supportable housing for purposes of illustration, while its hinged spring-biased door panel is shown arranged in its open configuration.
Figure 21F:
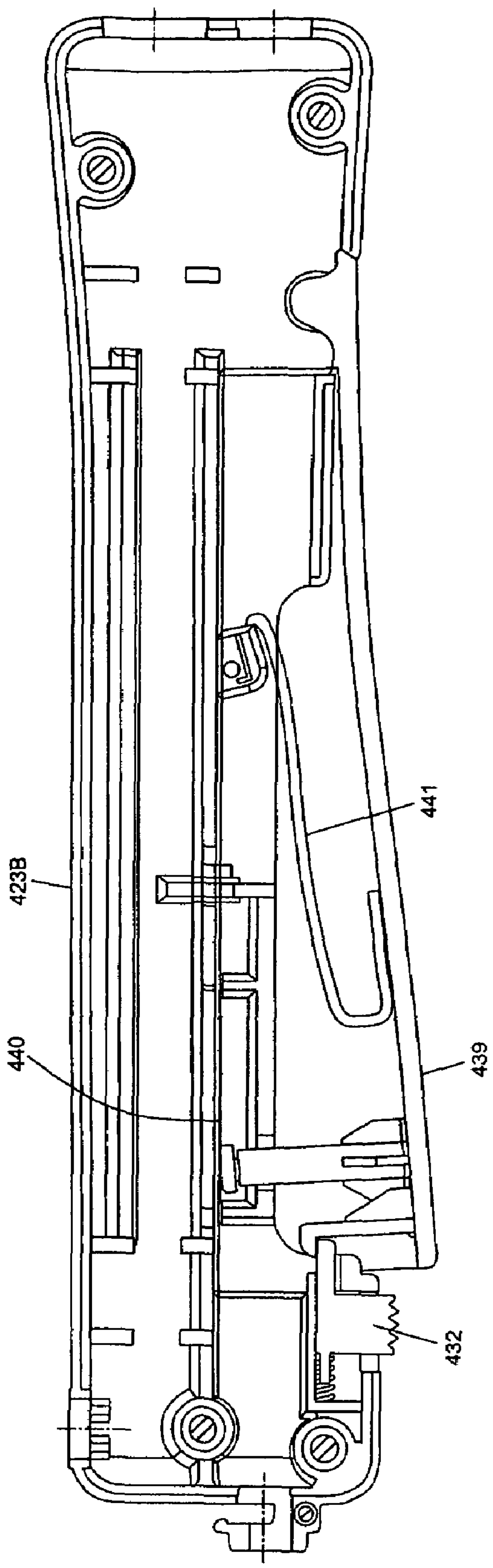
FIG. 21F is an elevated cross-sectional view of the partially-assembled air-powered liposuction instrument shown in FIG. 21E, taken along line 21F-21F indicated therein, with its hinged spring-biased door panel shown arranged in its closed configuration at its "zero" cannula rate control position so as to provide the hand-actuatable cannula reciprocation rate control mechanism of the present invention.
Figure 21G:
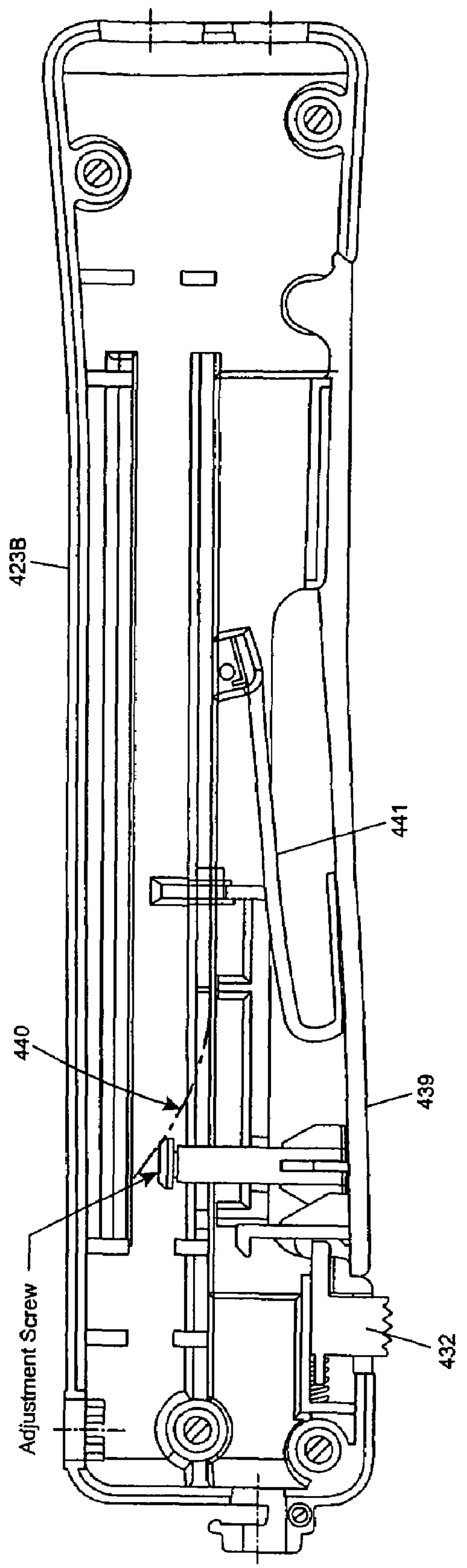
FIG. 21G is an elevated cross-sectional view of the partially-assembled air-powered liposuction instrument shown in FIG. 21E, taken along line 21G-21G indicated therein, with its hinged spring-biased door panel shown arranged in its closed configuration at its "maximum" cannula reciprocation rate control position so as to provide the hand-actuatable cannula reciprocation rate control mechanism of the present invention.

As shown in FIGS. 28A1 and 28A2, the cannula reciprocation stroke length switch (i.e., rotatable potentiometer 415) produces a control voltage which is transmitted to the programmed microprocessor 417 within the instrument controller by way of the electrical control signal cable 411. As shown in FIGS. 28A1 and 28A2, the cannula reciprocation rate control switch 416 (i.e., realized using flexible potentiometer 440) produces a control voltage (upon physical bending or deformation) which is transmitted to the programmed microprocessor 417, also by way of electrical control signal cable 411. The flexible potentiometer 440 used to implement the cannula reciprocation rate control switch 416 can be realized using a variable resistor such as a plastic conductor whose resistance varies upon bending, made by Spectra Symbols, Inc. In FIG. 21F, this flexible potentiometer is shown unflexed (i.e. deformed) with the hinged spring-biased door panel 439 shown arranged in its closed configuration at its "zero" cannula rate control position. In FIG. 21G, the flexible potentiometer 440 is shown unflexed (i.e. deformed) with the hinged spring-biased door panel 439 shown arranged in its closed configuration at its "maximum" cannula rate control position. As shown in FIG. 21E, a spring 442 is used to bias the hinged cover door panel 439. As shown in FIGS. 21F and 21G, this spring applies a biasing force against the hinged cover panel 439 when the panel is arranged in its closed configuration and slidable switch 432 is arranged in its door locked configuration.

Figure 22A:
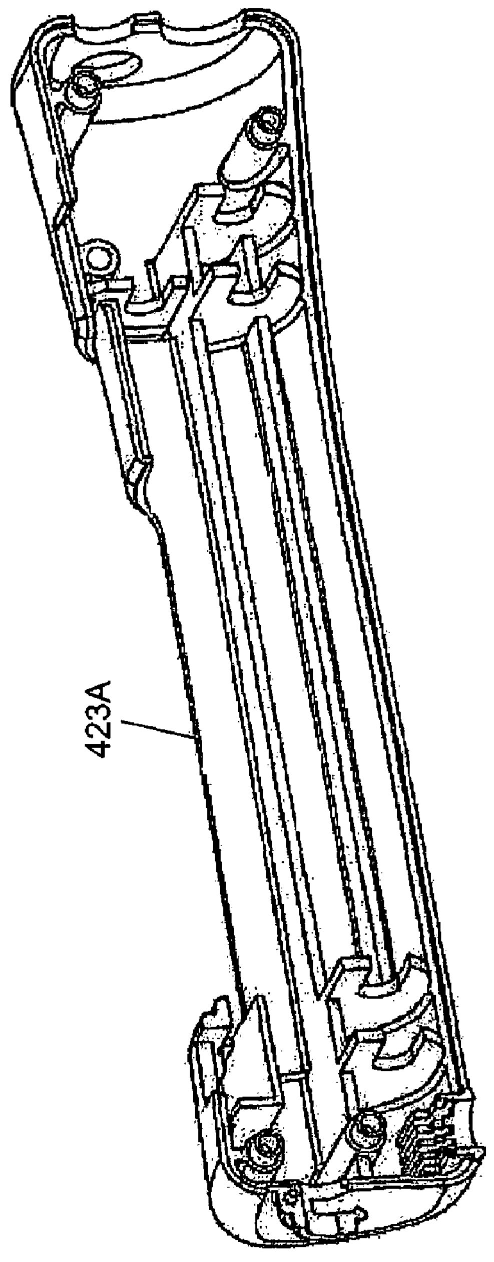
FIG. 22A is a perspective view of the left-half (LH) portion of the hand-supportable housing employed by the air-powered liposuction instrument shown in FIG. 20A.
Figure 22B:
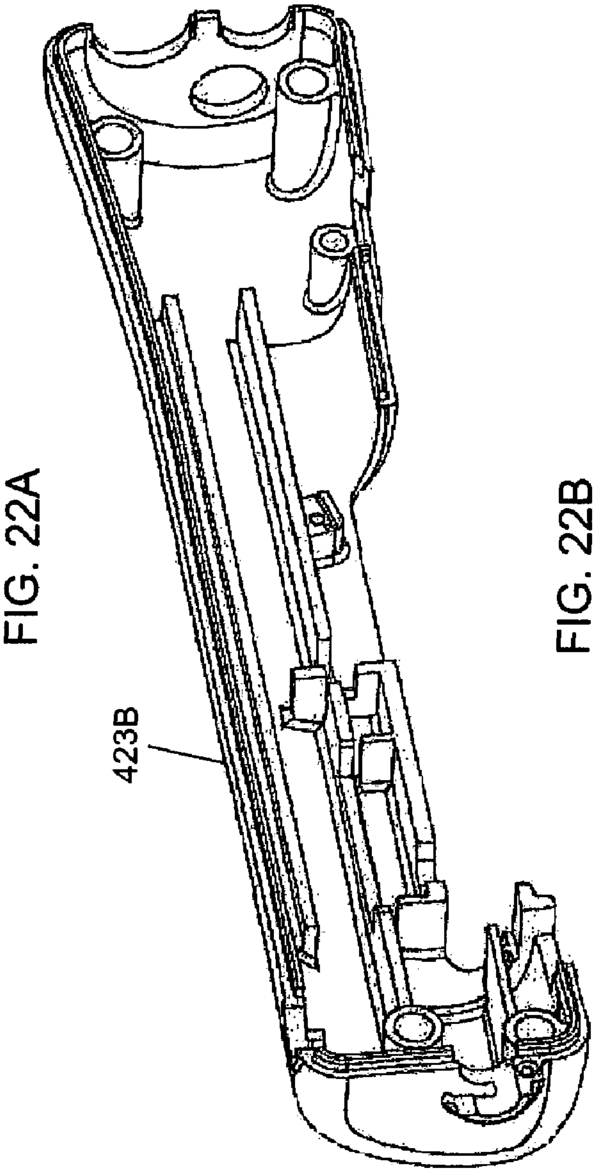
FIG. 22B is a perspective view of the right-half (RH) portion of the hand-supportable housing employed by the air-powered liposuction instrument shown in FIG. 20A.

In FIGS. 22A and 22B, left and right instrument housing halves 423A and 423B are shown in a dissembled configuration with all components removed therefrom. Notably, each housing half has various recesses formed to securely receive particular subcomponents of the instrument and maintain the same in strict alignment upon instrument assembly and operation. Preferably, these housing halves are made from lightweight injected-molded plastic material that can be suitably autoclaved in a conventional manner.

In FIG. 23A, the dual-port air-cylinder structure 407 (e.g., realized as rodless Bimba UG-00704000-B cylinder) is shown arranged in association with its inner cannula actuator position sensing transducer 437, while this assembly is removed entirely from the instrument housing. As shown in FIG. 23B, the base portion of the inner cannula is shown locked within the first recess 434 formed in the carriage structure of the actuator 409, whereas the slidable electrode 433 of the actuator position sensor 437 is adapted for snap-fit receipt in the second recess 435 in the actuator carriage structure 409. In the illustrative embodiment, the actuator position sensing transducer 437 is realized as a slidable linear potentiometer (e.g. as Bourne 53AAA-C20-E13 linear potentiometer) mounted within the instrument housing, as shown in FIGS. 21A, 21B and 21D, with its slidable electrode (i.e. contact) 433 received in the second recess of the actuator carriage 435.

In the illustrative embodiment, the air-cylinder based reciprocation mechanism 407 comprises a tube 407A mounted within a support 407B, and having end air-ports 407C, 407D, and a slidable internally-arranged wall 407E that is magnetically coupled to an external block 407F which is fastened to the actuator 409 by a set of screws or like fastening mechanism. As the cylinder wall 407E is pushed back and forth with tube 407A, under the pressure of air flow streams 406A, 406B delivered to air-ports 407C, 407D by the electronically-controlled air-flow control valve 403 within the instrument controller 402, the actuator reciprocates.

Figure 23C:
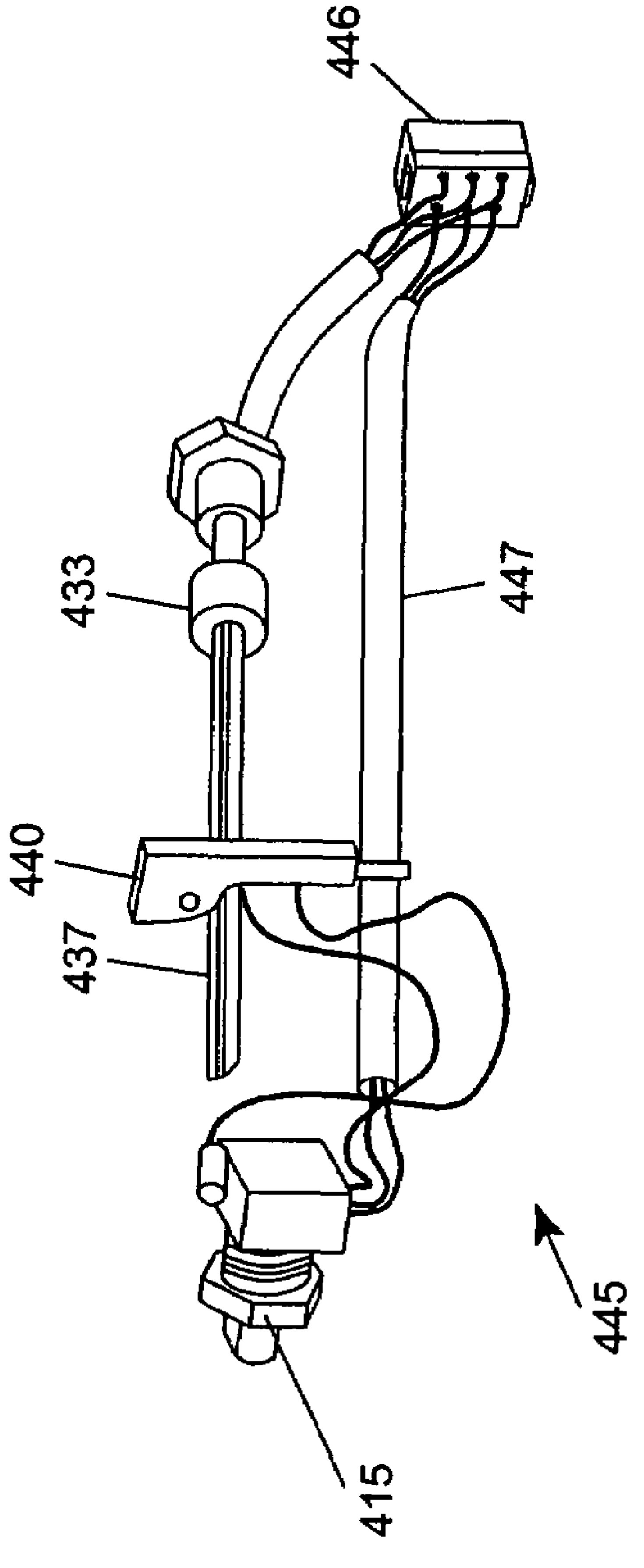
FIG. 23C is a perspective view of the electrical subassembly employed in the air-powered liposuction instrument, shown removed from its hand-supportable housing and comprising its inner actuator position sensing transducer (removed from the carriage portion of the inner cannula reciprocation subassembly), its cannula reciprocation stroke control switch (i.e. slidable potentiometer), its cannula reciprocation rate control switch (i.e. flexible potentiometer), its electrical connector and its electrical wiring harness.
Figures 24A, 24B, 24C:
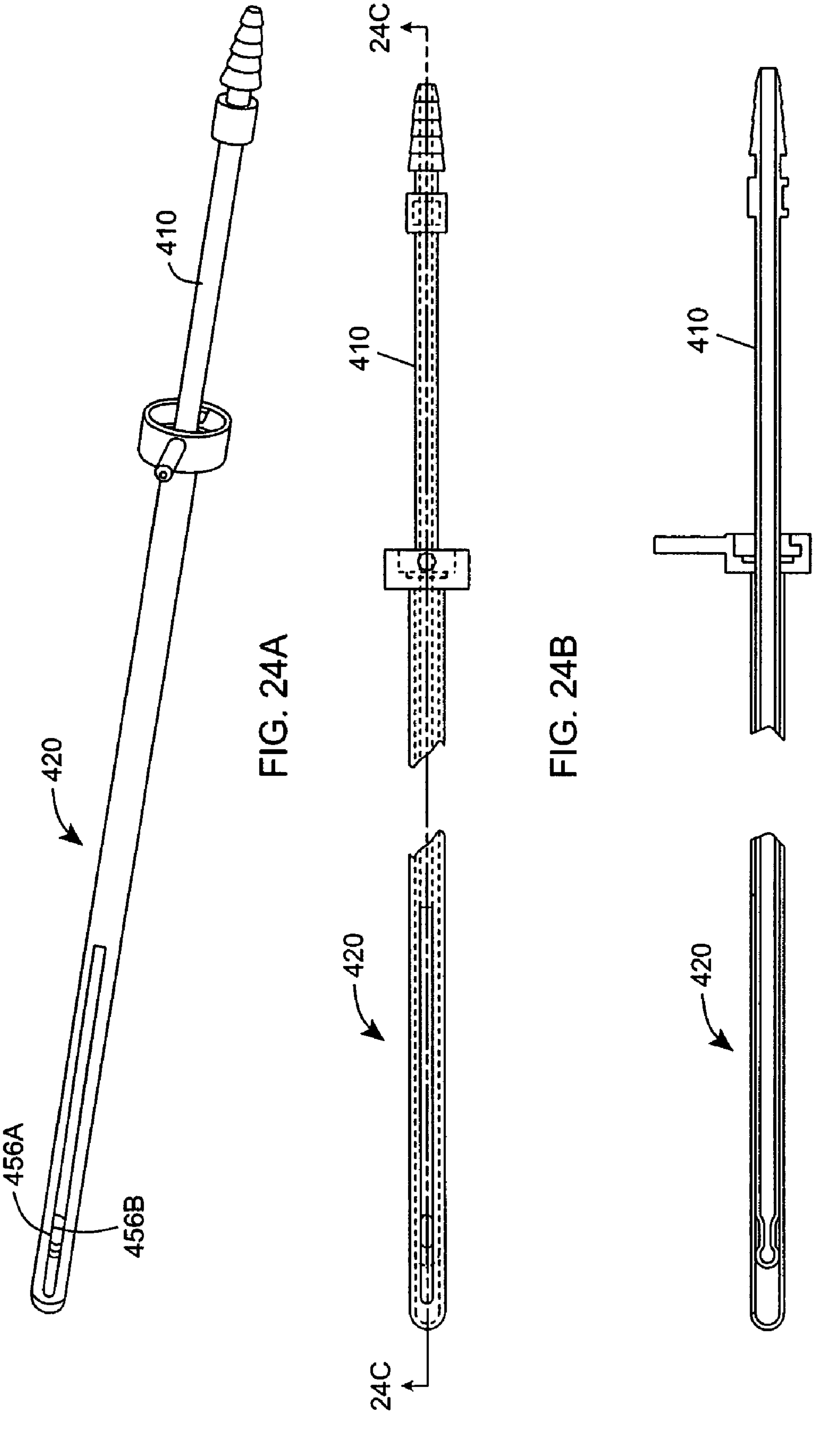
FIG. 24A is a perspective view of the electro-cauterizing dual cannula assembly used in the air-powered liposuction instrument of FIG. 20A.
FIG. 24B is a cross-sectional view of the electro-cauterizing dual cannula assembly shown in FIG. 24A, taken along line 24B-24B indicated therein.
FIG. 24C is a cross-sectional view of the electro-cauterizing dual cannula assembly in FIG. 24A, taken along line 24C-24C indicated therein.
Figures 25A, 25B, 25C, 25D:
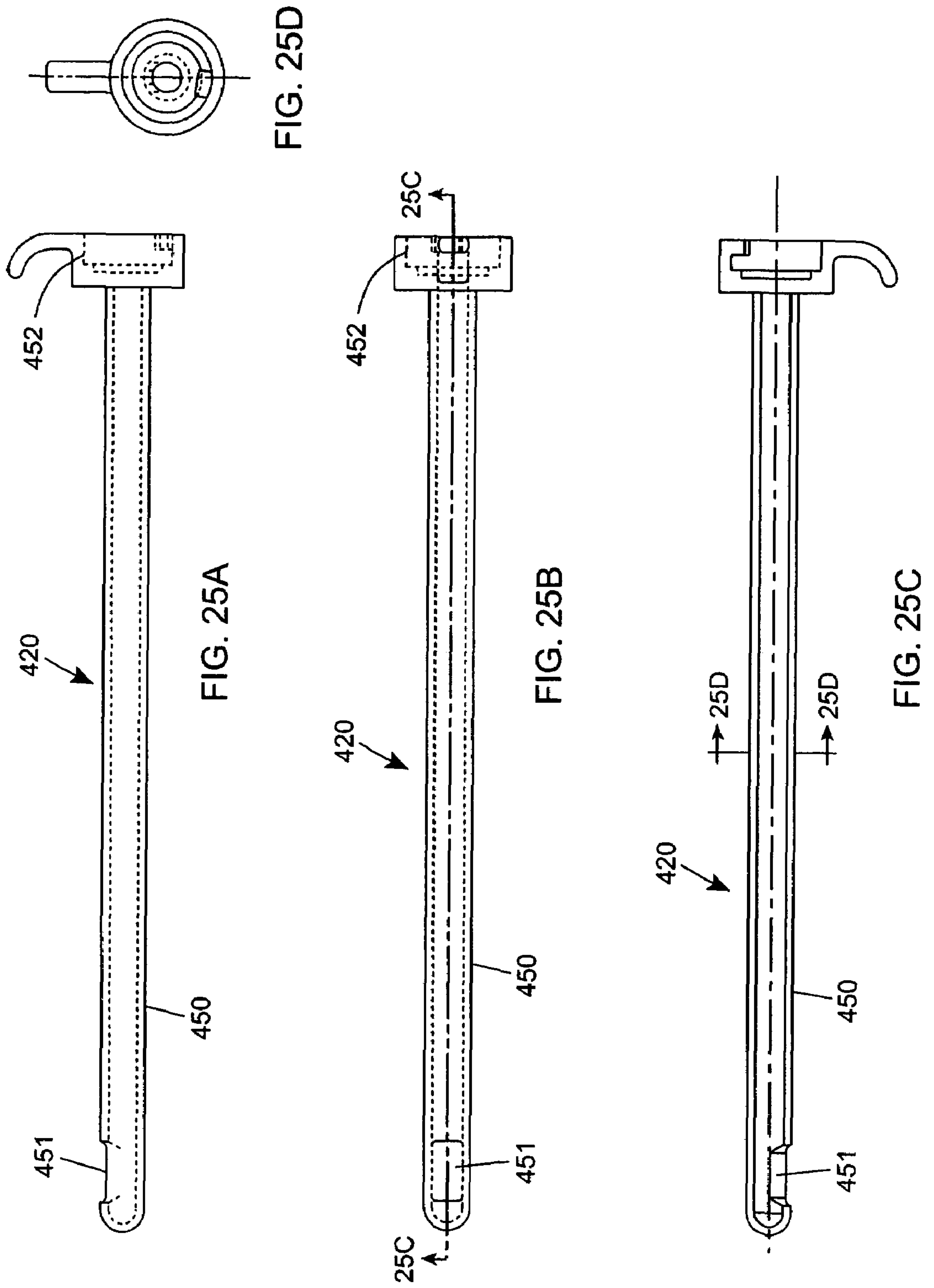
FIG. 25A is an elevated side view of the outer cannula component used in the air-powered liposuction instrument of FIG. 20A.
FIG. 25B is a first cross-sectional view of the outer cannula component used in the air-powered liposuction instrument of FIG. 20A.
FIG. 25C is a second cross-sectional view of the outer cannula component used in the air-powered liposuction instrument of FIG. 20A.
FIG. 25D is a cross-sectional view of the outer cannula shown in FIG. 25A, taken along line 25D-25D indicated therein.
Figures 26A, 26B, 26C:
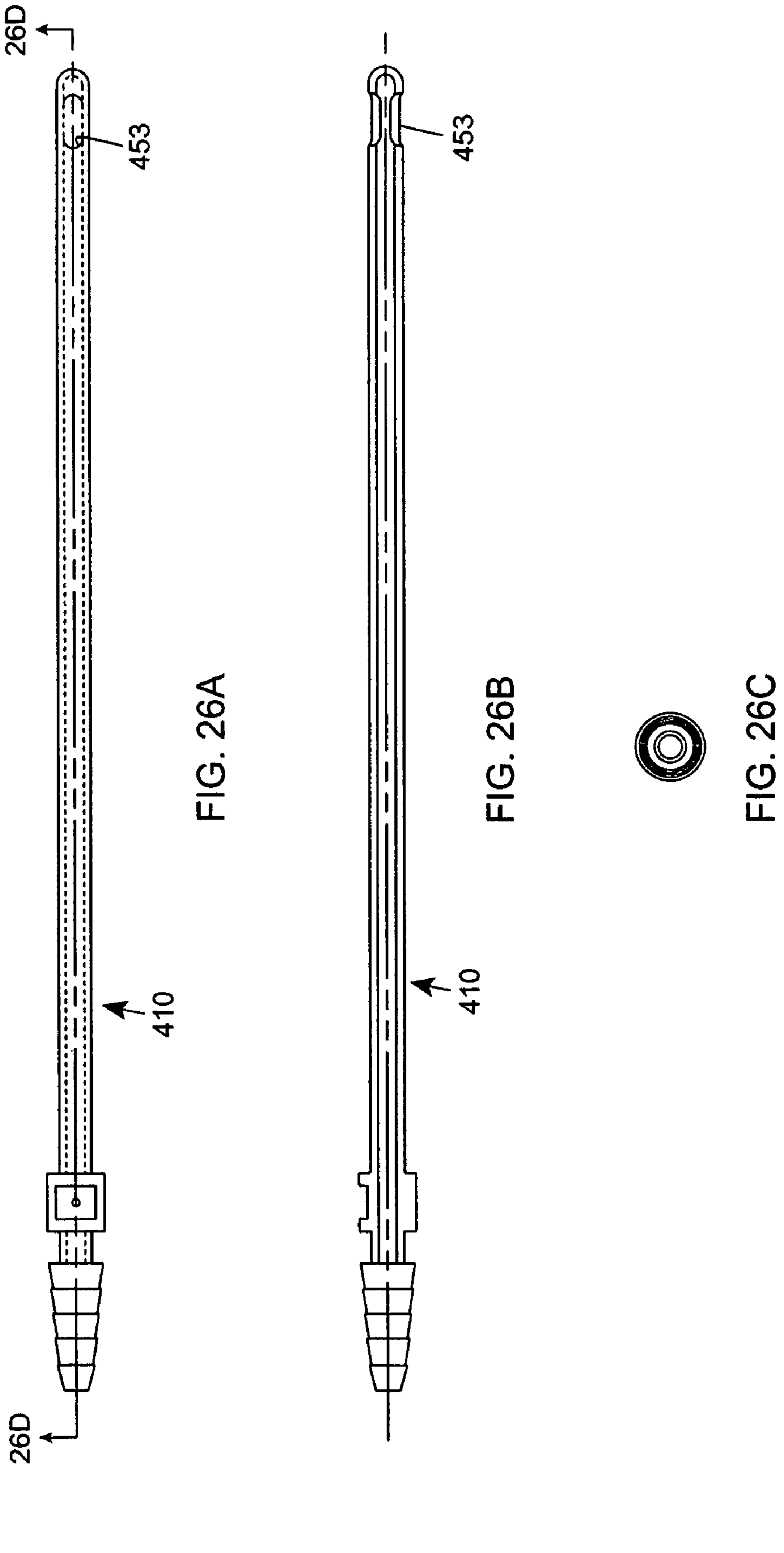
FIG. 26A is an elevated side view of the inner cannula component used in the air-powered liposuction instrument of FIG. 20A.
FIG. 26B is a cross-sectional view of the outer cannula component used in the air-powered liposuction instrument of FIG. 20A, taken along line 26B-26B indicated in FIG. 26A.
FIG. 26C is a cross-sectional view of the outer cannula shown in FIG. 26A, taken along line 26C-26C indicated therein.

In FIG. 23C, the electrical subassembly 445 employed in the powered liposuction instrument 401 is shown removed from its hand-supportable housing. As shown in FIG. 23C, electrical subassembly 445 comprises an assemblage of subcomponents, namely: inner actuator position sensing transducer 433 (removed from carriage structure of the cannula actuator); cannula reciprocation stroke control switch (i.e. potentiometer) 415; cannula reciprocation rate control switch (i.e. flexible potentiometer) 440; electrical connector 446 mounted within the rear end of the instrument housing and connected to the electrical control signal connector 426 described above; and an electrical wiring harness 447 connecting the above electrical components into an electrical circuit specified in the schematic diagram shown in FIG. 30A.

Figure 35A:
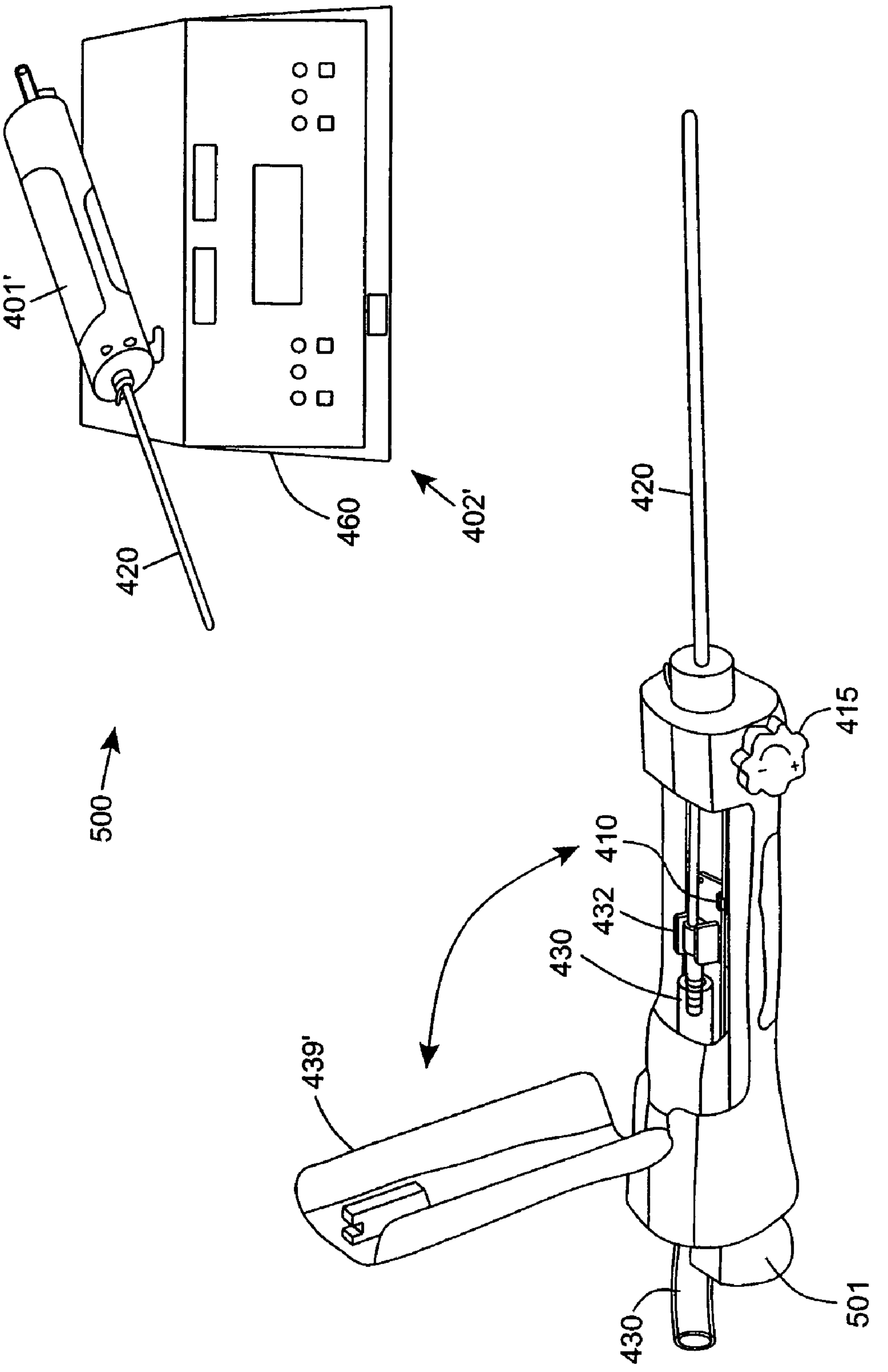
FIG. 35A is a perspective view on yet another illustrative embodiment of the air-powered liposuction instrument system of the present invention comprising (i) a hand-supportable air-powered liposuction instrument having an electro-cauterizing dual-cannula assembly and a multi-core (air-supply/RF-power/control-signal) connector assembly, and (ii) an intelligent instrument controller designed to receive pressurized air flows from an pressurized air source and RF power signals from a RF power signal generator, both external to said intelligent instrument controller.

In FIGS. 25A through 26C, a bipolar electro-cauterizing dual cannula assembly 420 is shown for use with the pneumatically-powered liposuction instrument shown in FIGS. 20A and 35A, and other liposuction instruments described through the present Patent Specification. As shown, dual cannula assembly 420 comprises: stationary outer cannula structure 450 having one or more elongated outer aspiration apertures 451, with a base portion 452 adapted to releasable connection to the front end portion of the hand-supportable instrument housing; and an inner cannula structure 410, slidably received within the stationary outer cannula 450, having one or more inner aspiration apertures 453 in registration with the outer aspiration aspiration apertures 452, and a base portion 431 adapted for snap-fit receipt within the first recess 433 of the carriage portion of the inner cannula actuator 409, described in detail above. The inner cannula 410, detailed in FIGS. 26A through 26C, also has an outlet port 455 formed at its base portion, and is in communication with the inner and outer aspiration apertures for aspiration of tissue during instrument operation. The dual cannula assembly shown in FIGS. 24A through 24B also includes a pair of first and second electro-cauterizing electrodes 456A, 456B realized about the inner and outer aspiration apertures 452 and 451 in order to realize bipolar cauterizing electrodes in proximity with the reciprocating aspiration aperture of the dual cannula assembly, as described in detail hereinabove in connection with other illustrative embodiments disclosed herein. All of these teaching are incorporated herein by reference and applicable to the powered liposuction instrument systems shown in FIGS. 20A, 35A, 35B, and 40A.

Figure 28B:
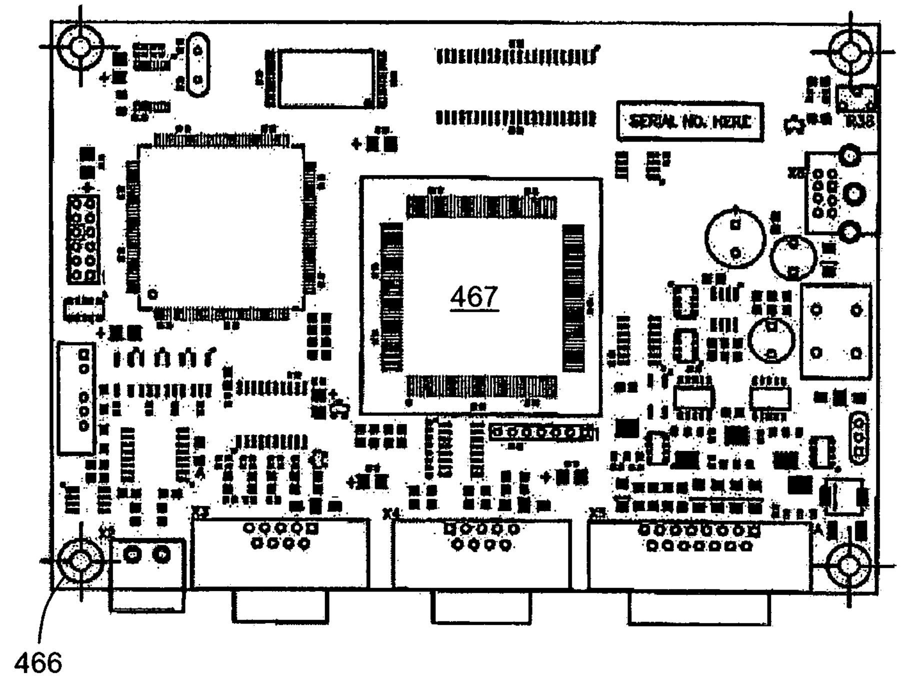
FIG. 28B is the schematic layout of the components used on a prototype circuit board to implement the power console board within the instrument controller schematically described in FIG. 30A.
Figure 29A:
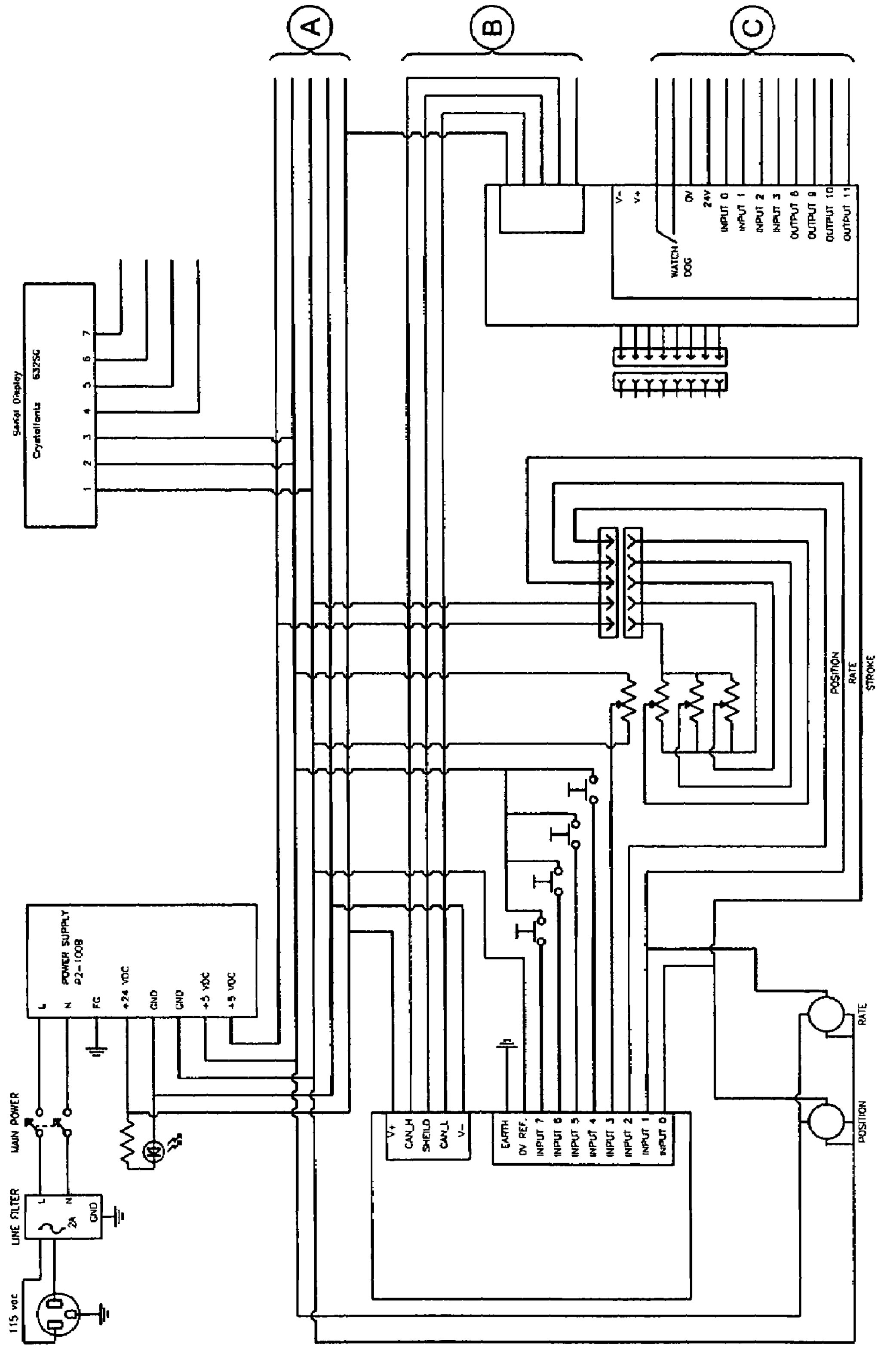
FIGS. 29A and 29B, taken together, set forth an electrical schematic diagram of the analog and digital circuitry realized on the sole PC board shown in FIG. 28B and mounted within housing of the instrument controller shown in FIGS. 27A and 27B and schematically described in FIGS. 28A1 and 28A2.
Figure 29B:
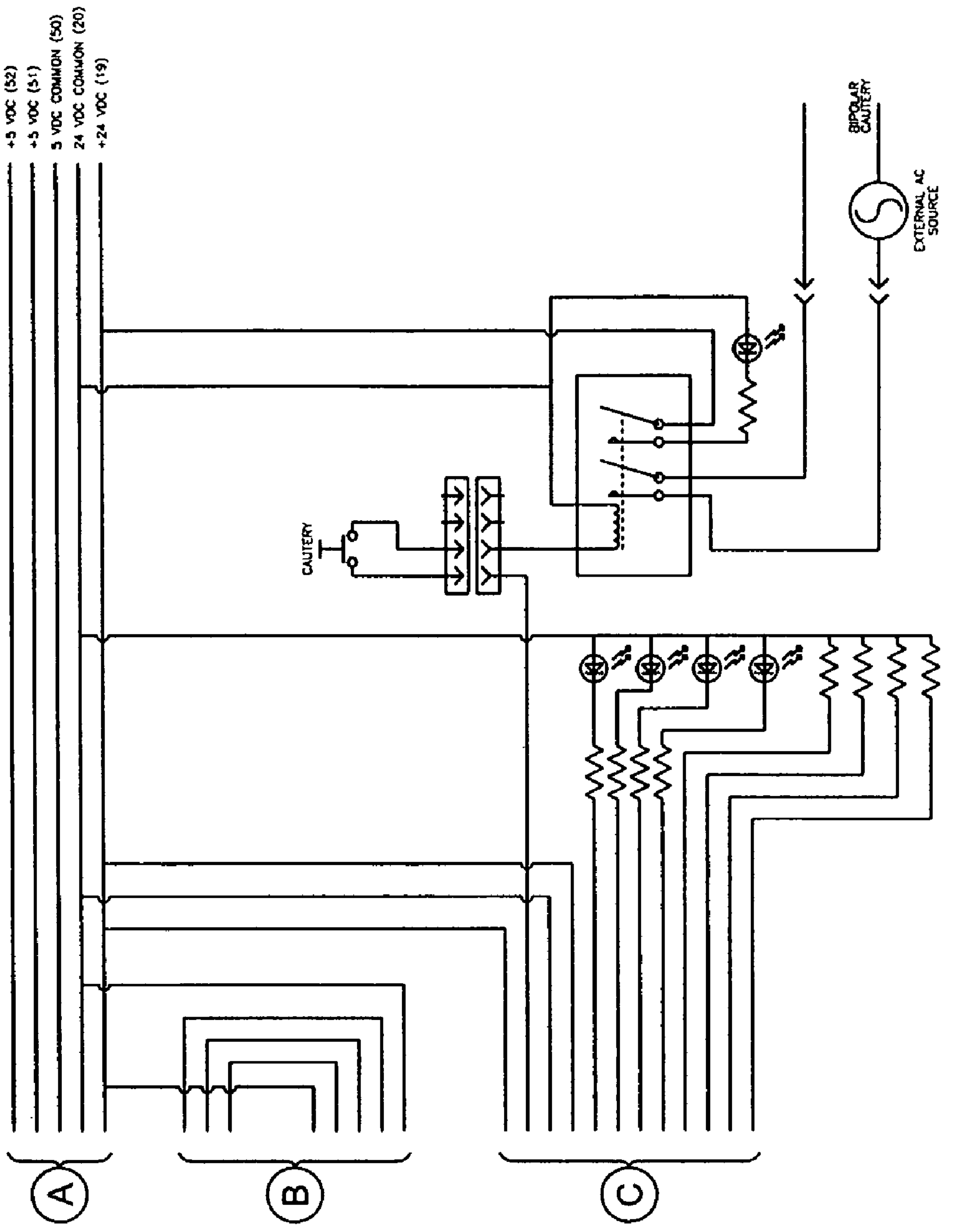

The Intelligent Instrument Controller of the Present Invention Having an Electronically-Controlled Air-Flow Control Valve Assembly, Air-Supply Input/Output Ports and RF Power Signal Input/Output Ports As best shown in FIGS. 27A and 27B, the intelligent instrument controller 402 shown in FIGS. 20A, 27A, 27B, 27C, and 35C comprises: an assembly of components, namely: a housing 430 of compact construction, supporting a pair of air-supply input/output ports 405A and 405B with suitable connectors, a pair of RF power signal input/output ports 404A and 404B with suitable connectors, an input/output electrical control signal port 406 with one or more suitable connectors, and a 24 Volt DC power input supply line 465; a printed circuit (PC) board 466 shown in FIG. 28B supporting the electrical circuits specified in the schematic diagram of FIGS. 29A and 29B, including a programmed application specific integrated circuit (ASIC) 467 functioning as digital signal processor 417 adapted to run various computer programs, including the three BASIC-language expressed computer control programs entitled RECIPROCATE, ANALOG and SCALE set forth in FIGS. 31A through 33C; an electronically servo-controlled air-flow control valve assembly 403 specified in FIG. 30, and realized by mounting four digitally servo-controlled air valves (AFV1 through AFV4) 403A, 403B, 403C and 403D, respectively, within an air flow manifold structure 403E having an air-flow input port 403F (connected to input air-flow supply port on controller housing), a left air-flow output port 403G (connected to the left end of the dual-port air cylinder 407 in the liposuction instrument), a right air-flow output port 403H (connected to the right end of the dual-port air cylinder 407 in the liposuction instrument), a left air-flow exhaust port 403I venting to the ambient atmosphere, and a right air-flow exhaust port 403J venting to the ambient atmosphere, so as to control air-flow valves (AFV1 through AFV4) arranged along air-flow manifold 403E; and an easy-to-read/operate user control console panel 468 comprising (i) four membrane type switches 469, 470, 471 and 472 for selecting a desired cannula stroke length dimension (i.e. inches or centimeters) for measurement and display and for enabling and disabling electro-cautery function selection, (ii) six LED indicators 473, 474, 475, 476, 477 and 478 for indicating power ON/OFF function selection, cannula stroke length dimension selection, and electro-cautery enable/disable function selection, (iii) a pair of LCD-based display panels 479 and 480 for displaying bar graph indications of inner cannula reciprocation rate (in cycles/sec) and inner cannula position measured by the cannula position sensor mounted within the hand-supportable liposuction instrument, and (iv) a LCD-based panel 481, connected to the serial data port of the digital signal processor 417, for displaying measured numerical values for the instantaneous rate of reciprocation for the inner cannula and the instantaneous stroke length thereof.

As shown in FIG. 27B, the bar graphs displayed on LCD panels 479 and 480 offer instantaneous display of the relative position of the inner cannula stroke length rate of inner cannula reciprocation at all times. The LCD panel 481 arranged within the central portion of the console panel 468 offers a more precise digital readout of cannula reciprocation rate and cannula stroke length as well as alert conditions. Notably, cannula stroke length may be displayed in centimeter or inch units by selecting the corresponding membrane switch 469 or 470, respectively.

During system operation, the instrument controller 401 receives an input of pressurized gas (from any of the convenient sources 405 available in operating room settings such as tanked nitrogen gas) at input air flow input port 403F, and generates a pair of pressurized air-flow streams 406A and 406B for supply to the left and right ends (407C, 407D) of the dual-port cylinder 407 employed in reciprocation mechanism of the instrument. These pressurized air-flow streams are generated under the control of digital control signals OP(8) through OP(11) produced by ASIC 480 functioning as a digital signal processor (DSP) 417 and also analog-to-digital converter (ADC) 482 and digital-to-analog converter (DAC) 483. The DSP controls the four air-flow control valves 403A through 403D in a cyclical manner to instantaneously vary the cannula reciprocation rate and stroke length in response to the surgeon's adjustment of the cannula stroke control switch (i.e. spring-biased panel door) and reciprocation rate settings onthe hand-supported instrument housing. The firmness with which the actuator 409 ends each stroke is moderately cushioned by the default factory setting (by adjusting external potentiometer 484 in FIG. 21A) but may be increased or decreased in response to surgeon's preference by trained manufacturer's representatives.

FIGS. 28A1 and 28A2 present a hybrid electrical and mechanical schematic representation of the powered liposuction instrument system of the present invention. As shown, analog voltage input signals are generated from the stroke, position and rate potentiometers 415, 437 and 440 aboard the powered liposuction instrument and supplied as analog input voltage signals to the A/D conversion circuit (ADC) of the ASIC 480 for processing. In response, the DSP 417, running the control programs specified in FIGS. 31A through 33C, automatically generates: (i) digital voltage output control signals OP(8) through OP(11) which are then supplied as output voltage signals to the air-control valve assembly 403 within the intelligent instrument controller 402, so as to generate the pair of pressurized air-supply streams 406A and 406B that are supplied to the liposuction instrument 401; and (ii) a digital control voltage output signal which is converted to an analog control voltage signal by DAC 483, and then supplied to the control input port of the external RF signal source (i.e. generator) 412. In turn, RF signal generator 412 generates an RF power signal and supplies the same to the intelligent instrument controller for controlled delivery to the dual cannula assembly of the powered liposuction instrument via its RF power signal cable structure. The membrane switches 469 and 470 on the control console of the instrument controller enable the surgeon to display selected cannula stroke in centimeters or inches, respectively, on LCD panel 481. Cannula reciprocation rate is automatically displayed on LCD panel 479 in cycles per minute (CPM), alongside cannula stroke length (in centimeters or inches) displayed on LCD panel 480. The membrane switches 471 and 472 on the control console enable the surgeon to enable and disable bipolar electrocauterization, respectively.

FIG. 28B sets forth a schematic layout of the components (e.g. ASIC 480) used on the prototype printed circuit (PC) board 466 within the intelligent instrument controller schematically described in FIGS. 28A1 and 28A2. The electrical components appearing on this board are shown in the schematic diagram set forth in FIGS. 29A and 29B.

FIGS. 29A and 29B, taken together, set forth an electrical schematic diagram of the analog and digital circuitry realized on the sole PC board 466 shown in FIG. 28 and mounted within the intelligent instrument controller.

As shown in FIG. 30, the servo controlled air-flow valve assembly of the present invention enable the reliable control of three basic kinds of pressurized air-flow streams between the liposuction instrument 401 and its instrument controller 402, namely: (i) the flow of pressurized air from the central air-flow input port 403F to either the left air-flow input/output port 403G or right air-flow input/output port 403H; (ii) the flow of pressurized air from the left air-flow input/output port 403F to the left air-flow exhaust port 403I; and (iii) the flow of pressurized air from the right air-flow input/output port 403F to the right air-flow exhaust port 403J. In general, control of the air-powered cannula reciprocation mechanism within the instrument is carried out by the programmed DSP 417, in a manner independent of the electro-cauterizing functionality of the system.

As shown in FIGS. 31A through 31D, the primary control program entitled RECIPROCATE is run on the DSP 480 within the instrument controller. In the illustrative embodiment, this control program functions as the primary control thread calling programs ANALOG and SCALE, as second and third control threads running within the first control thread.

As indicated at Block A in FIG. 31A, under the caption "Initialize", the control program RECIPROCATE launches the subprogram ANALOG to read potentiometer inputs 415, 437 and 440 corresponding to the desired stroke, position, rate and cushion settings on the instrument, and then the program RECIPROCATE calls the subprogram SCALE to scale these variables. When either the stroke control knob 415 is turned to zero, or the trigger 439 is released, the software program RECPIROCATE positions and locks the inner cannula 410 in the forward position and turns the reciprocation "off" so that the inner cannula may be changed or removed from the hand-supportable housing. The program RECIPROCATE then reads the control console keypads 469-472 and controls its LEDs 473-478 to default settings. Then the program resides in its "attention state" until it is engaged into its "reciprocation state" by the surgeon moving the cannula stroke and rate controls 415 or 440 to non-zero positions.

As indicated at the extended block of code indicated as Block B in FIGS. 31A-31C, under the caption "reciprocation", the software RECIPROCATE checks to determine that both the cannula stroke and rate controls are moved to non-zero values by the surgeon/operator, and if so, then controls the LCD panels and LEDs accordingly, and then checks to determine if the electro-cautery option has been selected. If so, the RECIPROCATION program drives the electro-cautery solenoid relay 421.

As indicated at Block B1 in FIG. 31C, the RECIPROCATION program thereafter drives the inner cannula in its "backstroke" direction by generating the sequence of digital control signals OP(10,0), OP(11,1), OP(8,0), OP(9,1). As indicated at Block B2, the RECIPROCATION program sets a cushion-back control over the movement of the inner cannula in the backstroke direction (achieved by clamping the exhaust valve to slow down air exhaust and permit compression of air within the cylinder in the back-stroke direction).

As indicated at Block B2, this cushion-back control is dependent upon a "test-stroke" routine, in which the RECIPROCATION program tests whether the inner cannula stroke control has been set by the surgeon/operator equal to or below a predetermined "short" stroke position. In the event that the stroke control value has been set equal to or below the predetermined short stroke position, then the RECIPROCATION program skips setting cushion-back control, and sets a timer, during which the inner cannula is permitted to travel to its predetermined backstroke position before being automatically driven in the return stroke direction to its forward home position, and such inner cannula reciprocation operations repeated in a cyclical manner. Then, secondly, the RECIPROCATION program checks to determine whether or not the inner cannula reaches its target stroke position, as specified by the cannula stroke control manually set by the surgeon. If the inner cannula reaches it target stroke position, then the RECIPROCATION program checks advances to the "return stroke" routine set forth at Block B3. If the timer lapses before the inner cannula reaches it target stroke position, then the RECIPROCATION program checks advances to the "return stroke" routine set forth at Block B3.

As indicated at Block B3 in FIG. 31D, the return-stroke routine involves the RECIPROCATION program driving the inner cannula in its "return stroke" direction by generating the sequence of digital control signals OP(9,0), OP(8, 1), OP(11,0), OP(10,1).

As indicated at Block B4 in FIG. 31D, the RECIPROCATION program sets a cushion-front control over the movement of the inner cannula in the return-stroke direction (achieved by clamping the other exhaust valve to slow down air exhaust and permit compression of air within the cylinder in the return-stroke direction).

At Block B4, this cushion-front control is dependent upon a "test-home" routine set forth at Block B5 in FIG. 31E. The RECIPROCATION program sets another predetermined time period and determines whether the inner cannula reaches the stroke position manually set by the surgeon/operator using the inner cannula stroke control switch 415' within the predetermined time period. Also, a check is set up at Block B6 in FIG. 31E to determine that control threads ANALOG and SCALE are running. In the event that the inner cannula reaches the stroke position manually set by the surgeon/operator within the predetermined time period, then the inner cannula is automatically driven in the back stroke direction, and such inner cannula reciprocation operations repeated in a cyclical manner. If the inner cannula does not reach it target stroke position during the predetermined time period, then the RECIPROCATION program repeats the reciprocation loop. Only in the event of catastrophic failure or operation does the RECIPROCATION program enter the "loop exit" routine where the cylinders are automatically vented and the control thread for ANALOG and SCALE subroutines.

As shown at Block A1 in FIG. 32A, the ANALOG subprogram first initializes the "Global Variables" used by the subprogram. At Block A2, the ANALOG subprogram initializes the "Local Variables" used by the subprogram. Then at Block C, the analog program gets instrument feedback.

At Block C in FIG. 32B, the subprogram ANALOG measures the range of the rate control switch flexible potentiometer 440.

At Block D in FIG. 32B, the subprogram ANALOG reads the cannula stroke and rate control switches 415 and 440 to confirm that the both controls are set to non-zero values. Then at Block E, the subprogram ANALOG reads the cannula position transducer (i.e. analog position encoder) and analyzes the sensed position value against the last position value so as to determine whether or not the inner cannula is moving or is stationary. At Block F, the subprogram ANALOG stores the present cannula position value in memory for use in comparison operations performed during the next control loop in the program RECIPROCATE. Then, at Block G, the subprogram ANALOG determines whether (i) both the cannula stroke and rate control values are non-zero, and (ii) the inner cannula is moving, and if these two conditions hold, then the variable VR(9) is set to 1; otherwise VR(9)=0.

At Block H in FIG. 32B, the subprogram ANALOG determines whether the surgeon/operator has selected the electro-cautery option, by depressing the corresponding control pad on the control console 468, and if so, then sets the variable VR(10) to 1, and 0 if no electro-cautery is desired.

Then at Block I in FIG. 32C, the subprogram ANALOG checks if electro-cautery has been selected, and if so then sets the enable electro-cautery variable VR(11) to 1, and to 0 if this option has not been selected. At Block J, the subprogram reads the control pads to determine if the stroke position has been changed to centimeters, and if so, then sets the variable VR(12) to 1, or to 0 if units should be in default units of measurement (i.e. inches).

As shown at Block A in FIG. 33A, the SCALE subprogram first initializes the "Global Variables" used by the subprogram. Then, at Block A1, the SCALE subprogram initializes the "Local Variables" used by the subprogram. At Blocks B1 through B3 in FIG. 33B, the subprogram SCALE takes analog input voltages from the ANALOG subprogram and converts them into corresponding digital voltage values for use by the program ANALOG. At Block C in FIGS. 33B and 33C, the subprogram SCALE assigns instrument parameters such as rate-delay, stroke-length, and stroke-time to variables computed in accordance with formulas set forth in the SCALE subprogram. Notably, the constants $C_1$ through $C_8$ used in these formulas (set forth at Block B3) can be empirically determined in the laboratory without undue experimentation, and will be dependent on the technology used to implement the instruments and systems of the present invention. Blocks D, E and F in FIG. 33C are provided to ensure a reliable system design.

Figure 34:
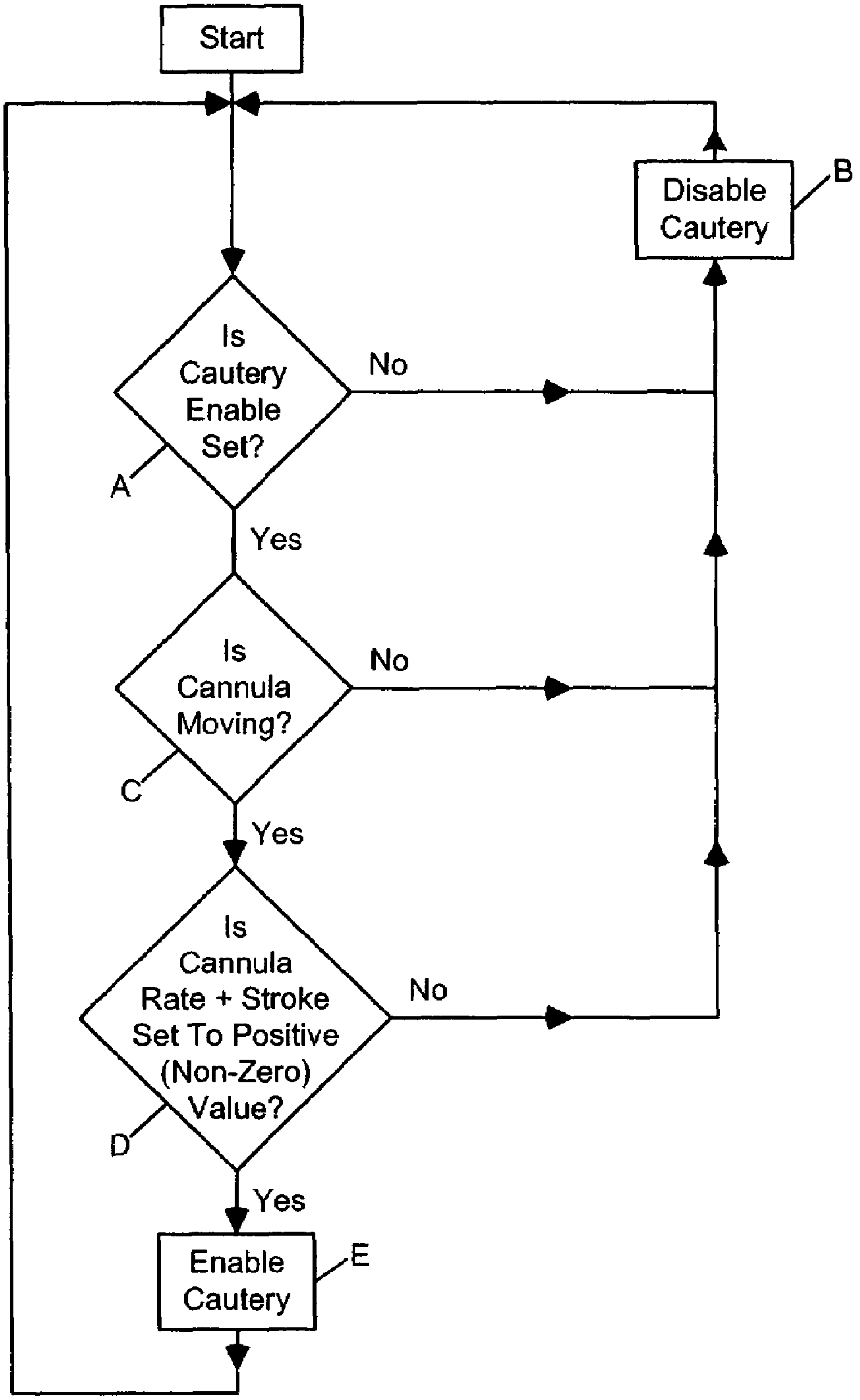
FIG. 34 is a high-level flow chart of a electro-cautery enable/disable control process carried out by the control program performed collectively by the programs RECICPROCATE, ANALOG and SCALE illustrated in FIGS. 31A through 33C.

In FIG. 34, a high-level flow chart of the electro-cautery control process of the present invention is shown. While this control process is embodied within the control process carried out by the programs RECIPROCATION, ANALOG and SCALE, described above, this control process is summarized in the flow chart of FIG. 34.

As indicated at Block A in FIG. 34, the control process determines that the electro-cautery option has been selected by the surgeon on the control console. If not, then the control thread advances to Block B where the cautery is disabled before returning to the top of the control thread (Start). If the electro-cautery option has been selected, then the control process advances to Block C where it determines that the cannula stroke and rate controls are non-zero. If not, then the control flow returns to Block B where electro-cautery is disabled. If the cannula stroke and rate controls are non-zero, then the control flow advances to Block D where it determines whether the inner cannula is moving, as determined by its motion sensing apparatus. If not, then the control process returns to Block B where electo-cautery is disabled. If the inner cannula is moving, then the control process advances to Block E where the electro-cautery is enabled before the control process returns to the beginning of the control loop. This process is repeated in a cyclical manner. In the event that the surgeon manually switches either the cannula stroke length or rate to zero value, or the cannula stops moving, then automatically the control process of the present invention will automatically disable the electro-cautery function of the power-assisted liposuction instrument of the present invention.

In summary, the RECIPROCATION program drives the inner cannula back and forth within the hand-supportable instrument by generating "backstroke" and "return stroke" digital control signals which are supplied to the electronically-controlled multi-value air-flow assembly 403. When being driven in the backstroke direction, the RECIPROCATION program automatically checks to determine whether or not the surgeon has manually selected a "short-stroke" value (determined against a predetermined reference), and if so, avoids setting up a cushioning control in the backstroke direction. When being driven in the return-stroke direction, the RECIPROCATION program automatically checks to determine whether or not the inner cannula has traveled, during the predetermined time period, to the cannula stroke position value set by the surgeon/operator, and if so, automatically generates the appropriate digital control signals for the return stroke operation. For electro-cautery option to be enabled, the RECIPROCATION program must detect non-zero values set for the cannula stroke-length and rate controls, as well as detect that the inner cannula is in fact moving within the stationary outer cannula. If one of these conditions is not satisfied, then automatically the instrument controller disables the electro-cautery function of the instrument system.

Air-Powered Liposuction Instrument System Having a Multi-Core Cable Construction and an Intelligent Instrument Controller with an Electronically-Controlled Air-Flow Control Valve Assembly and RF Power Signal Input/Output Port In FIG. 35A, there is shown another illustrative embodiment of the powered liposuction instrument system of the present invention 500, comprising: an intelligent instrument controller 402' as generally shown in FIGS. 27A through 34 and described above, and having a multi-core connector assembly 501, as shown in FIGS. 36B through 36E, for connecting to the air supply lines, electrical control lines and RF power supply lines within the instrument controller 402'; a hand-supportable air-powered liposuction instrument 401', as generally illustrated in FIGS. 20A through 20C and described above, and having an electro-cauterizing dual-cannula assembly 420 as shown in FIGS. 24A through 26C, and a multi-core connector assembly 501B as shown in FIGS. 36B through 36E for connecting to the air supply lines, electrical control lines and RF power supply lines within the hand-supportable instrument 401'; and a flexible multi-core cable construction 502 shown in FIGS. 36A through 36H, including first and second multi-core connector plugs 503A, 503B, multi-core cable 504, rubber shroud covers 505, assembled for interconnecting multi-core connector assemblies 501A and 501B and thus establishing communication between the corresponding the air-supply lines, the electrical control lines and the RF-power supply lines within the instrument 401' and its system controller 402'.

Figure 36A:
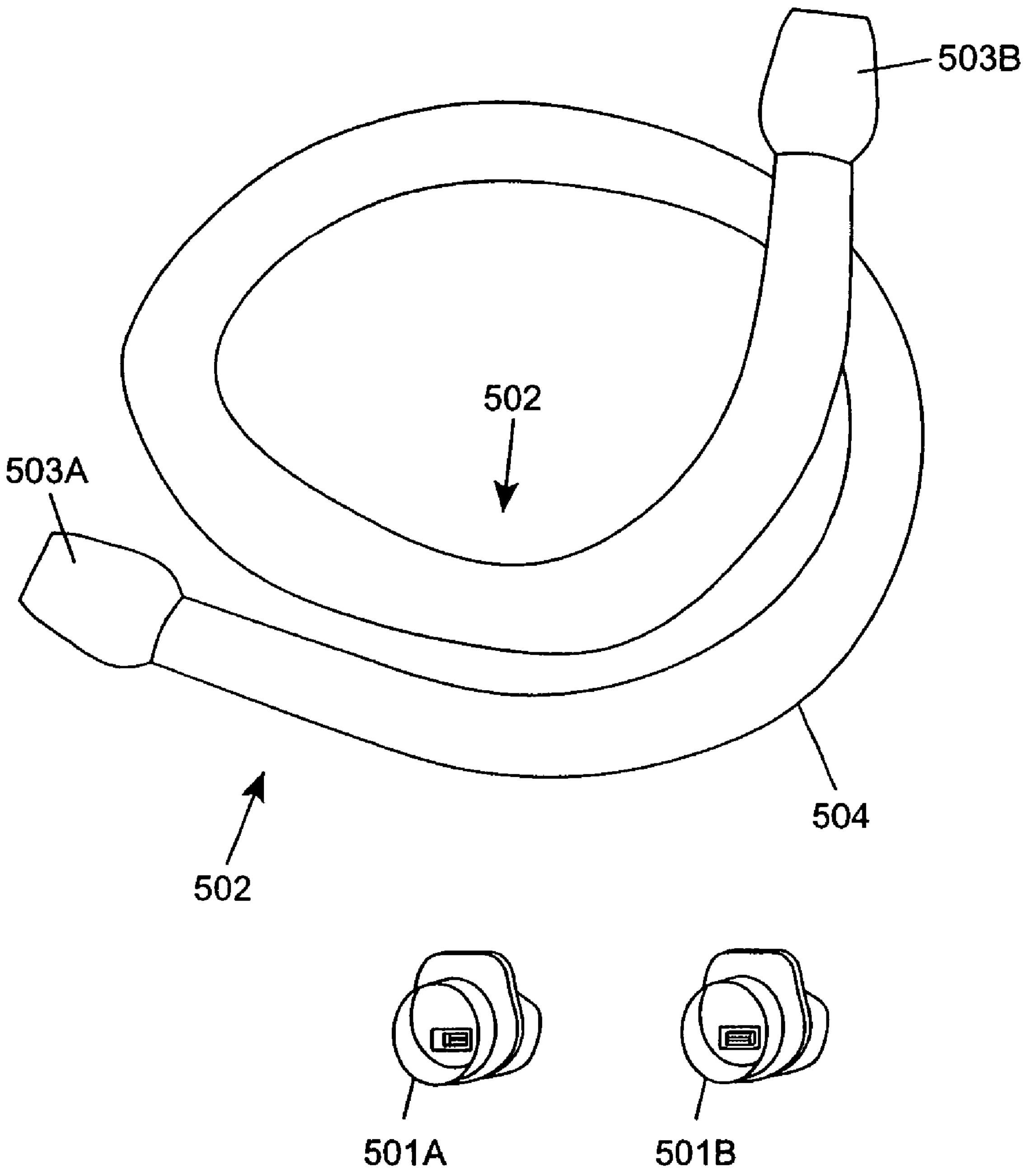
FIG. 36A is a perspective view of the multi-core cable construction of the present invention employed in the air-powered liposuction instrument shown in FIG. 35A, shown removed from the hand-supportable instrument and instrument controller, neatly coiled up to reveal the connectors mounted on each end of the cable construction, and arranged for display in relation to a pair of matched multi-port connectors employed therein, wherein one of these connectors is adapted for installation within the air-powered liposuction instrument, whereas the other connector is adapted for installation through the housing of the intelligent instrument controller of the present invention.
Figure 36B:
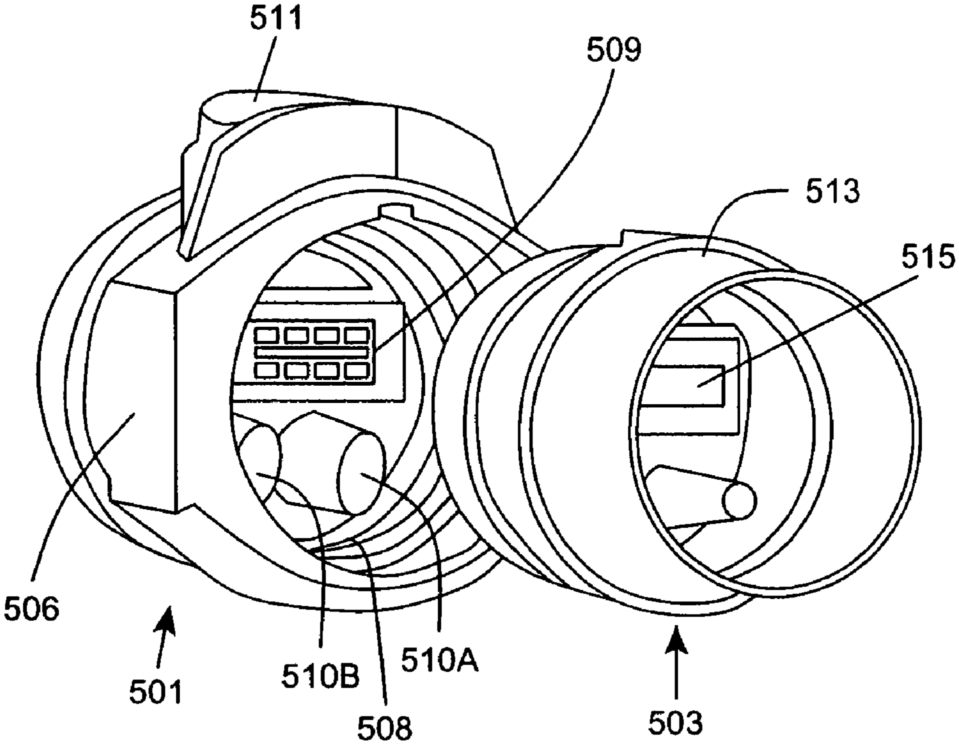
FIG. 36B is a perspective view of the multi-port connector assembly of the present invention employed in the multi-core cable structure of FIG. 35A, showing (i) its first multi-port connector adapted for installation in the rear end portion of the powered liposuction instrument housing as well as through the wall of the intelligent instrument controller (as the case may be) and having a pair of pressurized air-flow ports, and one multi-pin electrical port for supporting the communication of RF power signals between the instrument controller and liposuction instrument and the communication of electrical control signals between the instrument controller and liposuction instrument shown in FIG. 27A, and (ii) its second multi-port connector mated to the first multi-port connector and adapted for connection to the multi-core cable structure of the present invention comprising a pair of air-supply tubes, a pair of RF power signal wires, and a set of electrical control signal wires, all of which is encased within a flexible plastic casing, as shown.
Figure 36C:
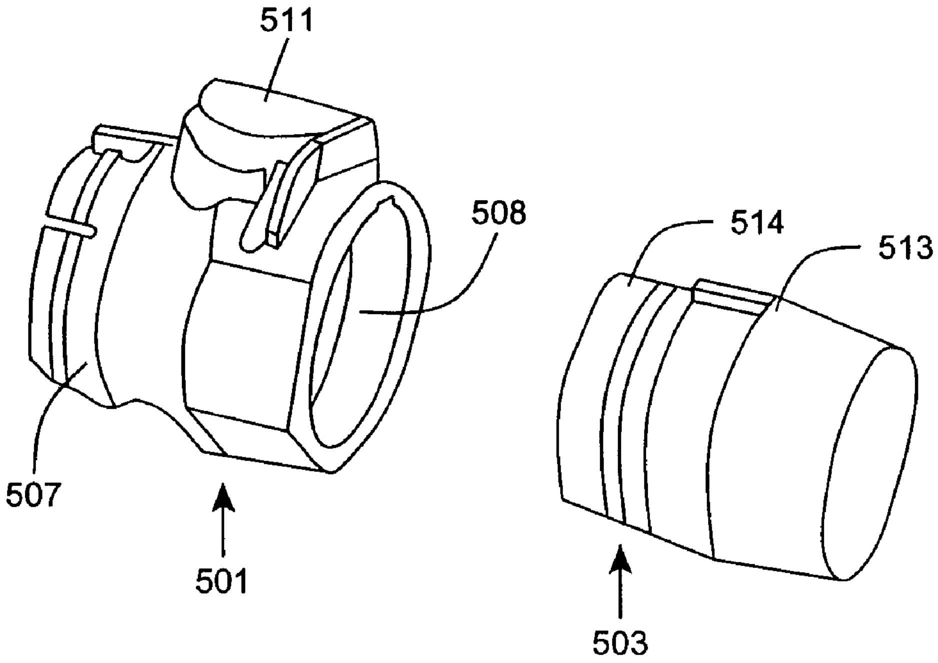
FIG. 36C is an alternative perspective view of the multi-port connector assembly of the present invention shown in FIG. 36B.
Figure 36D:
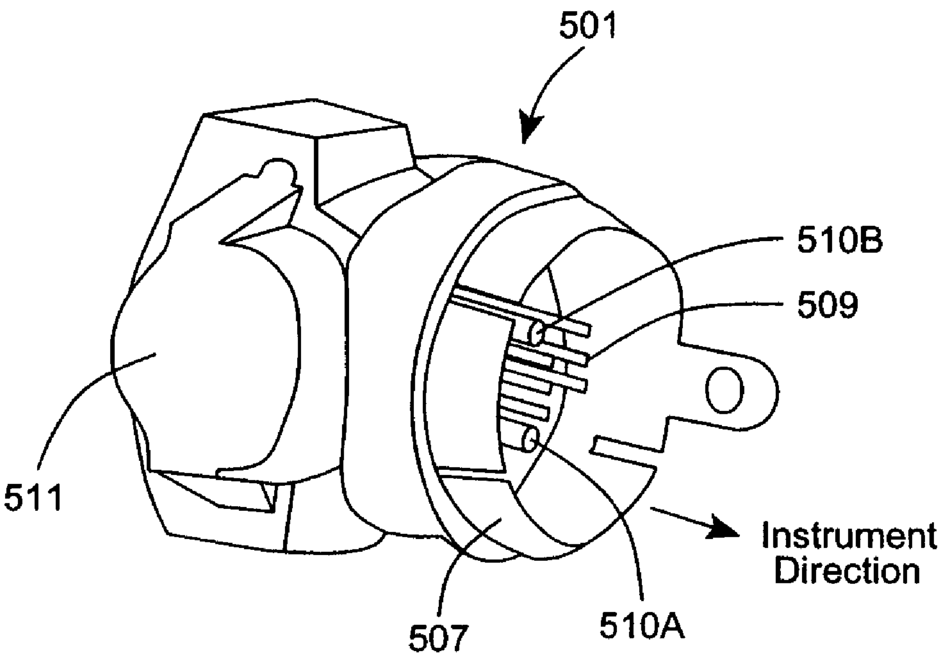
FIG. 36D is a perspective view of the first multi-port connector employed in the multi-port connector assembly of FIG. 35A, viewed from the side which connects to air tubing and electrical wiring contained within the hand-supportable air-powered liposuction instrument (or within the intelligent instrument controller shown in FIG. 37A, as the case may be)
Figure 36E:
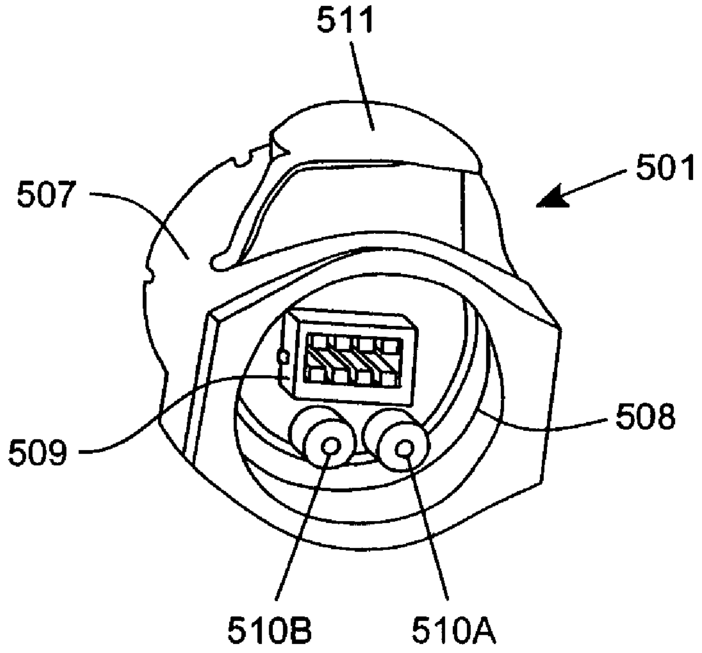
FIG. 36E is a perspective view of the first multi-port connector employed in the multi-port connector assembly of FIG. 35A, viewed from the side which connects to the second multi-port connector of the assembly of FIG. 35A.

As shown in FIG. 36B, each multi-core connector assembly 501A, 501B comprises: a plastic housing 506 having a cylindrical mounting portion 507 designed to be received within a mated portion of the hand-supportable housing of instrument 401', or the instrument system controller 402', as the case may be, and also a cylindrical recess 508 for receiving the cylindrical end portion of a quick-connect multi-core plug 503, as shown; a pin connector 509 mounted within the housing for connecting to the electrical control lines and RF power supply lines within the hand-supportable instrument (or the instrument controller as the case may be), and also for receiving the electrical control and RF power supply pins on the quick-connect multi-core plug 503; a pair of air-flow ports 510A, 510B mounted within the housing for connecting to the pair of air flow tubes within the instrument connected to the ends of the air cylinder supported therein (or within the instrument controller connected to the digitally-controlled multi-port valve assembly), and also for receiving the air-flow ports on the quick-connect multi-core plug 503 mated thereto; and a spring-loaded connector release button 511 mounted within the housing 506, for releasably engaging the mated quick-connect and release of the multi-core plug 503. FIG. 36C shows the multi-core connector assembly 501 from different perspectives. FIG. 36D shows the cylindrical mounting portion 507 of the housing of the multi-core connector assembly 501. FIG. 36E shows the cylindrical recess 508 of the housing of the multi-core connector assembly 504.

The Multi-Core Cable Construction of the Present Invention

As shown in FIG. 36A, the multi-core cable construction of the present invention 502 comprises: a pair of quick-connect multi-core plugs 503 and 503 adapted to receive the three (3) different ports formed within the multi-core connector assembly 501A, 501B installed within the instrument 401' and instrument controller 402' (as the case may be); and flexible length of multi-core cable 504 carrying electrical control wires, RF power wires and air-supply lines connected to the respective ports of the quick-connect multi-core plugs 503A and 503B.

Figure 36F:
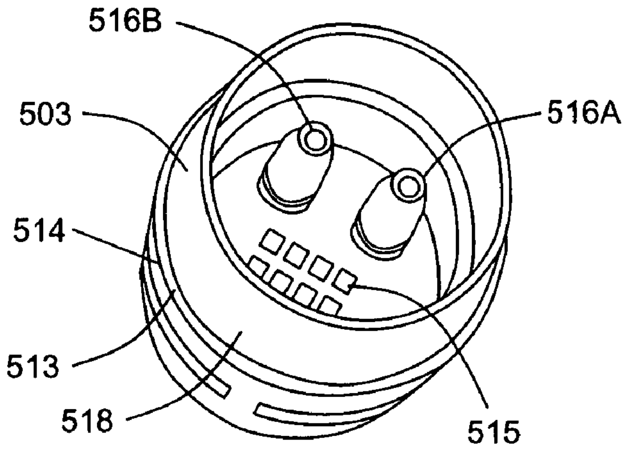
FIG. 36F is a perspective view of the second multi-port connector employed in the multi-port connector assembly of the present invention, viewed from the side which connects to the first multi-port connector shown in FIG. 36E.
Figure 36G:
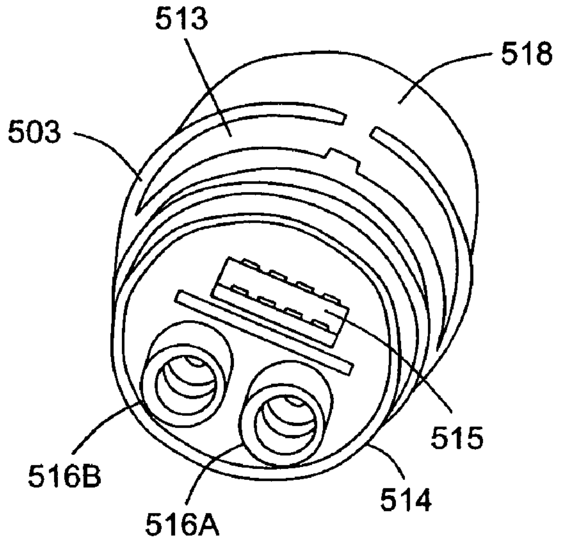
FIG. 36G is a perspective view of the second multi-port connector employed in the multi-port connector assembly of the present invention, viewed from the side which connects to the air tubing and electrical wiring contained within the flexible multi-core cable structure of the present invention shown in FIG. 36A.
Figure 36H:
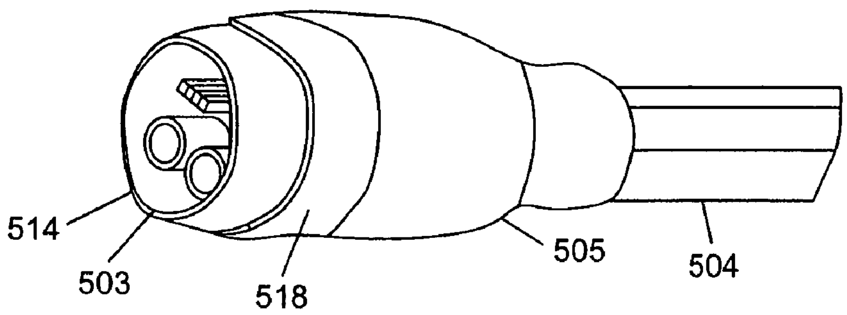
FIG. 36H is a perspective view of one end portion of the completed assembled flexible multi-port cable structure of the present invention, shown in FIG. 36A, showing a plastic shroud covering the portion of the cable structure where the tubing and wiring is joined to the second multi-port connector thereof, to seal off these connection interfaces from dirt, and other forms of debris.

As shown in FIG. 36F, each quick-connect multi-core plug 503 comprises: a plastic housing 513 having the cylindrical end portion 514 designed for insertion within the cylindrical recess 508 of the multi-port connector assembly 501; a pin connector 515 mounted within the housing for connecting to the pin connector 509 mounted within the multi-port connector assembly 501; a pair of air-flow port connectors 516A an 516B mounted within the connector housing 513 for connecting to the pair of air flow ports 516A, 516B; a cylindrical portion 518 supporting pin connector within the housing for connecting to the electrical control and RF power wires associated with the multi-core cable construction 504, and air-flow port connectors 516A, 516B for receiving the terminal portions of air tubing sections associated with the multi-core cable construction 504; and plastic shroud cover 505 for covering the interface of the multi-core plug and multi-core cable construction 502, to seal off these connection interfaces from dirt, and other forms of debris.

Figure 37A:
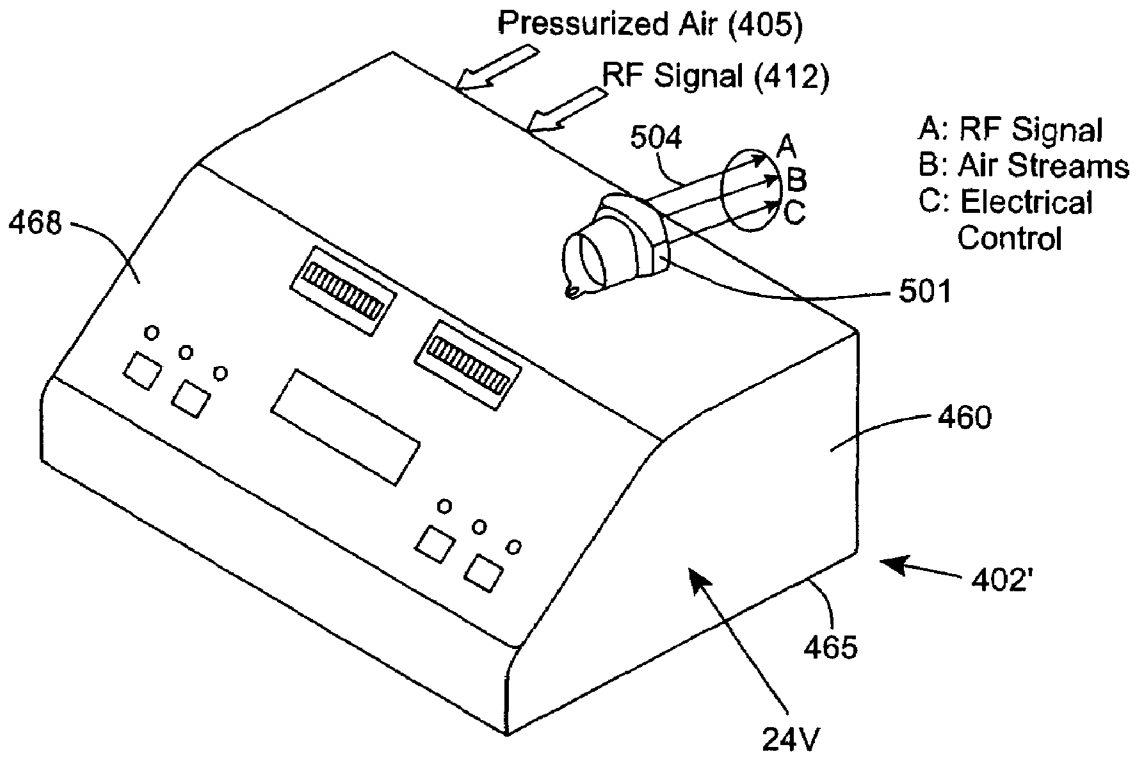
FIG. 37A is a perspective view of the intelligent instrument controller (i.e. control unit) of the present invention used in conjunction with the powered liposuction instrument illustrated in FIG. 35A, shown comprising: (1) a user control console having (i) four membrane type switches for selecting a desired cannula stroke length dimension (i.e. inches or centimeters) for measurement and display and for enabling and disabling electro-cautery function selection, (ii) six LED indicators for indicating power ON/OFF function selection, cannula stroke length dimension selection, and electro-cautery enable/disable function selection, (iii) a pair of LCD-based display panels for displaying (bar graph indications of inner cannula reciprocation rate (in cycles/sec) and inner cannula position measured by the cannula position sensor mounted within the hand-supportable liposuction instrument, and (iv) a LCD-based panel for displaying measured numerical values for the instantaneous rate of reciprocation for the inner cannula and the instantaneous stroke length thereof, and (2) a compact housing mounting a multi-port connector assembly shown in FIG. 36B, as well as an input port for receiving RF power signals generated from an external RF signal source, and an input port for receiving a source of pressurized air to drive the powered liposuction instrument of the present invention.
Figure 37B:
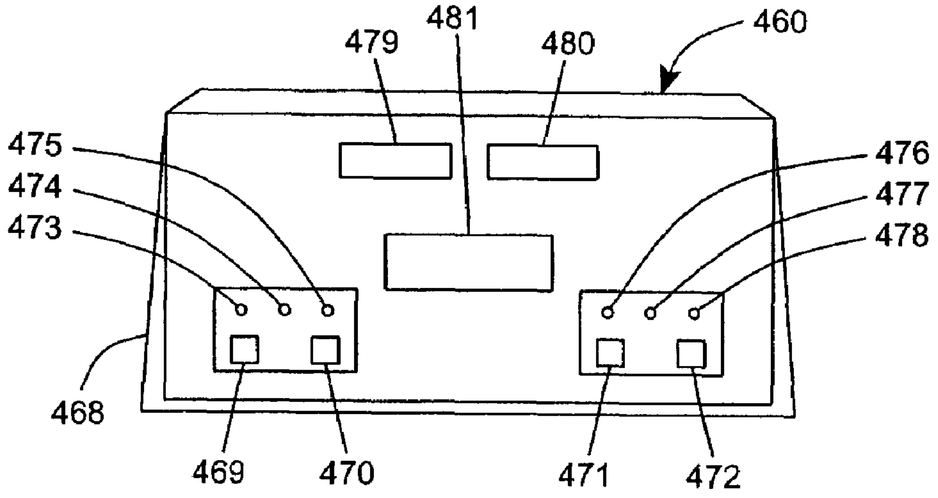
FIG. 37B is a graphical representation of the user control console portion of the intelligent instrument controller shown in FIG. 27A.

The intelligent instrument controller 402' shown in FIGS. 37A and 37B is essentially the same as the system controller 402 shown in FIGS. 27A and 27B, except that a multi-core connector assembly 501 is mounted within the rear portion of the controller housing to provide connections to pressurized air-flow supplies, electrical control signaling and RF power supply signaling.

Figure 35B:
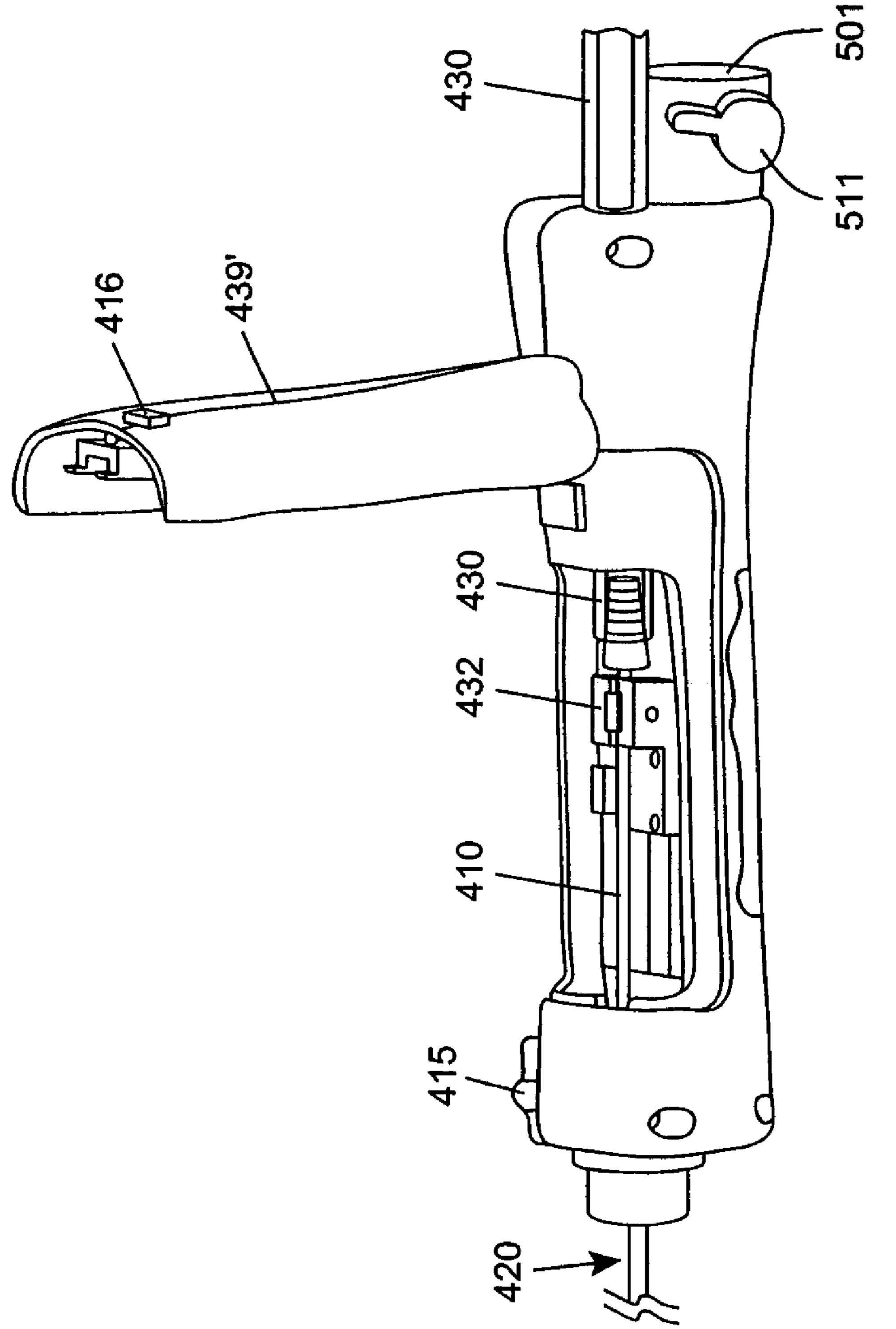
FIG. 35B is a perspective, partially cut-away view of the hand-supportable air-powered liposuction instrument of FIG. 35A, shown with its hinged cover panel arranged in its open configuration revealing its inner cannula installed within the actuator carriage assembly and connected to a section of flexible aspirating tubing that is ultimately connected to a vacuum-pressured aspiration pump subsystem (not shown)
Figure 38A:
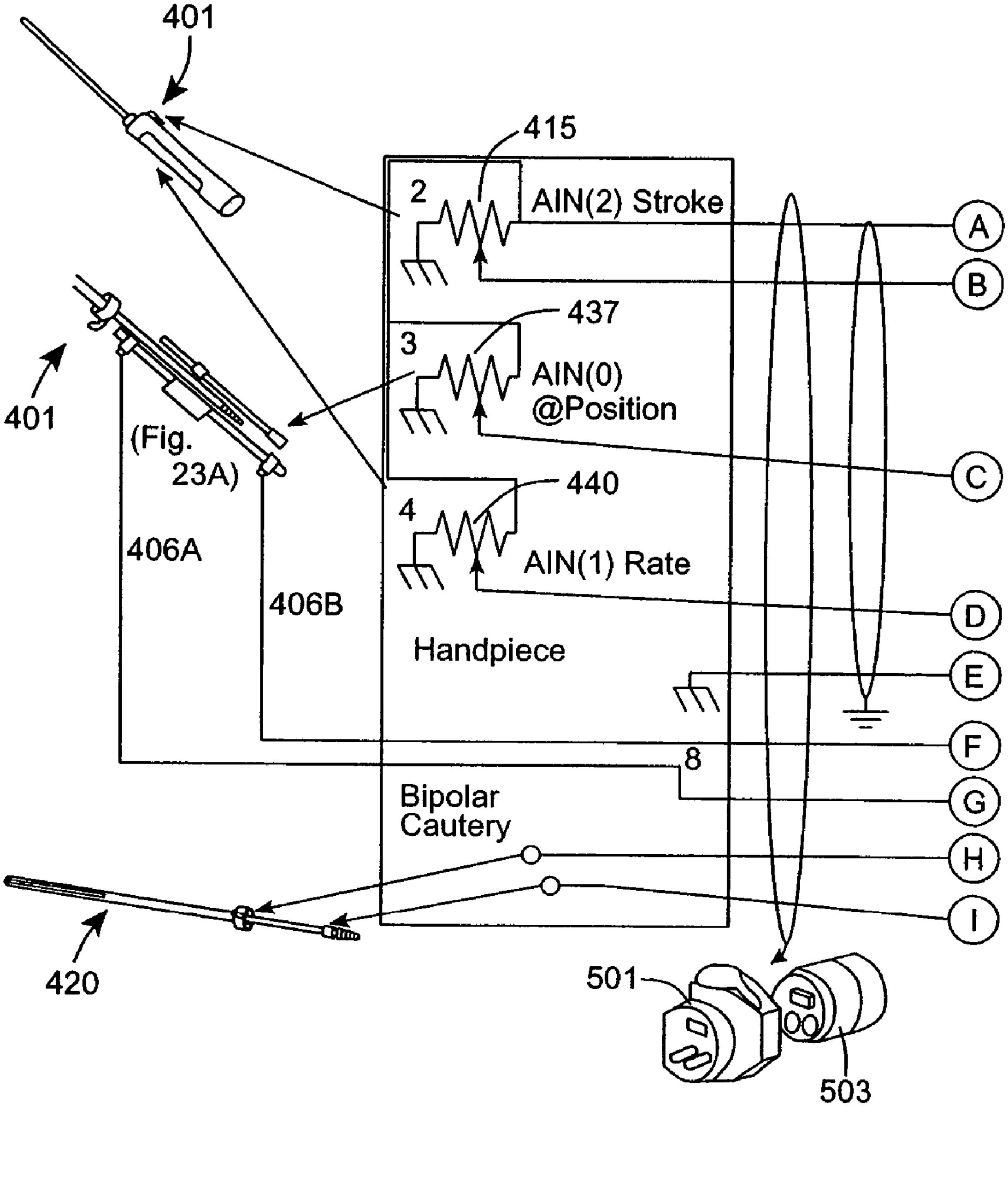
Figure 38B:
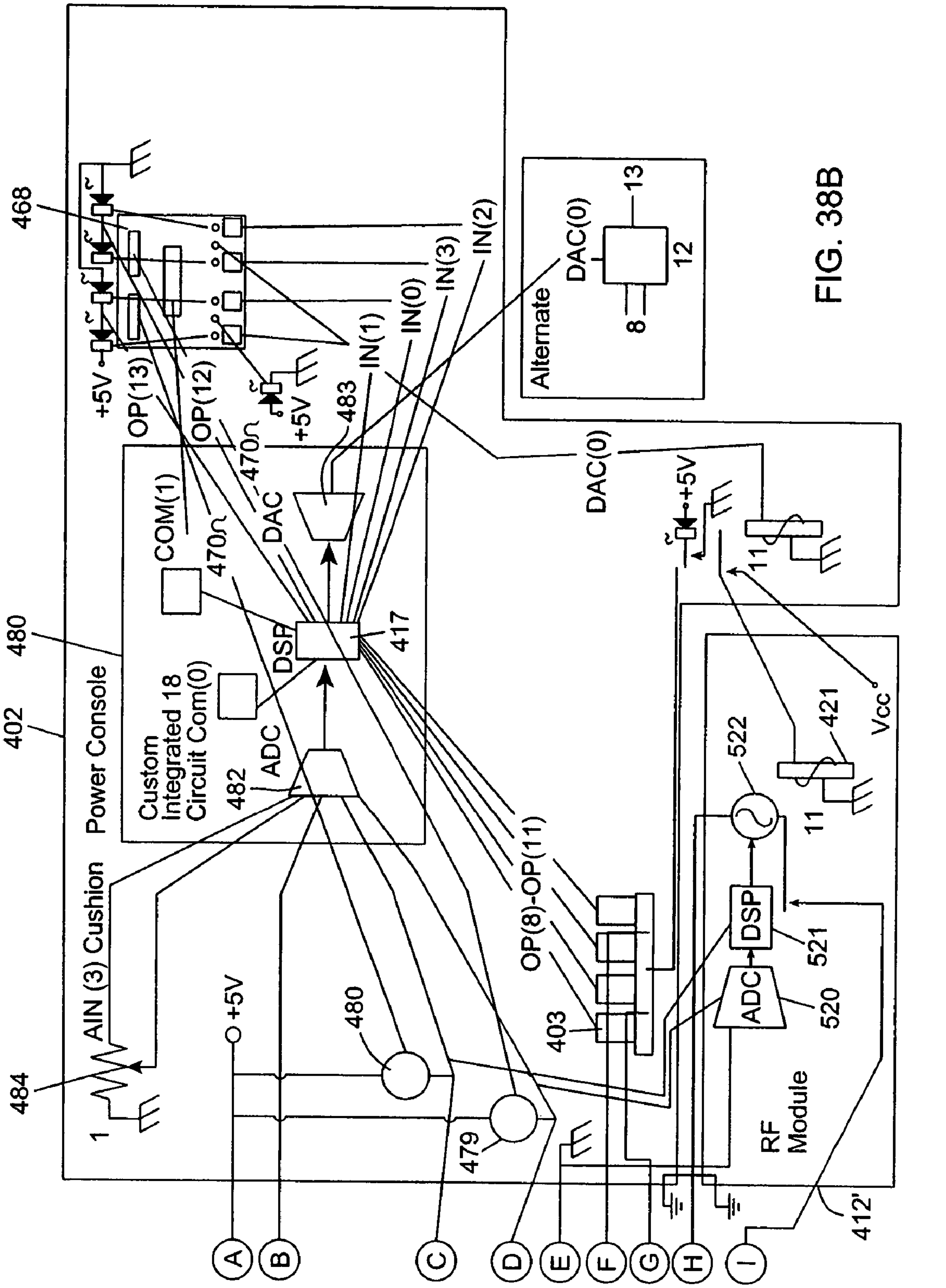

FIGS. 38A through 38C show a schematic diagram illustrating the connections between the components of the powered liposuction system shown in FIGS. 35A and 35B. Analog input voltages are indicated by AIN( ), whereas digital input signals (from the control console) are indicated by IN( ), and digital output signals are indicated by OP( ). The wiring connections from within the hand-supportable instrument to the multi-core connector assembly 501 are indicated in FIGS. 38A through 38C.

As illustrated in FIGS. 38A through 38C, instrument system 500 the intelligent instrument controller 402' further includes a second A/D converter 520 and a second DSP 521 which enables the system to measure and analyze the inner cannula stroke position and rate and, on a real-time basis, generate control signals which are used to control the RF power signal source 522, either realized within the instrument controller or external thereto, as described above. These RF control signals can be used to control the frequency, temporal and/or power characteristic of the RF power signal used to drive the electro-cauterizing cannula assembly employed by the instrument. In the event the RF power module is to be provided internal to the controller, proper RF shielding measures should be undertaken in a manner known in the art.

Figure 35C:
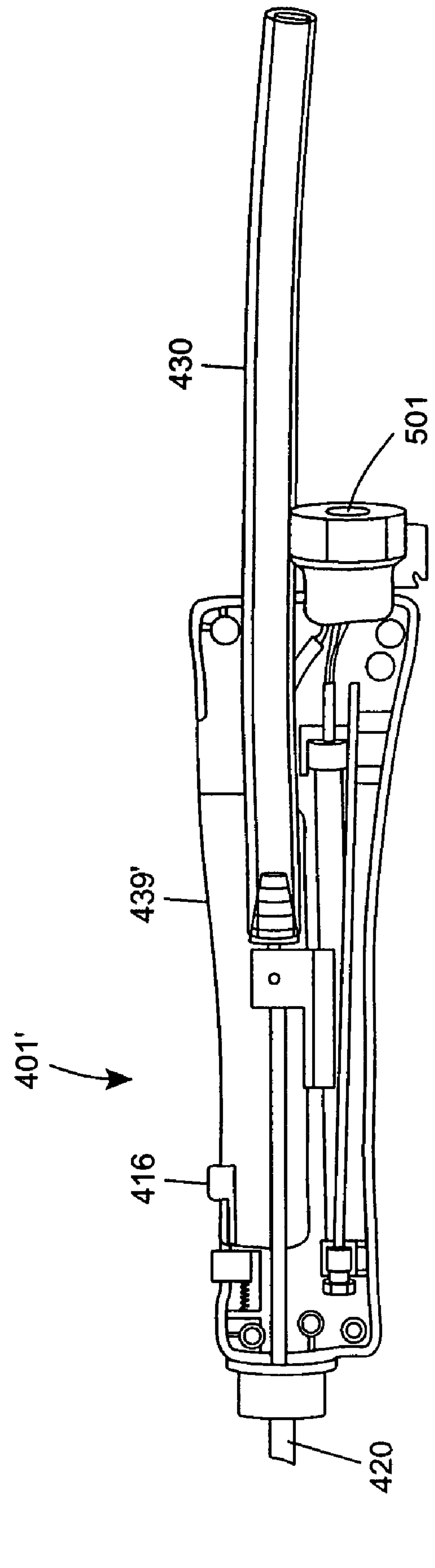
FIG. 35C is a cross-sectional, partially cut-away view of the hand-supportable air-powered liposuction instrument of FIG. 35A, taken along line 35C-35C indicated therein, illustrating how the flexible aspirating tube passes through the rear portion of the air-powered liposuction instrument and is permitted to reciprocate with the movement of the inner cannula during instrument operation.
Figure 39:
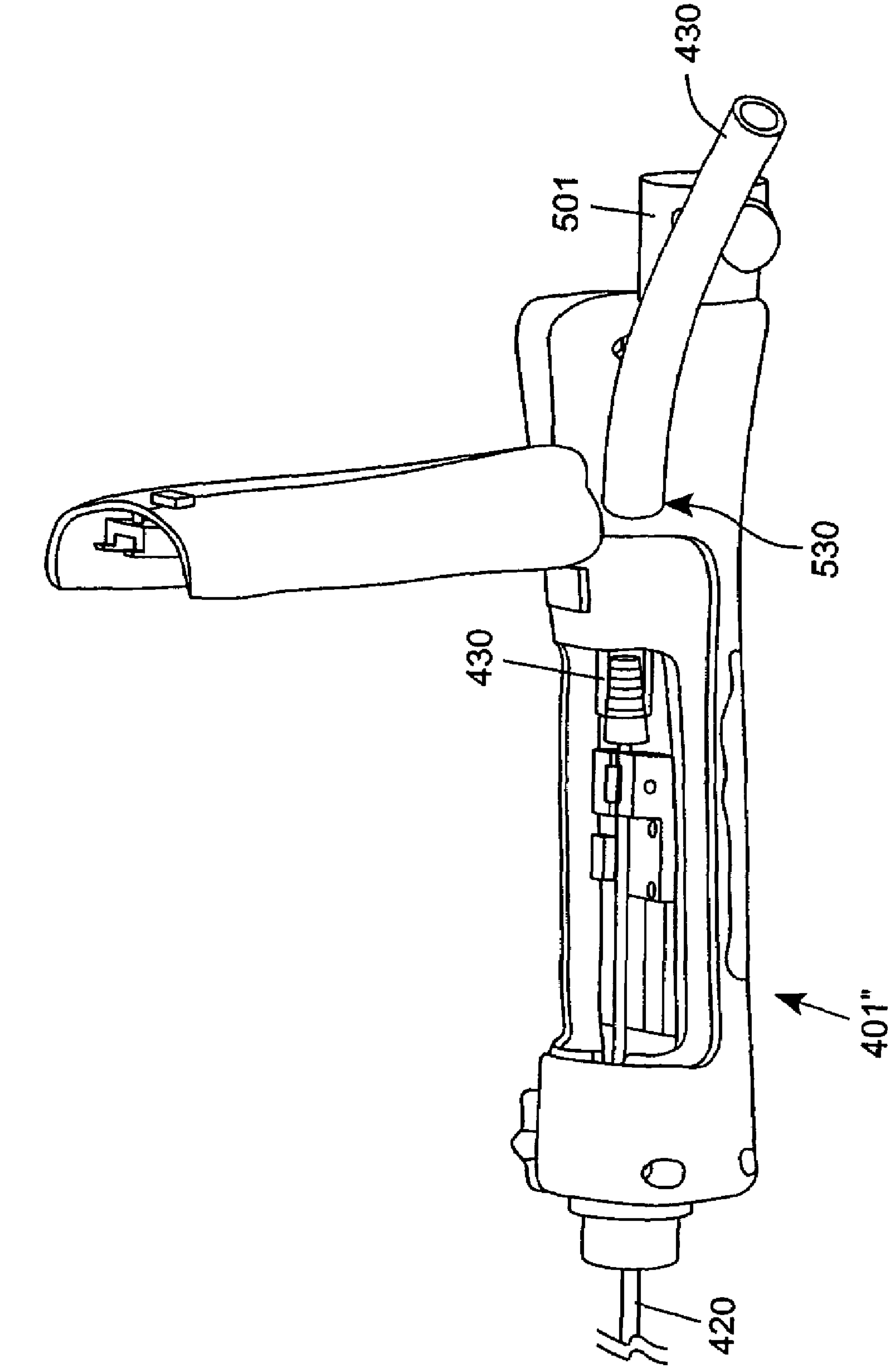
FIG. 39 is a perspective view of yet another illustrative embodiment of the air-powered liposuction instrument of the present invention, wherein the flexible aspiration tubing connected to the inner cannula is routed out through an exit port formed in the side surface of the rear portion of its hand-supportable housing.

Alternative Embodiments of the Power-Assisted Tissue Removal Instrument System of the Present Invention FIG. 39 shows an alternative embodiment of the air-powered liposuction instrument of FIGS. 35A through 35C, wherein the hand-supportable housing is designed to permit the aspiration tubing 430 to exit out of a port 530 formed along the side of the housing, towards its rear end. While there appear to be few, if any, advantages to this design over the preferred designs disclosed herein, it is believed that some surgeons may prefer that the aspiration tubing exits from the side of the instrument housing, rather from the rear end along the longitudinal axis of the instrument. In all other respects, this instrument system would be similar to that shown in FIGS. 35A through 35C and this incorporates the features thereof.

Figure 40A:
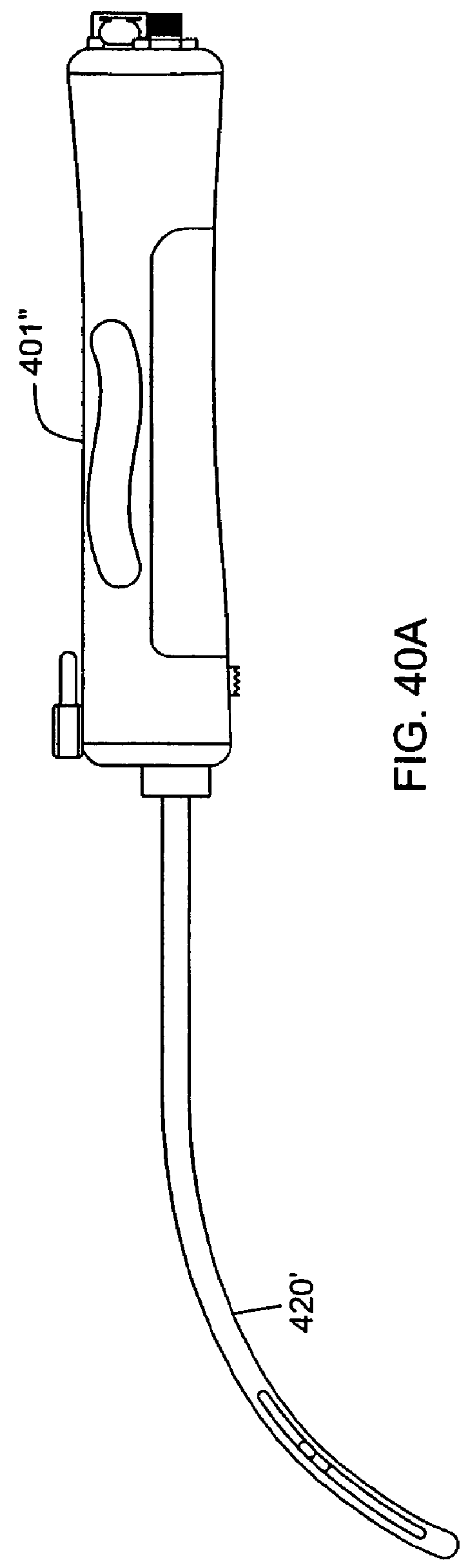
Figure 40B:
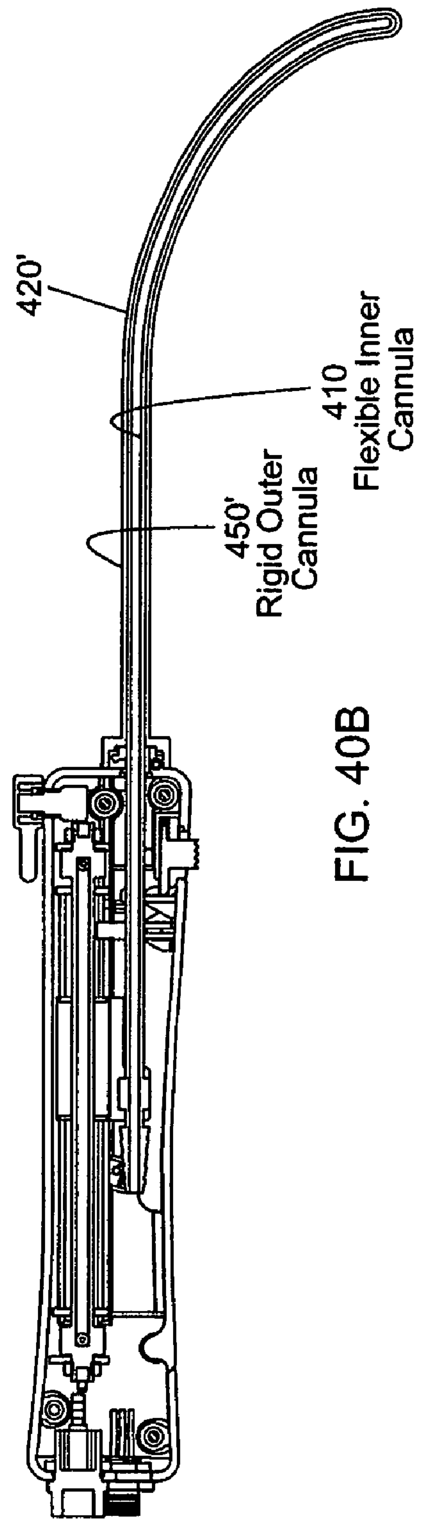
FIG. 40B is a cross-sectional view of the air-powered liposuction instrument shown in FIG. 38A, taken along line 38B-38B indicated therein, showing how that the inner cannula flexibly adapts to the rigid curved geometry of the outer cannula structure during inner cannula reciprocation operations.

In FIGS. 40A and 40B, there is shown an alternative embodiment of the air-powered liposuction instrument of the present invention 600, wherein a curved electro-cauterizing dual cannula assembly 420' is employed. As shown, the curved outer cannula 450 is rigid while the inner cannula 410' is made from a flexible material such as flexible resilient medical grade plastic material or the like. FIG. 40B shows how the inner cannula flexibly adapts to the rigid curved geometry of the outer cannula structure. In all other respects, this electro-cauterizing tissue-aspiration instrument system is similar to the system disclosed in FIGS. 35A through 35C and embodies all of the same features. The alternative cannula design is expected to have advantages when used to aspirate tissue from within various cavities of the human body.

Figure 41A:
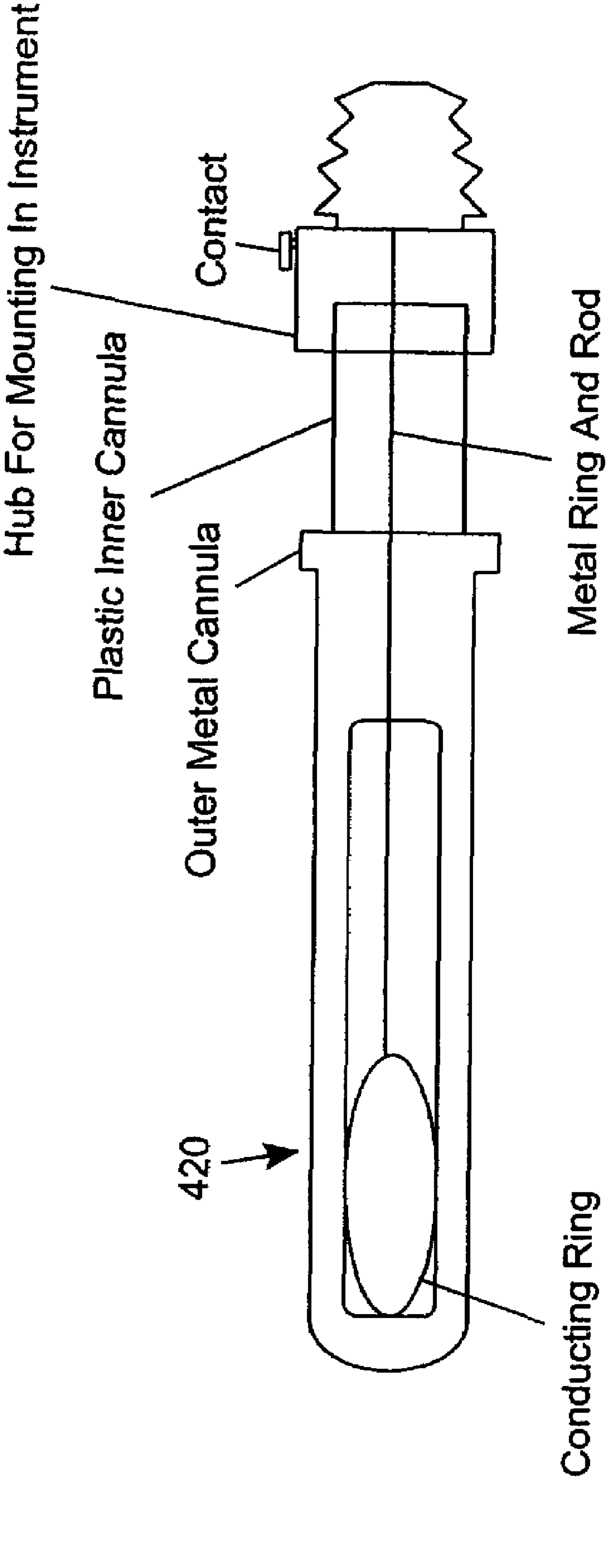
FIG. 41A is a schematic representation of an alternative bipolar-type electro-cauterizing dual cannula assembly for use with the powered liposuction instruments of the present invention, shown comprising an electrically conductive (e.g. metal) outer cannula for releasably mounting within the hand-supportable housing of a powered liposuction instrument, and a molded or extruded plastic inner cannula for slidable support with the outer cannula and reciprocation by the powered actuator, and wherein the plastic (non-conductive) inner cannula has a fine electrically conductive wire molded within the walls thereof which terminate in an electrically conductive ring about the aspiration aperture of the inner cannula, for conducting RF power signals from the base portion of the inner cannula to the electrically-conductive ring during powered liposuction and other tissue aspiration operations.
Figure 41B:
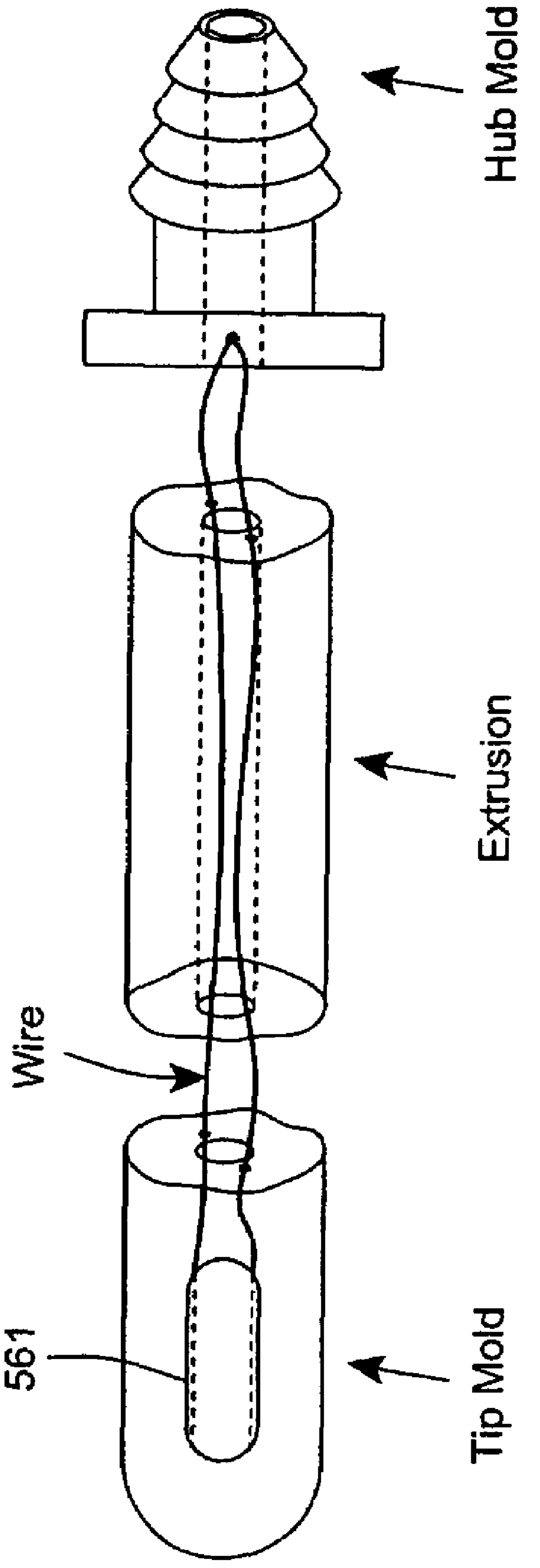
FIG. 41B is a schematic representation of an inner cannula structure for use with the bipolar electro-cauterizing dual cannula assembly shown in FIG. 41A.

In FIGS. 41A and 41B, there is shown an alternative bipolar-type electro-cauterizing dual cannula assembly for use with the powered liposuction instruments of the present invention. As shown, this cannula assembly 420" comprises: an electrically conductive (e.g. metal) outer cannula 450" for releasably mounting within the hand-supportable housing of a powered liposuction instrument; and a molded or extruded plastic inner cannula 410" for slidable support with the outer cannula and reciprocation by the actuator 409. In this embodiment shown in FIGS. 41A and 41B, the plastic (non-conductive) inner cannula 410" has a fine electrically conductive wire 560 molded within the walls thereof which terminate in an electrically conductive ring 561 about the aspiration aperture of the inner cannula. The purpose of this structure is to conduct RF power signals from the base portion of the plastic inner cannula to the electrically-conductive ring during powered liposuction and other tissue aspiration operations. In this dual cannula assembly, the outer cannula could be made from electrically-conductive material.

In FIG. 42, there is shown an alternative electro-cauterizing dual cannula assembly 570 for use in the powered liposuction instruments of the present invention. In this alternative embodiment, a stream of irrigation fluid 571 is pumped from the base portion of the outer cannula 572 to the distal portion thereof, along a micro-sized fluid conduit formed along the surface walls of the outer cannula, and is released into the interior distal portion of the outer cannula through a small opening 572 formed therein, for infiltration and irrigation of tissue during aspiration in order to facilitate pump action. This cannula design will be useful in tissue-aspiration applications in which irrigation fluid is required or desired.

In FIG. 43A, there is shown another alternative design for an electro-cauterizing powered liposuction instrument of the present invention, indicated by referencee numeral 700. In this illustrative embodiment, the inner cannula 410' is loaded through an inner cannula loading port 701 provided at the rear of the instrument housing, and thereafter is snap-fitted into position within recess 702 in the carriage portion 703 of the air-powered actuator structure 704 installed therein. During such inner cannula loading operations, the outer cannula 420 should be first connected to the front portion of the hand-supportable housing, and then the actuator structure 704 retracted to the rear portion of the hand-supportable housing. Then, the distal portion of the inner cannula 410' would be inserted first through the cannula loading port 701, and then its base portion 705 snap-fitted within recess 703 in the actuator carriage 703. Thereafter, a length of aspirating tubing can be connected to the barbed end 706 of the cannula base portion 705 by a push-inwardly type of action. Alternatively, the aspirating tube can be first connected to the base portion of the inner cannula, and then the inner cannula/tubing subassembly loaded into the inner cannula loading port of the instrument. An advantage offered by this rear-loading instrument design 700 is that it is possible to eliminate the need to open the hinged door panel each and every time the surgeon desires to change cannulas during surgical operations, and possibly even eliminate the hinged door panel entirely, in particular instrument designs.

Notably, the electronically-controlled air-powered cannula reciprocation subsystem, intelligent instrument controller, and multilayer cable subsystem disclosed in connection with the illustrative embodiment of FIGS. 20A through 40B, can also be used in single cannula designs as taught in FIGS. 15-19, incorporated herein by reference.

While the particular embodiments shown and described above have proven to be useful in many applications in the liposuction art, further modifications of the present invention disclosed herein will occur to persons skilled in the art to which the present invention pertains. All such modifications are deemed to be within the scope and spirit of the present invention defined by the appended claims.

What is claimed is:

1. An air-powered tissue-aspiration instrument system comprising:

(A) an air-powered tissue-aspiration instrument including (i) a hand-supportable housing having a front end portion and a rear end portion, and an air-powered reciprocation mechanism disposed in said hand-supportable housing and including a dual-port air-driven cylinder having first and second ports for receiving a pair of pressurized air streams to drive said air-powered reciprocation mechanism;

(ii) a dual-cannula assembly being operably connectable to said hand-supportable housing and including a hollow inner cannula having a distal end and a proximal end and an inner suction aperture about said inner cannula distal end, said inner cannula proximal end further including an outlet port and a continuous passageway which communicates said inner suction aperture with said outlet port, and a hollow outer cannula mounted stationary relative to said hand-supportable housing and having a distal end and a proximal end and an outer suction aperture about said outer cannula distal end, said hollow inner cannula being disposed within at least a portion of said hollow outer cannula while permitting aspiration of tissue through said outer and inner suction apertures, along said continuous passageway and out of said outlet port; and (iii) a first multi-port connector provided on the rear end portion of said hand-supportable housing, and supporting a first set of air-power supply-line connectors and electrical control signal connectors;

(B) an instrument controller having a controller housing containing a digitally-controlled multi-port air-flow control valve assembly including (i) a central air-flow control port for operable connection to an external source of pressurized air, (ii) a first air-flow control port for communication with the first port on said dual-port air-driven cylinder, and (iii) a second air-flow control port for communication with the second port on said dual-port air-driven cylinder; and (iv) a second multi-port connector provided on the housing of said instrument controller, and supporting a second set of air-power supply-line connectors and electrical control signal connectors; and (C) a multi-core connector assembly including (i) a first multi-port connector plug adapted for connection to said first multi-port connector, (ii) a second multi-port connector plug adapted for connection to said second multi-port connector, and (iii) a multi-core cable structure for interconnecting said first and second multi-port connector plugs, and including a pair of air-supply tubes and a set of electrical control signal wires encased within a flexible casing; and wherein when said first multi-port connector plug is connected to said first multi-port connector and said second multi-port connector plug is connected to said second multi-port connector, then said first set of air-power supply-line connectors are operably connected to said second set of air-power supply-line connectors by way of said pair of air-supply tubes, and also said first set of electrical control signal connectors are electrically connected to said second set of electrical control signal connectors by way of said set of electrical control signal wires.

2. The air-powered tissue-aspiration instrument system of claim 1, wherein digital output control voltage signals are provided to electrically-controlled air-flow control valves so as to electronically control the operation of said air-powered reciprocation mechanism.

3. The air-powered tissue-aspiration instrument system of claim 2, wherein digital output control voltage signals are provided to the electrically-controlled air-flow control valves embodied within said multi-port air-flow control valve assembly, so as to electronically control the operation of said air-powered reciprocation mechanism.

4. The air-powered tissue-aspiration instrument system of claim 1, wherein said instrument controller employs a system control program that runs on a digital signal processor disposed in said controller housing.

5. The air-powered tissue-aspiration instrument system of claim 1, wherein analog voltage input signals are generated from within said air-powered tissue-aspiration instrument and supplied as analog input voltage signals to said instrument controller for detection, A/D conversion and digital signal processing.

6. The air-powered tissue-aspiration instrument system of claim 1, wherein digital voltage output control signals are generated within said instrument controller and supplied as output voltage signals to said multi-port air-control valve assembly within said instrument controller so as to generate said pair of pressurized air-supply streams that are supplied to said air-powered tissue-aspiration instrument liposuction instrument via said multi-port connector assembly.

7. The air-powered tissue-aspiration instrument system of claim 1, wherein said air-powered tissue-aspiration instrument further comprises a position sensing transducer disposed in said hand-supportable housing, for measuring the instantaneous stroke position of said hollow inner cannula during reciprocation operations.

8. The air-powered tissue-aspiration instrument system of claim 1, wherein a cannula reciprocation stroke control switch is mounted on said hand-supportable housing for operation by a surgeon's thumb.

9. The air-powered tissue-aspiration instrument system of claim 8, wherein said cannula reciprocation rate control switch is realized using a flexible potentiometer that is deformed upon the surgeon squeezing a spring-biased hinged door panel provided on said hand-supportable housing.

10. The air-powered tissue-aspiration instrument system of claim 1, wherein said dual-cannula assembly further comprises electro-cauterizing electrodes provided at said aspiration aperture.

11. The air-powered tissue-aspiration instrument system of claim 10, wherein said first multi-port connector provided on the rear portion of said hand-supportable housing further supports a first set of RF signal connectors operably connected to said electro-cauterizing electrodes.

12. The air-powered tissue-aspiration instrument system of claim 11, wherein said second multi-port connector provided on the housing of said instrument controller, further supports a second set of RF signal connectors operably connected to an RF signal generator, and wherein said multi-core cable structure further includes a pair RF signal wires encased within said flexible casing.

13. The air-powered tissue-aspiration instrument system of claim 12, wherein when said first multi-port connector plug is connected to said first multi-port connector and said second multi-port connector plug is connected to said second multi-port connector, then said first set of RF signal connectors are operably connected to said second set of RF signal connectors by way of said pair of RF signal wires.

14. The air-powered tissue-aspiration instrument system of claim 12, wherein said instrument controller (i) supplies air-power to said air-powered reciprocation mechanism within said hand-supportable housing, (ii) communicates electrical control signals between said instrument and said intelligent controller, and (iii) delivers RF power signals to said electro-cauterizing electrodes during system operation.

* * * * *